US011097444B1

(12) United States Patent
Ha'Eri

(10) Patent No.: US 11,097,444 B1
(45) Date of Patent: Aug. 24, 2021

(54) BONDING WOOD OR OTHER PLANT PRODUCTS USING ULTRASOUND ENERGY

(71) Applicant: Bobak Ha'Eri, Minnetonka, MN (US)

(72) Inventor: Bobak Ha'Eri, Minnetonka, MN (US)

( * ) Notice: Subject to any disclaimer, the term of this patent is extended or adjusted under 35 U.S.C. 154(b) by 0 days.

(21) Appl. No.: 17/155,872

(22) Filed: Jan. 22, 2021

(51) Int. Cl.
*B27N 3/02* (2006.01)
*B27N 3/04* (2006.01)
*B27N 3/18* (2006.01)
*B29C 65/08* (2006.01)
*B29C 65/82* (2006.01)
*B32B 37/10* (2006.01)
*B32B 38/16* (2006.01)
*G01N 33/46* (2006.01)
*B27K 5/00* (2006.01)

(52) U.S. Cl.
CPC .............. *B27N 3/18* (2013.01); *B27K 5/0065* (2013.01); *B27N 3/02* (2013.01); *B27N 3/04* (2013.01); *B29C 65/08* (2013.01); *B29C 65/8292* (2013.01); *B32B 37/1045* (2013.01); *B32B 38/162* (2013.01); *G01N 33/46* (2013.01); *B32B 2310/028* (2013.01); *G01N 2291/0238* (2013.01)

(58) Field of Classification Search
CPC ............ B06B 2201/70; B06B 2201/71; B06B 2201/72; B27D 1/04; B27K 5/0065; B27K 2200/10; B27K 2200/15; B27K 2240/00; B27K 2240/15; B27N 1/00; B27N 1/02; B27N 1/0209; B27N 1/0263; B27N 1/029; B27N 3/002; B27N 3/02; B27N 3/04; B27N 3/08; B27N 3/10; B27N 3/12; B27N 3/14; B27N 3/143; B27N 3/16; B27N 3/18; B32B 21/00; B32B 21/02; B32B 21/042; B32B 21/13; B32B 21/14; B32B 37/1045; B32B 38/162; B32B 2264/02; B32B 2264/0214; B32B 2264/105; B32B 2264/1055; B32B 2310/028; B29C 65/08; B29C 65/081; B29C 65/083; B29C 65/085; B29C 65/086; B29C 65/087; B29C 65/088; B29C 65/8292; G01N 29/04; G01N 29/043; G01N 29/07; G01N 29/09; G01N 29/11; G01N 29/265; G01N 29/27; G01N 29/275; G01N 29/32; G01N 33/46; G01N 2291/0231; G01N 2291/0238
See application file for complete search history.

(56) References Cited

U.S. PATENT DOCUMENTS

| 2,779,969 A | 2/1957 | Bose |
| 2,909,804 A | 10/1959 | Means |
| 3,044,111 A | 7/1962 | Caughey |

(Continued)

OTHER PUBLICATIONS

Coxworth, Ben, "Ultrasound thermomgraphy used to find flaws in wood," New Atlas, Aug. 9, 2011, Available online at https://newatlas.com/ultrasound-thermography-wood-defects/19476/, retrieved Apr. 21, 2021, 7 pages.

(Continued)

*Primary Examiner* — Michael A Tolin
(74) *Attorney, Agent, or Firm* — Krenz Patent Law, LLC

(57) ABSTRACT

A filler material is applied to a plurality of wood elements. The plurality of wood elements is bonded into a composite wood product, where the bonding includes delivering ultrasound energy to the plurality of wood elements. The ultrasound energy has a frequency within a frequency range of 10 kHz-20 MHz.

38 Claims, 21 Drawing Sheets

(56) References Cited

U.S. PATENT DOCUMENTS

| | | | |
|---|---|---|---|
| 3,053,124 | A | 9/1962 | Balamuth et al. |
| 3,459,610 | A | 8/1969 | Dijkers et al. |
| 3,644,161 | A | 2/1972 | Hall |
| 3,670,133 | A | 6/1972 | Admiraal |
| 3,710,064 | A | 1/1973 | Mathur |
| 3,711,674 | A | 1/1973 | Admiraal |
| 4,005,301 | A | 1/1977 | Thourel |
| 4,018,642 | A | 4/1977 | Pike et al. |
| 4,020,311 | A | 4/1977 | Churchland |
| 4,456,498 | A | 6/1984 | Churchland |
| 4,479,912 | A * | 10/1984 | Bullock .................. C08L 97/02 264/109 |
| 4,517,148 | A | 5/1985 | Churchland |
| 5,228,947 | A | 7/1993 | Churchland |
| 5,892,208 | A | 4/1999 | Harris et al. |
| 6,029,520 | A * | 2/2000 | Beall ....................... G01N 29/11 73/579 |
| 6,066,284 | A * | 5/2000 | Hunt ....................... G01N 29/07 264/109 |
| 6,201,224 | B1 | 3/2001 | Churchland et al. |
| 6,242,726 | B1 | 6/2001 | Harris et al. |
| 6,287,410 | B1 | 9/2001 | Klemarewski |
| 6,368,544 | B1 | 4/2002 | Owens |
| 6,521,288 | B2 * | 2/2003 | Laks ....................... A01N 25/12 427/180 |
| 6,744,025 | B2 | 6/2004 | Vilo |
| 7,048,825 | B2 | 5/2006 | Churchland et al. |
| 7,070,676 | B2 | 7/2006 | Churchland et al. |
| 7,089,685 | B2 | 8/2006 | Torgovnikov et al. |
| 8,105,451 | B2 * | 1/2012 | Krebs .................. B27N 1/0254 156/73.1 |
| 8,414,720 | B2 | 4/2013 | Churchland et al. |
| 8,435,430 | B2 * | 5/2013 | Gupta ...................... B27N 3/04 264/122 |
| 9,128,027 | B2 * | 9/2015 | Benedetti ............... G01N 29/04 |
| 2005/0127067 | A1 | 6/2005 | Ristola et al. |

OTHER PUBLICATIONS

Qiu, Shu; Wang, Zhenyu; He, Zhengbin; Yi, Songlin, "The Effect of Ultrasound Pretreatment on Poplar Wood Dimensional Stability," bioresources.com, Aug. 2016, pp. 7811-7821, vol. 11(3), Available online at https://www.researchgate.net/publication/306295144, retrieved Apr. 21, 2021, 12 pages.

Espinoza, Omar; Bond, Brian, "Vacuum Drying of Wood—State of the Art," Current Forestry Reports, Dec. 2016, Published online Oct. 14, 2016, pp. 223-235, vol. 2, Issue 4, Available online at https://link.springer.com/content/pdf/10.1007/s40725-016-0045-9.pdf, retrieved Apr. 21, 2021, 13 pages.

He, Z.; Yang, F.; Peng, Y.; Yi, S., "Ultrasound-assisted vacuum drying of wood: Effects on drying time and product quality," BioResources, 2013, pp. 855-863, vol. 8(1), Available online at https://bioresources.cnr.ncsu.edu/resources/ultrasound-assisted-vacuum-drying-of-wood-effects-on-drying-time-and-product-quality/, retrieved Apr. 21, 2021, 7 pages.

He, Zhengbin; Zhang, Yu; Qiu, Shu, Zhao, Zijian, Yi, Songlin, "Water Distribution During Ultrasound-assisted Vacuum Drying of Wood," Wood Research, 2016, pp. 341-350, vol. 61 (3), Available online at http://www.woodresearch.sk/wr/201603/01.pdf, retrieved Apr. 21, 2021, 10 pages.

* cited by examiner

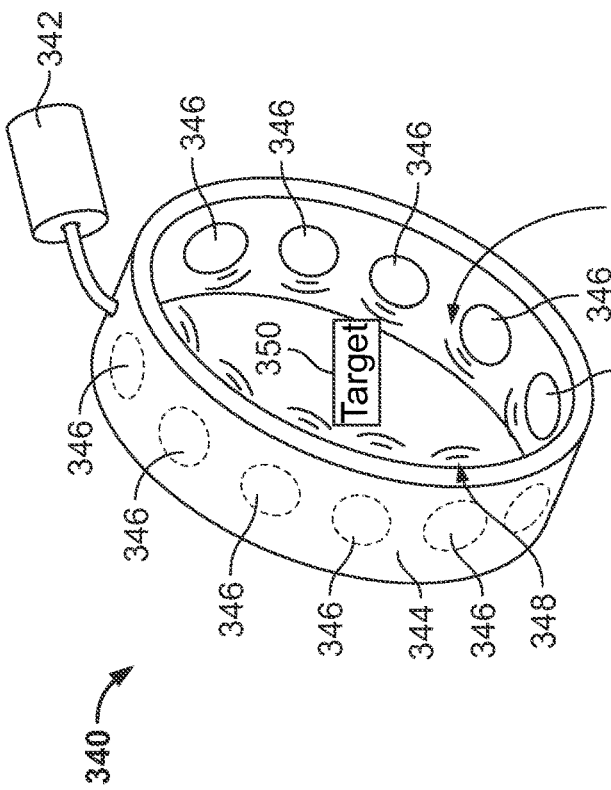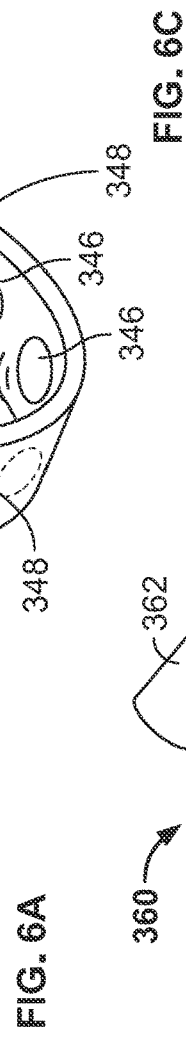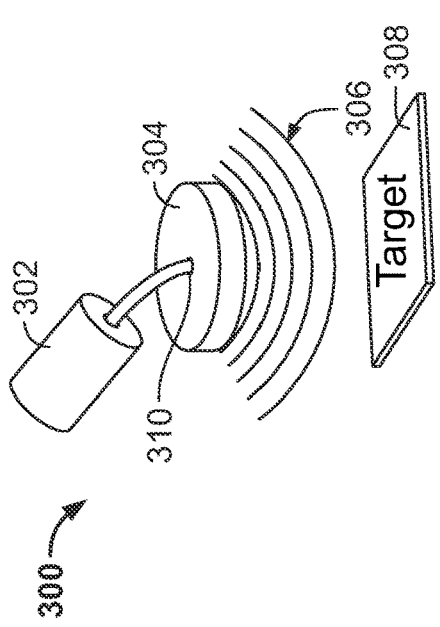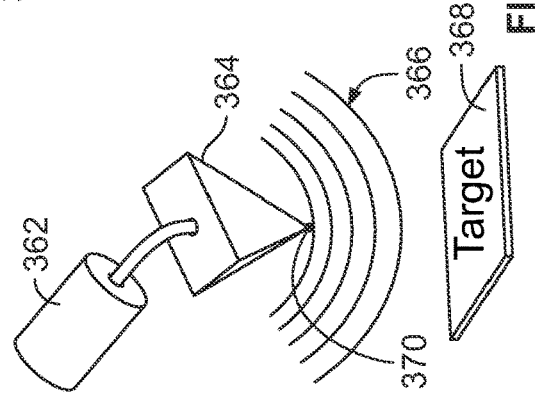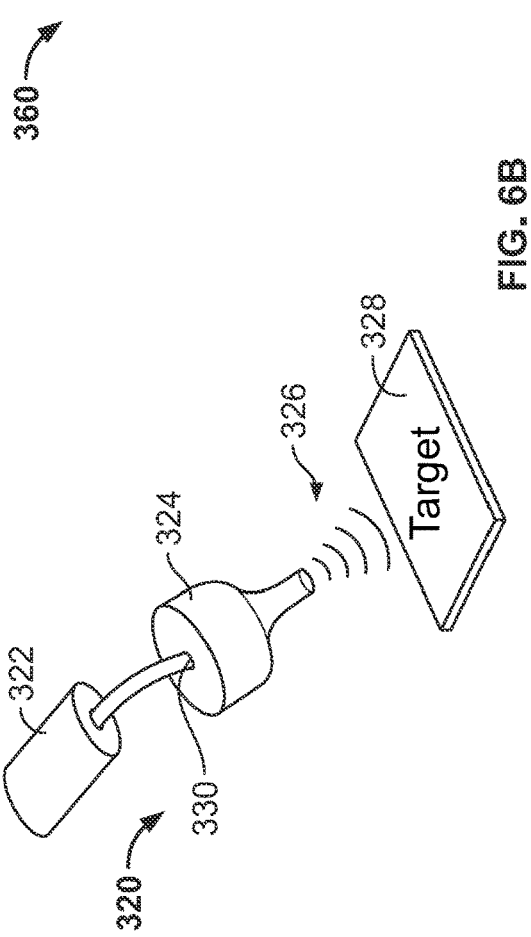

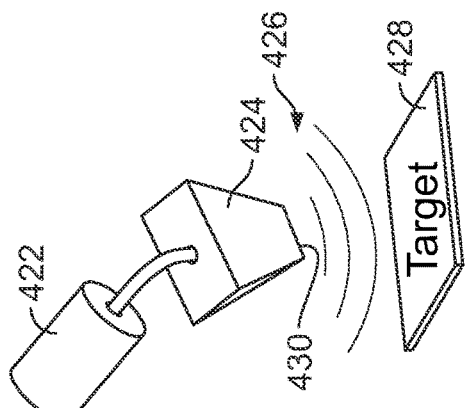
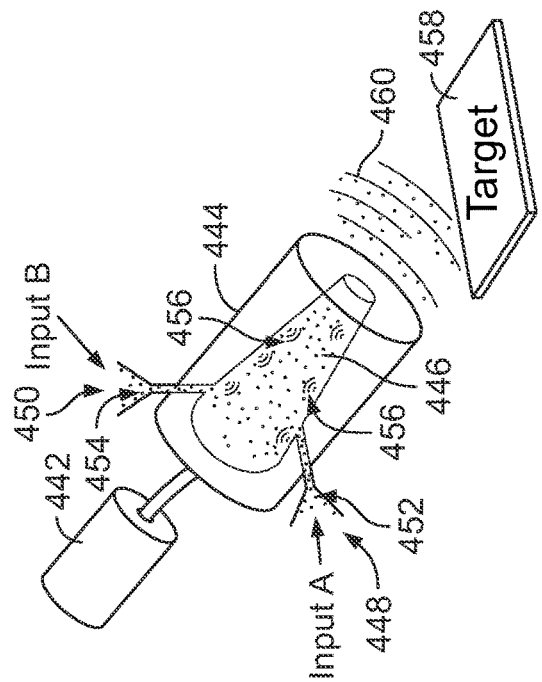
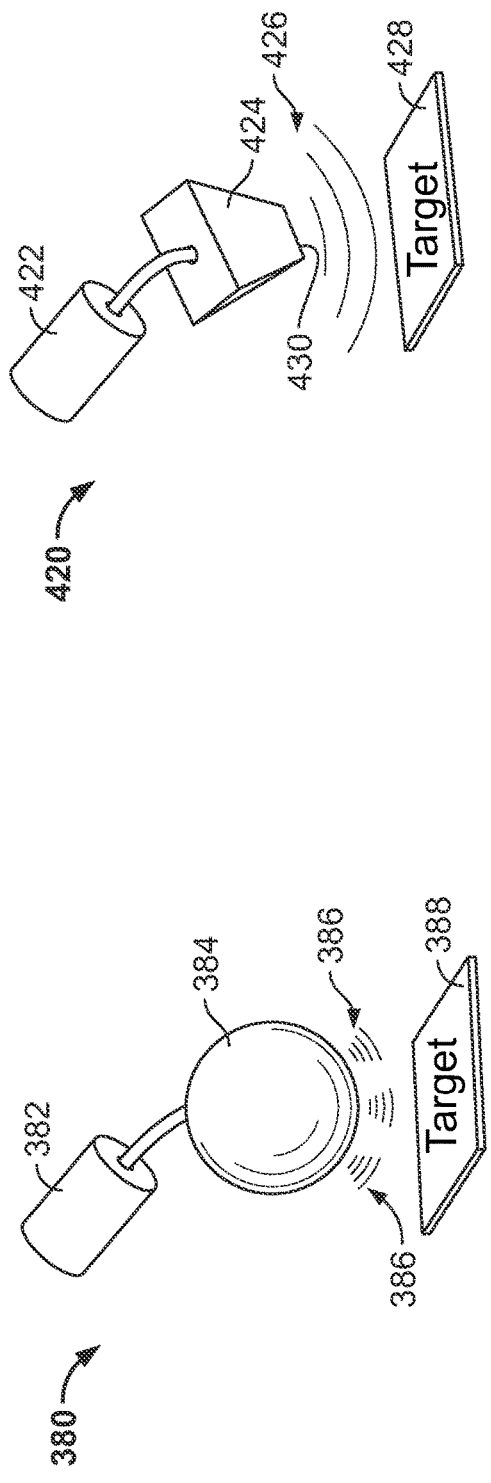
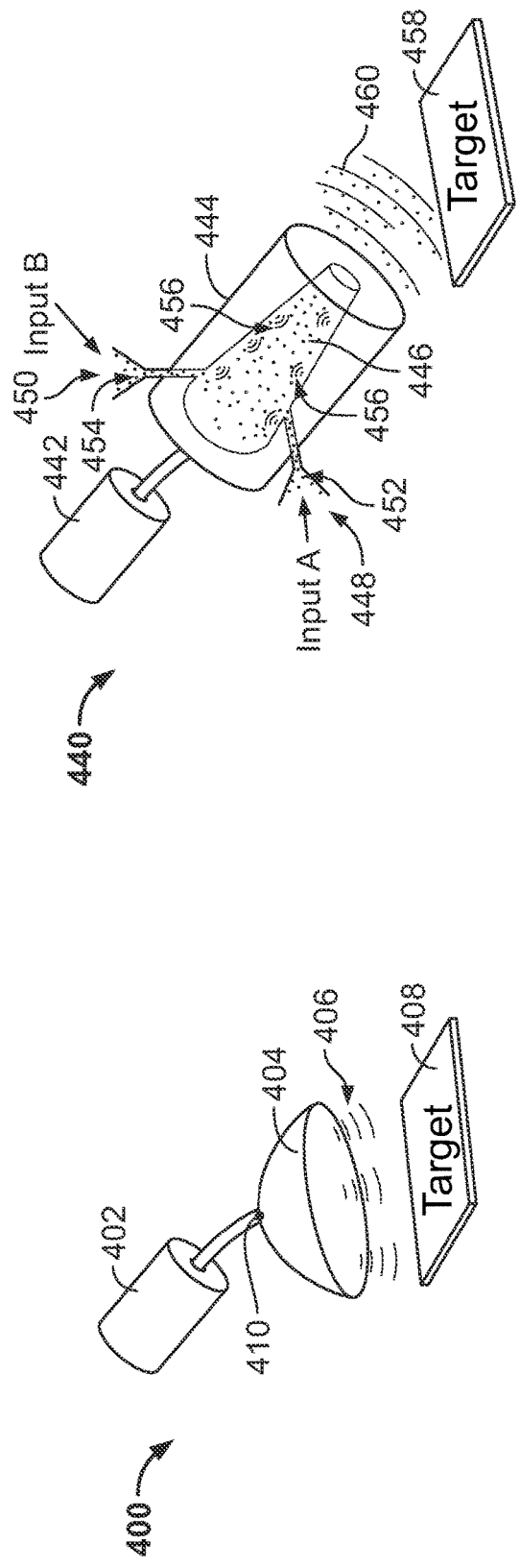

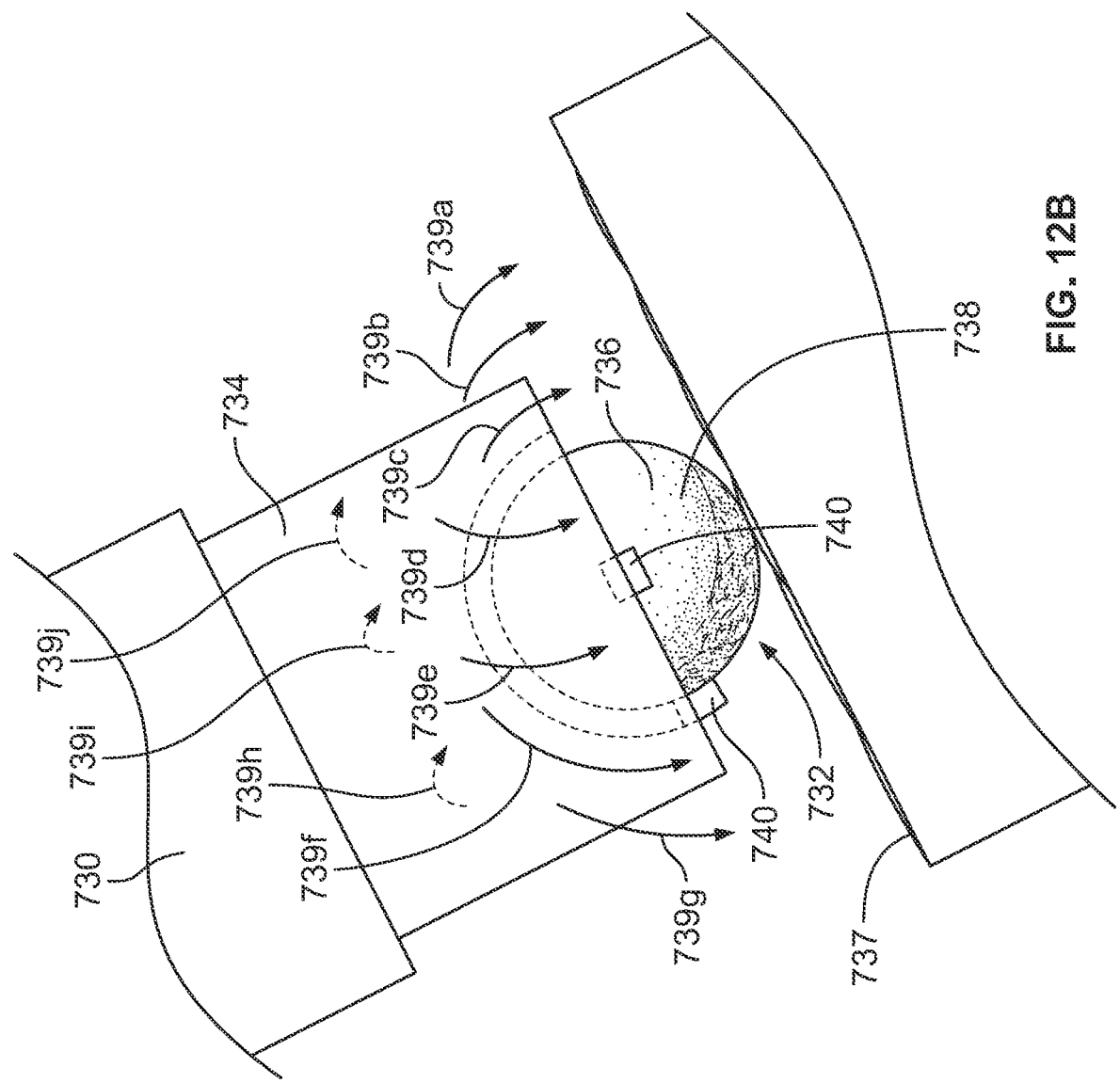

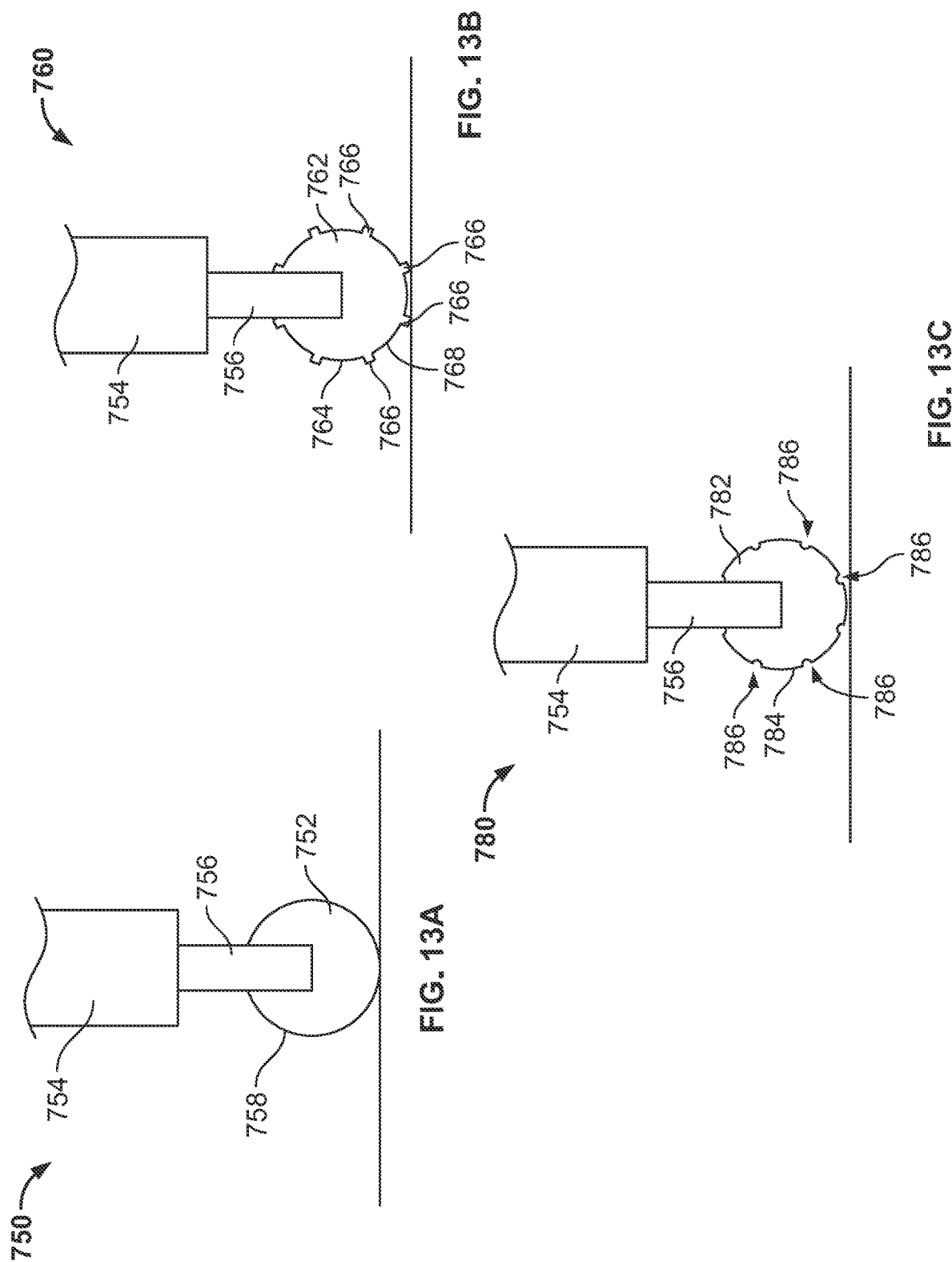

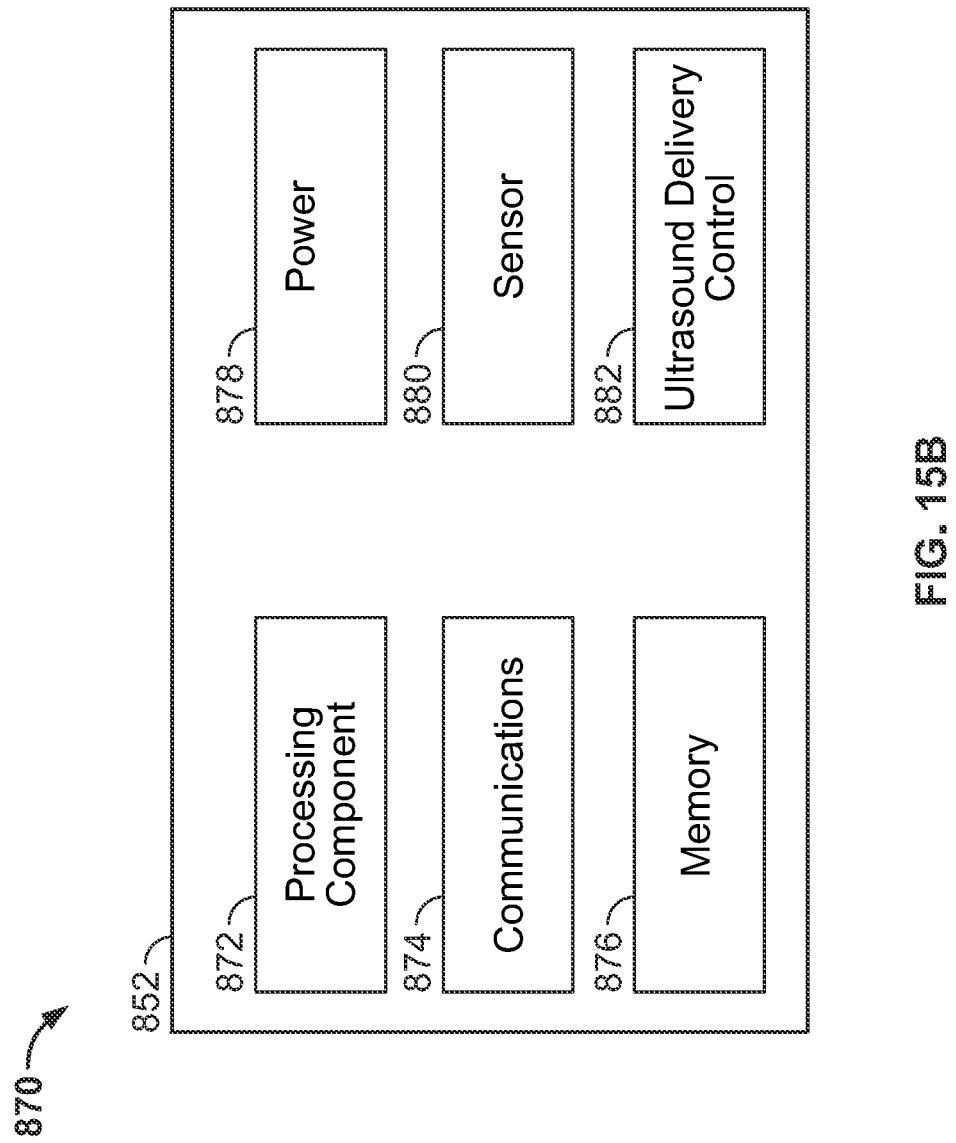

BONDING WOOD OR OTHER PLANT PRODUCTS USING ULTRASOUND ENERGY

TECHNICAL FIELD

This document generally describes devices, systems, and methods for bonding wood or other plant products using ultrasound energy.

BACKGROUND

Engineered wood products have been manufactured using lumber, veneers, wood strands, or other small wood elements, and binding them together with resin to form structural products. In this manner, smaller or lower-grade logs or wood elements can be used to produce large-lumber substitutes. Engineered wood products have been used in structural applications such as girders, beams, joists, headers, studs, and columns, and have been used instead of, or together with, lumber products.

Ultrasound energy has been used for diagnostic imaging in medical applications. With ultrasound imaging, a probe transmits high-frequency sound pulses into a body. The sound pulses propagate as waves into the body, passing through some bodily fluids and body tissues, while being partially absorbed by other body tissues, where the absorption causes a partial reflection or echo of the sound waves back towards the probe. A sensor in the probe measures the echoed sound waves, and the information can be used to create a diagnostic image of the area of the body being examined.

Ultrasound energy has also been used for diagnostic imaging and non-destructive testing in industrial applications, such as testing welds in metal, detecting defects within concrete or assessing consistency of concrete, and detecting defects in wood. In one application, a probe transmits high-frequency sound pulses into the material to be imaged or tested, and a sensor in the probe measures echoed sound waves that return to the probe. In another application, a separate receiver unit on a side of the material opposite the probe receives sound waves that pass through the material being imaged or tested after the probe transmits high-frequency sound pulses into the material.

SUMMARY

In a general aspect, a method for manufacturing a composite wood product includes applying a filler material to a plurality of wood elements, and bonding the plurality of wood elements into a composite wood product, where the bonding includes delivering ultrasound energy to the plurality of wood elements. The ultrasound energy has a frequency within a frequency range of 10 kHz-20 MHz.

Implementations can include one or more of the following. An ultrasound transducer may deliver the ultrasound energy. The filler material may include an adhesive, or may not include an adhesive. The filler material may include a plastic. The filler material may include a metal. The plurality of wood elements may be arranged, prior to the bonding the plurality of wood elements, in a proximity to one another. The applying the filler material to the plurality of wood elements and the delivering of the ultrasound energy to the plurality of wood elements may occur concurrently. The ultrasound energy may be delivered to the plurality of wood elements prior to the applying the filler material to the plurality of wood elements. The ultrasound energy may be delivered to the plurality of wood elements after the applying the filler material to the plurality of wood elements. The method may further include applying a compression force to the plurality of wood elements. The applying the compression force to the plurality of wood elements may occur prior to the delivering the ultrasound energy to the plurality of wood elements. The applying the compression force to the plurality of wood elements may occur concurrently with the delivering the ultrasound energy to the plurality of wood elements. The applying the compression force to the plurality of wood elements may occur after the delivering the ultrasound energy to the plurality of wood elements. The ultrasound energy may have a frequency within a frequency range of 15 kHz-1 MHz. The ultrasound energy may have a frequency within a frequency range of 20 kHz-100 kHz. The method may further include inspecting the composite wood product for a defect, where the inspecting includes delivering ultrasound energy to the composite wood product. The method may further include, prior to the applying the filler material, pretreating the plurality of wood elements, where the pretreating includes delivering ultrasound energy to the plurality of wood elements. The pretreating including delivering ultrasound energy to the plurality of wood elements may clean the plurality of wood elements. The method may further include, after the bonding into the composite wood product, applying a treatment to the composite wood product and delivering ultrasound energy to the composite wood product.

The details of one or more implementations are depicted in the associated drawings and the description thereof below. Certain implementations may provide one or more advantages. For example, implementations of the disclosed methods, devices and systems can be used to manufacture composite wood products that are stronger (e.g., one or more of higher tensile strength, higher compressive strength, higher shear strength) than composite wood products manufactured using traditional techniques. As another example, implementations of the disclosed methods, devices and systems can be used to manufacture composite wood products that have improved durability, as compared to composite wood products manufactured using traditional techniques. As yet another example, implementations of the disclosed methods, devices and systems can be used to manufacture composite wood products that have improved moisture resistance, as compared to composite wood products manufactured using traditional techniques. As yet another example, implementations of the disclosed methods, devices and systems can be used to manufacture composite wood products that have improved resistance to heat, as compared to composite wood products manufactured using traditional techniques. As yet another example, implementations of the disclosed methods, devices and systems can be used to manufacture composite wood products that have increased hardness, as compared to composite wood products manufactured using traditional techniques. As yet another example, implementations of the disclosed methods, devices and systems can be used to improve (e.g., expedite or speed up) the rate of curing or reduce the curing time in manufacturing composite wood products, as compared to the rate of curing or curing time of composite wood products manufactured using traditional techniques. As yet another example, implementations of the disclosed methods, devices and systems can be used to manufacture composite wood products that have improved resistance to insects or vermin, as compared to composite wood products manufactured using traditional techniques.

Other features, objects, and advantages of the technology described in this document will be apparent from the description and the drawings, and from the claims.

BRIEF DESCRIPTION OF THE DRAWINGS

FIG. 6A is a conceptual diagram of an example ultrasound transducer that includes an example cymbal-shaped horn that can be used for manufacturing composite wood products using ultrasound energy.

FIG. 6B is a conceptual diagram of an example ultrasound transducer that includes an example Langevin horn that can be used for manufacturing composite wood products using ultrasound energy.

FIG. 6C is a conceptual diagram of an example ultrasound transducer that includes an example ring-shaped horn that can be used for manufacturing composite wood products using ultrasound energy.

FIG. 6D is a conceptual diagram of an example ultrasound transducer that includes an example pyramid-shaped horn that can be used for manufacturing composite wood products using ultrasound energy.

FIG. 6E is a conceptual diagram of an example ultrasound transducer that includes an example sphere-shaped horn that can be used for manufacturing composite wood products using ultrasound energy.

FIG. 6F is a conceptual diagram of an example ultrasound transducer that includes an example dome-shaped horn that can be used for manufacturing composite wood products using ultrasound energy.

FIG. 6G is a conceptual diagram of an example ultrasound transducer that includes an example wedge-shaped horn that can be used for manufacturing composite wood products using ultrasound energy.

FIG. 6H is a conceptual diagram of an example ultrasound transducer that includes an example horn, generally shaped as a tube or a cylinder, which can be used for manufacturing composite wood products using ultrasound energy, where the horn includes an example chamber.

FIG. 12B is a conceptual diagram of another example ultrasound transducer that includes another example roller element.

FIG. 13A is a side view of an example roller element.

FIG. 13B is a side view of another example roller element.

FIG. 13C is a side view of yet another example roller element.

FIG. 15B is a block diagram of the example control module of FIG. 15A.

Like reference symbols in the various drawings indicate like elements.

DETAILED DESCRIPTION

Figure 1:
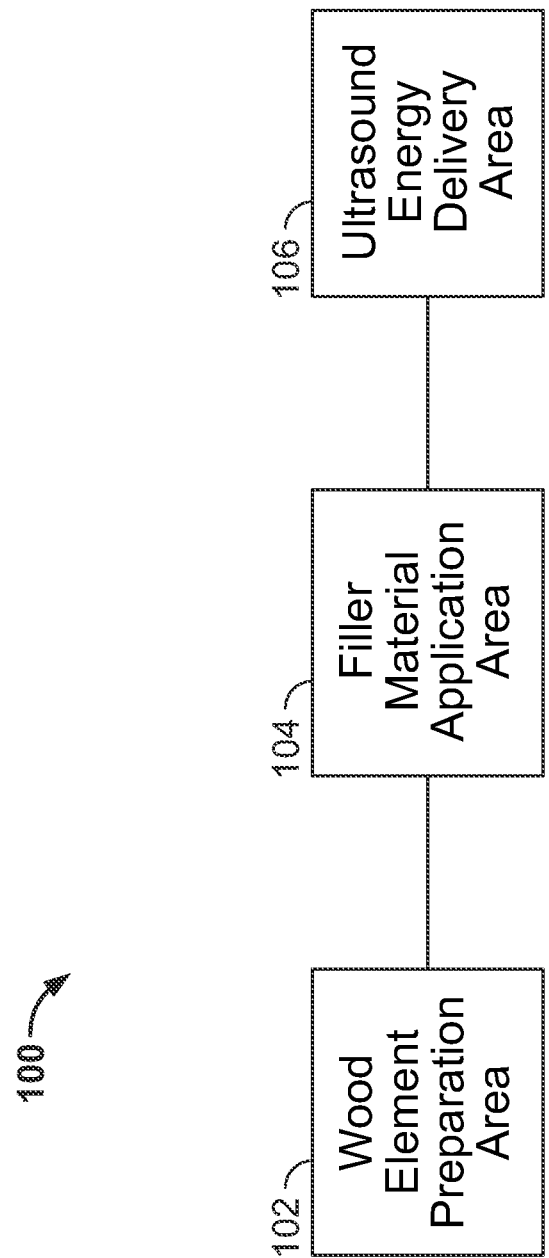
FIG. 1 is a block diagram of an example environment for manufacturing composite wood products using ultrasound energy.

Described herein are devices, systems and methods that can be used to bond wood or other plant products using ultrasound energy. With some implementations of the devices, systems and methods described herein, a composite wood product can be manufactured by applying a filler material to a plurality of wood elements and bonding the plurality of wood elements into a composite wood product, where the bonding comprises delivering low frequency ultrasound energy to the plurality of wood elements. For example, the low frequency ultrasound energy may have a frequency in the range of 10 kHz to 20 MHz. In some implementations, the low frequency ultrasound energy may have a frequency in the range of 15 kHz to 1 MHz. In some implementations, the low frequency ultrasound energy may have a frequency in the range of 20 kHz to 100 kHz.

An ultrasound transducer can be used to provide the ultrasound energy used in bonding the plurality of wood elements into the composite wood product. In various implementations, the ultrasound transducer produces ultrasound waves, which may convey the ultrasound energy to the plurality of wood elements and the filler material. In some examples, the ultrasound waves may be delivered as continuous waves, and in some examples the ultrasound waves may be delivered as pulsed waves. In some examples, the transducer can deliver periodic ultrasound waves, and the waves may include one or more of a variety of waveforms. For example, in various implementations, the waveforms may include one or more of sinusoidal waveforms, rectangular waveforms, square waveforms, trapezoidal waveforms, triangular waveforms, sawtooth waveforms, or other appropriate waveform shapes. The transducer may produce ultrasound waves that can include one or more of ultrasound longitudinal waves, ultrasound radial waves, and ultrasound shear waves, for example, where the ultrasound waves may deliver the ultrasound energy to the plurality of wood elements, to the filler material, or to both the plurality of wood elements and to the filler material.

The ultrasound energy may provide a mechanical stimulation to the plurality of wood elements. For example, as the ultrasound waves travel through a wood element or are absorbed by the wood element, the ultrasound waves may cause molecules within the wood element to vibrate. The vibration at the molecular level within the wood element may create friction between the vibrating molecules, which can generate heat within the wood element. Additionally, in some examples, as the ultrasound waves travel through or are absorbed by the wood element, the ultrasound waves may cause small or micro pressure differentials to be created within the wood element. Such pressure differentials can result in cavitation within the wood element, where micro-level gas or vapor bubbles may be created within the wood element as gas or vapor from higher-pressure areas within the wood element are forced or pushed, due to the pressure differentials, toward lower-pressure areas within the wood element. In one or more of these manners, the ultrasound energy may provide a mechanical stimulation in the bonding of wood or other plant products, for example. This mechanical stimulation may be provided, for example, even though the ultrasound transducer may not be in physical contact with the wood elements or with the filler material. In some examples, the ultrasound transducer, or a portion of the transducer, may be in physical contact with one or more of the wood elements, with the filler material, or with both the filler material and one or more of the wood elements, and the aforementioned mechanical stimulation may be provided.

The ultrasound energy may further provide a mechanical stimulation to the plurality of wood elements, which may be arranged in a proximity to one another, at a macro level. The mechanical stimulation provided by the ultrasound waves may cause one or more of the wood elements to move or vibrate, for example, and such movement or vibration may create friction between the wood elements. For example, the mechanical stimulation provided by the ultrasound waves may cause one or more of the wood elements to move or vibrate, and one or more surfaces of a first wood element may encounter resistance when moving, rubbing or vibrating in contact with one or more surfaces of one or more other wood elements (e.g., a second wood element, a second wood element and a third wood element, or one or more other wood elements). In one or more of these manners, the ultrasound energy may provide a mechanical stimulation in the bonding of wood or other plant products, for example. This mechanical stimulation may be provided, for example, even though the ultrasound transducer may not be in physical contact with the wood elements or with the filler material. In some examples, the ultrasound transducer, or a portion of the transducer, may be in physical contact with one or more of the wood elements, with the filler material, or with both the filler material and one or more of the wood elements, and the aforementioned mechanical stimulation may be provided.

Similarly, in various implementations the ultrasound waves may provide a mechanical stimulation to the filler material. For example, as the ultrasound waves travel through the filler material or are absorbed by the filler material, the ultrasound waves may cause molecules within the filler material to vibrate. The vibration at the molecular level within the filler material may create friction between the vibrating molecules, which can generate heat within the filler material. Additionally, in some examples, as the ultrasound waves travel through or are absorbed by the filler material, the ultrasound waves may cause small or micro pressure differentials to be created within the filler material. Such pressure differentials can result in cavitation within the filler material, where micro-level gas or vapor bubbles may be created within the filler material as gas or vapor from higher-pressure areas within the filler material are forced or pushed, due to the pressure differentials, to lower-pressure areas within the filler material. In one or more of these manners, the ultrasound energy may provide a mechanical stimulation in the bonding of wood or other plant products, for example. This mechanical stimulation may be provided, for example, even though the ultrasound transducer may not be in physical contact with the wood elements or with the filler material. In some examples, the ultrasound transducer, or a portion of the transducer, may be in physical contact with one or more of the wood elements, with the filler material, or with both the filler material and one or more of the wood elements, and the aforementioned mechanical stimulation may be provided.

The ultrasound energy may further provide a mechanical stimulation to the filler material at a macro level. For example, the mechanical stimulation provided by the ultrasound waves may agitate the filler material, and may cause the filler material to move, vibrate, diffuse, spread, flow, or penetrate, to list just a few examples. In one or more of these manners, the ultrasound energy may provide a mechanical stimulation in the bonding of wood or other plant products, for example. This mechanical stimulation may be provided, for example, even though the ultrasound transducer may not be in physical contact with the wood elements or with the filler material. In some examples, the ultrasound transducer, or a portion of the transducer, may be in physical contact with one or more of the wood elements, with the filler material, or with both the filler material and one or more of the wood elements, and the aforementioned mechanical stimulation may be provided.

In some implementations, the ultrasound energy may stimulate diffusion of the filler material, and may cause the filler material to penetrate into the wood elements, or deeper into the wood elements, for example. In some implementations, the ultrasound energy may stimulate diffusion of the filler material, and may cause the filler material to more broadly spread across, cover, or contact the wood elements, for example. In one or more of these manners, the ultrasound energy may provide a diffusional stimulation in the bonding of wood or other plant products. This diffusional stimulation may be provided, for example, even though the ultrasound transducer may not be in physical contact with the wood elements or with the filler material. In some examples, the ultrasound transducer, or a portion of the transducer, may be in physical contact with one or more of the wood elements, with the filler material, or with both the filler material and one or more of the wood elements, and the aforementioned diffusional stimulation may be provided.

The ultrasound energy may also provide a thermal stimulation to the plurality of wood elements, to the filler material, or to the plurality of wood elements and to the filler material, according to some implementations. This thermal stimulation may be in addition to any heat generated due to the mechanical stimulation or stimulations described above, for example. In some implementations, a temperature of the wood elements may increase as the wood elements absorb the ultrasound energy, or a portion of the ultrasound energy, that the transducer delivers to the wood elements. Similarly, a temperature of the filler material may increase as the filler material absorbs the ultrasound energy, or a portion of the ultrasound energy, that the transducer delivers to the filler material. The increase in temperature of the filler material, of the wood elements, or of both the filler material and the wood elements may stimulate better diffusion of the filler material in some examples, and may stimulate deeper penetration of the filler material into the wood elements, as by stimulating better flow of the filler material (e.g., in implementations where the filler material is a liquid or capable of flowing). In one or more of these manners, the ultrasound energy may provide a thermal stimulation in the bonding of wood or other plant products. This thermal stimulation may be provided, for example, even though the ultrasound transducer may not be in physical contact with the wood elements or with the filler material. In some examples, the ultrasound transducer, or a portion of the transducer, may be in physical contact with one or more of the wood elements, with the filler material, or with both the filler material and one or more of the wood elements, and the aforementioned thermal stimulation may be provided.

In some examples, friction generated between the wood elements or between the filler material and the wood elements due to the application of the ultrasound energy can cause the filler material to be pushed or driven into crevices, pores, gaps, spaces, voids, or cavities in one or more of the wood elements. In some implementations, the friction may stimulate atomization of the filler material (e.g., cause the filler material to be separated into smaller or finer particles), which can in some examples stimulate the filler material to be pushed or driven into crevices, pores, gaps, spaces, voids or cavities in one or more of the wood elements. In some examples, the friction may further generate heat, which may also stimulate a deeper penetration by the filler material into the wood elements, for example by heating the filler material and stimulating better flow of the filler material (e.g., in implementations where the filler material is a liquid or capable of flowing). In one or more of these manners, the ultrasound energy may generate friction between the wood elements or between the filler material and the wood elements, which may provide a stimulation in the bonding of wood or other plant products. This stimulation may be provided, for example, even though the ultrasound transducer may not be in physical contact with the wood elements or with the filler material. In some examples, the ultrasound transducer, or a portion of the transducer, may be in physical contact with one or more of the wood elements, with the filler material, or with both the filler material and one or more of the wood elements, and the aforementioned stimulation may be provided.

The filler material can, in various implementations, take a number of different forms. In some implementations, the filler material may include an adhesive, while in other implementations the filler material may not include an adhesive. In some implementations, the filler material may include a plastic, while in other implementations the filler material may not include a plastic. In some implementations, the filler material may include a metal, while in other implementations the filler material may not include a metal. Combinations of the foregoing are also possible (e.g., filler material includes an adhesive and a plastic; filler material includes an adhesive and a metal; or filler material includes an adhesive, plastic, and metal).

In some implementations, the filler material is a liquid. In some implementations, the filler material is a solid. For example, in some implementations the filler material may include a powder. In some implementations, the filler material is a gas. Combinations of the foregoing examples of states of the filler material or filler materials can also be used, according to some implementations. For example, in some implementations, the filler material may be a combination or a mixture of a liquid and a solid. In some implementations, the filler material may be a combination or a mixture of a liquid and a gas. In some implementations, the filler material may be a combination or a mixture of a solid and a gas. In some implementations, the filler material may be a combination or a mixture of a liquid, a solid, and a gas.

In some implementations, the filler material can be applied to the plurality of wood elements prior to delivering the ultrasound energy to the plurality of wood elements. In some implementations, the filler material can be applied to the plurality of wood elements concurrently with the delivering the ultrasound energy to the plurality of wood elements. In some implementations, the filler material can be applied to the plurality of wood elements after delivering the ultrasound energy to the plurality of wood elements.

In some implementations, ultrasound energy may be delivered to the plurality of wood elements both prior to the application of the filler material to the plurality of wood elements and concurrently with the application of the filler material to the plurality of wood elements. In some implementations, ultrasound energy may be delivered to the plurality of wood elements both concurrently with the application of the filler material to the plurality of wood elements and after the application of the filler material to the plurality of wood elements. In some implementations, ultrasound energy may be delivered to the plurality of wood elements both prior to the application of the filler material to the plurality of wood elements and after the application of the filler material to the plurality of wood elements. In some implementations, ultrasound energy may be delivered to the plurality of wood elements each of prior to the application of the filler material to the plurality of wood elements, concurrently with the application of the filler material to the plurality of wood elements, and after the application of the filler material to the plurality of wood elements.

In some implementations, a compression force may be applied to the plurality of wood elements, in addition to the delivery of the ultrasound energy to the plurality of wood elements. Many options are possible regarding the compression force, and many options are possible regarding when the compression force may be applied relative to the delivering of the ultrasound energy. In some examples, a press can be used to apply a physical compression force to the plurality of wood elements. In some implementations, the compression force can be applied to the plurality of wood elements concurrently with the delivering of the ultrasound energy to the plurality of wood elements. In some implementations, the compression force can be applied to the plurality of wood elements prior to the delivery of the ultrasound energy to the plurality of wood elements. In some implementations, the compression force can be applied to the plurality of wood elements after the delivery of the ultrasound energy to the plurality of wood elements. In some implementations, the compression force can beneficially aid in developing stronger bonds between the wood elements, for example.

Combinations of the foregoing examples of delivering ultrasound energy relative to application of a compression force to the plurality of wood products can also be used, according to some implementations. For example, in some implementations ultrasound energy may be delivered to the plurality of wood elements both prior to the application of the compression force to the plurality of wood elements and concurrently with the application of the compression force to the plurality of wood elements. In some implementations, ultrasound energy may be delivered to the plurality of wood elements both concurrently with the application of the compression force to the plurality of wood elements and after the application of the compression force to the plurality of wood elements. In some implementations, ultrasound energy may be delivered to the plurality of wood elements both prior to the application of the compression force to the plurality of wood elements and after the application of the compression force to the plurality of wood elements. In some implementations, ultrasound energy may be delivered to the plurality of wood elements each of prior to the application of the compression force to the plurality of wood elements, concurrently with the application of the compression force to the plurality of wood elements, and after the application of the compression force to the plurality of wood elements.

Some implementations of the devices, systems and methods described herein can be used to manufacture composite wood products that are stronger (e.g., one or more of higher tensile strength, higher compressive strength, higher shear strength) than composite wood products manufactured using traditional techniques, where ultrasound energy is not used. Some implementations of the devices, systems and methods described herein can be used to manufacture composite wood products that have improved durability, as compared to composite wood products manufactured using traditional techniques, where ultrasound energy is not used. Some implementations of the devices, systems and methods described herein can be used to manufacture composite wood products that have improved moisture resistance, as compared to composite wood products manufactured using traditional techniques, where ultrasound energy is not used. Improved moisture resistance can help to reduce or minimize degradation or decay of the composite wood products, for example. Some implementations of the devices, systems and methods described herein can be used to manufacture composite wood products that have improved resistance to heat, as compared to composite wood products manufactured using traditional techniques, where ultrasound energy is not used. Some implementations of the devices, systems and methods described herein can be used to manufacture composite wood products that have increased hardness, as compared to composite wood products manufactured using traditional techniques, where ultrasound energy is not used. Some implementations of the devices, systems and methods described herein can be used to improve (e.g., expedite or speed up) the rate of curing or reduce the curing time in manufacturing composite wood products, as compared to the rate of curing or curing time of composite wood products manufactured using traditional techniques, where ultrasound energy is not used. Some implementations of the devices, systems and methods described herein can be used to manufacture composite wood products that have improved resistance to insects or vermin, as compared to composite wood products manufactured using traditional techniques, where ultrasound energy is not used. Engineered wood products may be an environmentally friendly and desirable alternative to steel, for example because engineered wood products can be manufactured using renewable energy sources like fast growing trees, such as, without limitation, hybrid poplar, yellow poplar, aspen, Douglas fir, western hemlock, southern pine, or other appropriate hardwood or softwood species.

FIG. 1 is a block diagram of an example environment 100 for manufacturing composite wood products using ultrasound energy. In various implementations, examples of the composite wood products can include, without limitation, girders, beams, joists, I-joists, rafters, headers, studs, trusses, columns, rim boards, plywood, particle board, fibreboard, oriented strand board, flakeboard, waferboard, chipboard, laminated timber, laminated veneer lumber, cross-laminated timber, parallel strand lumber, laminated strand lumber, and finger joints.

The environment 100 includes a wood element preparation area 102, a filler material application area 104, and an ultrasound energy delivery area 106. The wood element preparation area 102 can be used to prepare a plurality of wood elements for applying filler material to the plurality wood elements and delivering ultrasound energy to the plurality of wood elements to bond the plurality of wood elements into a composite wood product. In some examples, the wood element preparation area 102 can be used to produce the wood elements, for example by cutting and processing timber or other wood- or plant-based components to produce the desired wood elements. In some examples, the wood elements can include primary products of such processing, and in some examples the wood elements can include secondary or waste products of such processing. Examples of such primary or secondary wood elements can include, without limitation, wood sheets, wood veneers, wood strips, wood strands, wood chips, wood flakes, wood scraps, sawdust, other appropriate lumber or timber particles, elements, components or products, or other appropriate plant-based particles, elements, components or products.

In some implementations, each of wood element preparation area 102, filler material application area 104 and ultrasound energy delivery area 106 may be located within one facility. In some implementations, one or more of wood element preparation area 102, filler material application area 104, and ultrasound energy delivery area 106 may be located within a facility different from one or more of the other areas 102, 104, 106. To list just one example, in some implementations wood element preparation area 102 may be located in a first facility, and filler material application area 104 and ultrasound energy delivery area 106 may be located in a second facility.

Within the wood element preparation area 102, a variety of processes can take place, in some cases depending on the type of wood elements desired. In some examples, timber can be debarked in the wood element preparation area 102. For example, debarking machinery may strip bark from the timber at this stage. In some examples, prior to debarking, the timber can be cut to appropriate lengths in the wood preparation area 102. In some examples, after debarking, the debarked timber can be cut to appropriate lengths in the wood preparation area 102. In some examples, the debarked timber can be soaked in a liquid bath (e.g., a water bath) or steamed with vapor (e.g., water vapor), for example to soften the wood fiber of the timber in the wood element preparation area 102. In some examples, the debarked timber is not subjected to a liquid bath or steam treatment.

In some examples, the debarked timber can be cut into sheets, veneers, strips, strands, chips, flakes, or other types of wood elements using, for example, a wood lathe, and in some examples one or more cutting apparatuses, such as various types of saws. In some examples, the one or more cutting apparatuses may cut to particular lengths, may cut to particular desired angles, may cut one or more grooves, or may make other specialized cuts, depending upon the particular implementation. In some examples, such cutting may produce wood scraps or sawdust that can also be used in some implementations. In some examples, one or more dryers can be used for one or more drying steps to reduce the moisture content of the wood sheets, veneers, strips, strands, chips, flakes, scraps, sawdust, or other types of wood elements, and in various implementations the one or more drying steps can occur before or after the cutting steps in the wood element preparation area 102.

Referring again to FIG. 1, before the wood elements are provided to the filler material application area 104, in some examples, the wood elements may be arranged in a proximity to one another within the wood element preparation area 102. There are many different ways that this can be done, some of which can involve the wood elements being arranged in a proximity to one another using one or more automated processes (e.g., using one or more machines to arrange), using one or more manual processes (e.g., using one or more workers manually arranging), or using a combination of one or more automated processes and one or more manual processes.

Figure 2:
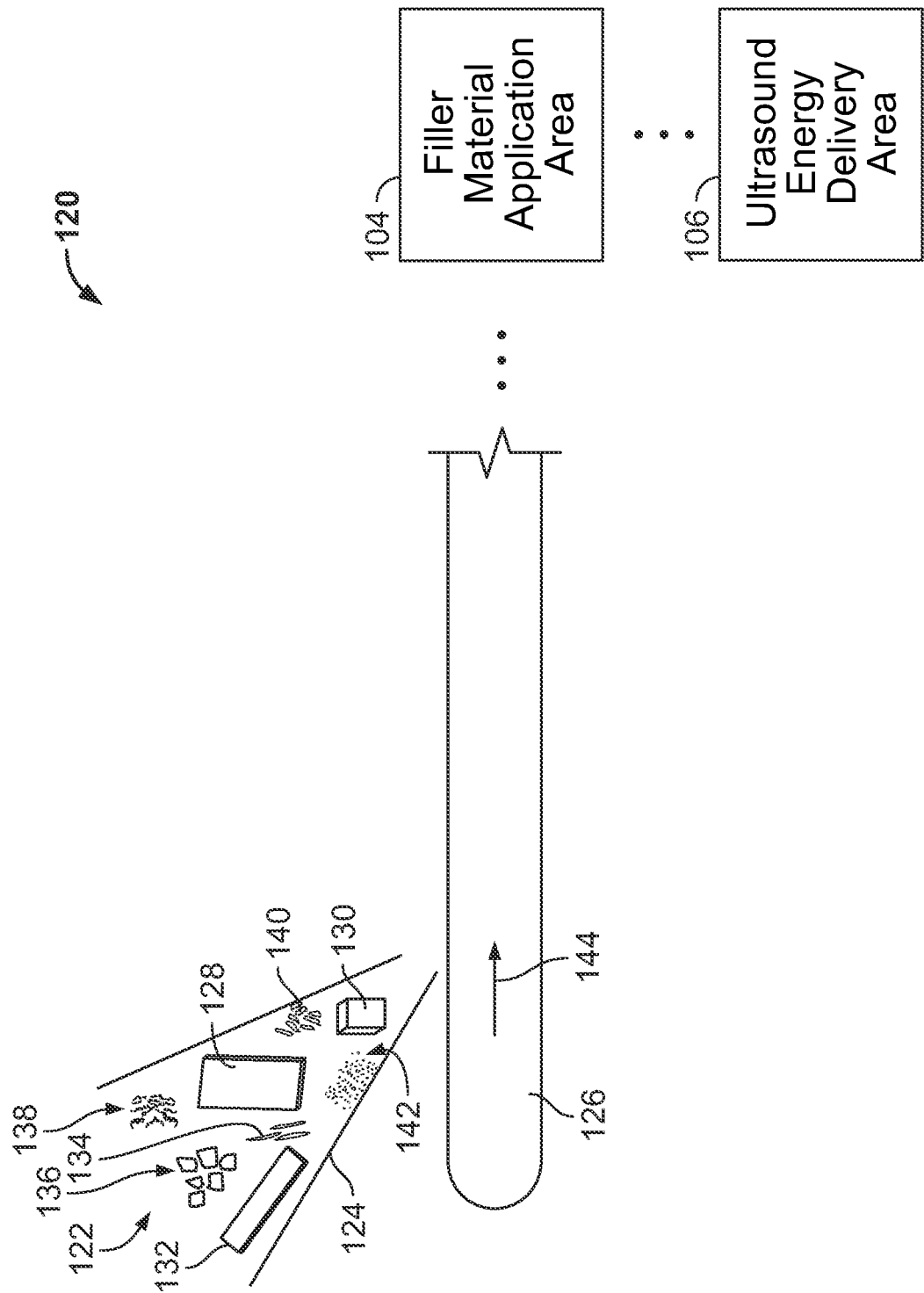
FIG. 2 is a conceptual diagram of example wood elements on or in an example funnel, to be deposited onto an example conveyor, as part of an example manufacturing process to produce composite wood products using ultrasound energy.

FIG. 2 is a conceptual diagram 120 of example wood elements 122 on or in an example funnel 124, to be deposited onto an example conveyor 126, as part of an example manufacturing process to produce composite wood products using ultrasound energy. The funnel 124 and conveyor 126 (or a portion of the conveyor 126) may be included in some implementations of the wood element preparation area 102, for example. In this illustrative example, the example wood elements 122 include a wood sheet 128, a wood veneer 130, a wood strip 132, a wood strand 134, wood chips 136, wood flakes 138, wood scraps 140, and sawdust 142. In some examples, other appropriate plant-based particles or plant-based elements, components or products could similarly be included, but are not shown in FIG. 2 for brevity. While multiple types of wood elements 128, 130, 132, 134, 136, 138, 140, 142 are shown together on the funnel 124 of FIG. 2 for illustrative purposes, in some examples only a single type of wood element (e.g., only wood sheets 128, or only wood strips 132, or any of the other depicted wood elements 130, 134, 136, 138, 140, 142, singularly) may be processed at a given time, and in such examples the funnel 124 may generally include only the particular type of wood element being processed at the time. In some examples, a subset of the depicted wood element types, such as any two of the wood element types, or any three (or more) of the wood element types, may be processed at a given time, and in such examples the funnel 124 may generally include those particular types of wood elements.

The conveyor 126 may take various forms. In some examples, the conveyor 126 can include one or more belts. In some examples, the conveyor 126 can include one or more rollers (e.g., a series of rollers). In some examples, the conveyor 126 can include one or more chains. Combinations of the foregoing conveyor examples are also possible. In general, conveyor 126 may transport the wood elements deposited from the funnel 124 onto the conveyor 126 in a direction 144 towards the filler material application area 104, according to some implementations. FIG. 2 shows the funnel 124 depositing the wood elements onto the conveyor 126, but in other examples the funnel 124 may not be used, and one or more machines may place the wood elements onto the conveyor 126. In yet other examples, wood elements may manually be placed onto the conveyor by workers, for example.

In some examples, conveyor 126 may include an arrangement feature or a stacking feature, to arrange or stack (or both) the wood elements into a particular configuration. In some examples, one or more machines or apparatuses (not shown in FIG. 2 for brevity) different from the conveyor 126 may arrange or stack (or both) the wood elements into a particular configuration. In some examples, one or more workers may manually arrange or stack (or both) the wood elements into a particular configuration. In some examples, a conveyor may not be used to transport wood elements to the filler material application area 104, to the ultrasound energy delivery area 106, or to transport wood elements within area 104 or area 106, for example.

The examples that follow will assume, for simplicity, that a single type of wood element is used in the filler material application area 104 and the ultrasound energy delivery area 106. In other examples, two or more (e.g., two, three, four, five, or more) types of wood elements can be used in the filler material application area 104 and the ultrasound energy delivery area 106 to manufacture composite wood products.

Figure 3A:
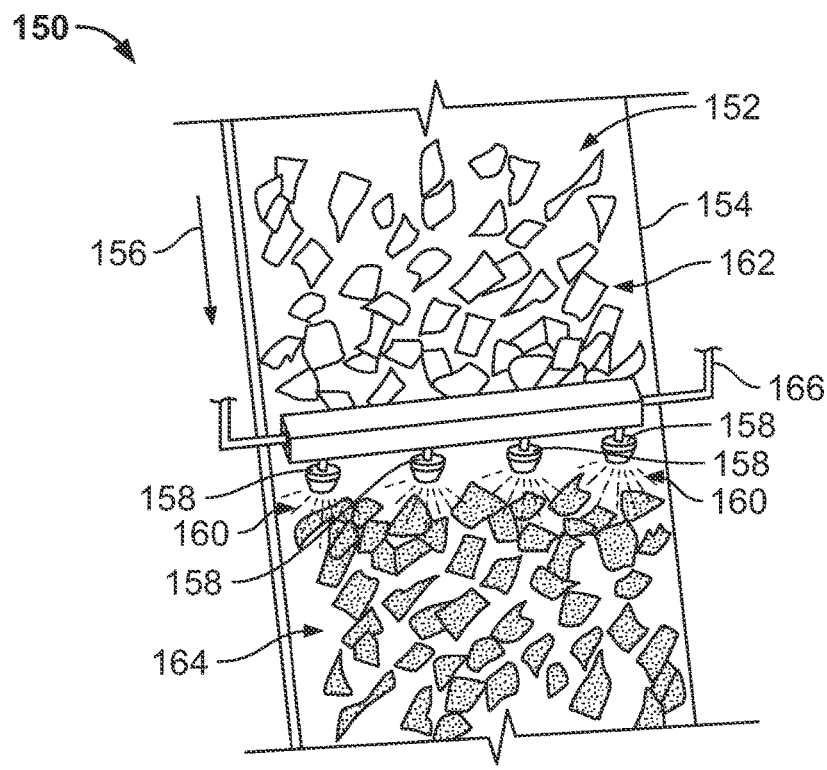
FIG. 3A is a view of an example application of filler material to a plurality of wood elements.

FIG. 3A is a view 150 of an example application of filler material to a plurality of wood elements. A plurality of wood elements 152 are arranged on a conveyor 154, and are travelling in a direction 156 based on movement of the conveyor 154. In this example, the depicted wood elements 152 are wood chips, but in other examples the wood elements may alternatively be wood sheets, wood veneers, wood strips, wood strands, wood flakes, wood scraps, sawdust, other appropriate lumber or timber particles, elements, components or products, or other appropriate plant-based particles, elements, components or products, or combinations of the foregoing. In some examples, conveyor 154 may correspond to conveyor 126 of FIG. 2, and in other examples conveyor 154 may be a different conveyor than conveyor 126 of FIG. 2.

Example applicators 158 are positioned, in this example, above the conveyor 154, and may dispense filler material 160 onto the wood elements 152 as the wood elements 152 pass under the applicators 158. In the example of FIG. 3A, the applicators 158 are spray nozzles, which may spray the filler material 160 onto the wood elements 152. In this example, the applicators 158 may not come into physical contact with the wood elements 152. In some examples, the filler material 160 includes an adhesive. In some implementations, the filler material 160 does not include an adhesive. In some implementations, the filler material 160 includes a plastic, and in some implementations the filler material 160 does not include a plastic. In some implementations, the filler material 160 includes a metal, and in other implementations the filler material 160 does not include a metal. As described above herein, combinations of such materials are also possible for the filler material 160.

As can be seen in FIG. 3A, in general, those wood elements 162 that have not yet passed under the applicators 158 have not yet had filler material 160 applied to the wood elements 162, while, in general, those wood elements 164 that have passed under the applicators 158 have had filler material 160 applied to the wood elements 164. Referring again to FIG. 1, the application of filler material shown in FIG. 3A may occur in filler material application area 104, for example. The view 150 depicts four spray nozzle applicators, but in other examples one, two, three, or five or more applicators 158 may alternatively be used to apply filler material 160 to the plurality of wood elements 152. The applicators 158 may be supplied filler material 160 by a filler material supply line 166, for example. In examples where the filler material 160 includes an adhesive, the applicators 158 may be individually or collectively considered an adhesive applicator, for example.

Figure 3B:
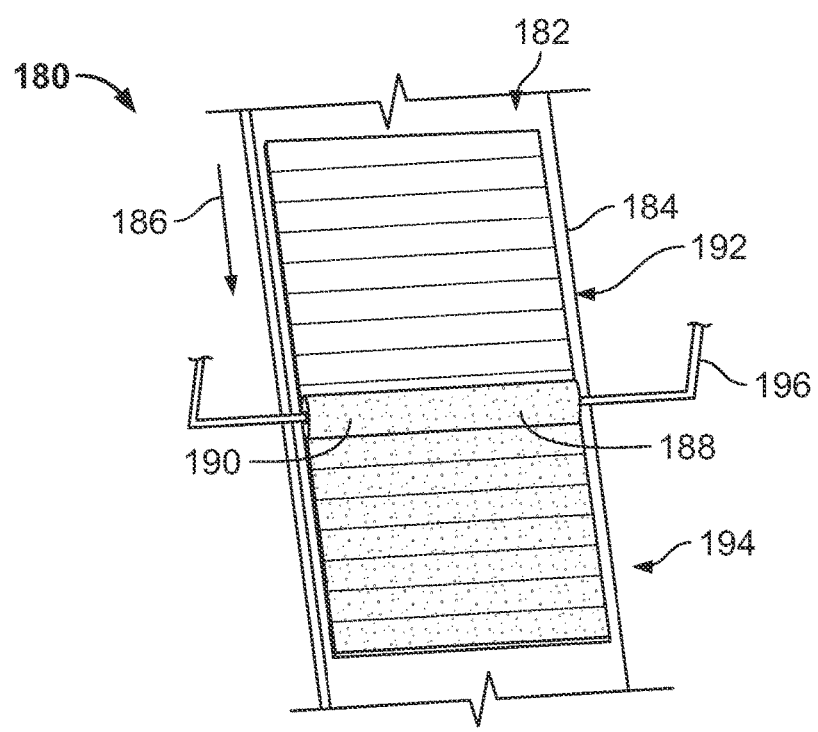
FIG. 3B is a view of another example application of filler material to a plurality of wood elements.

FIG. 3B is a view 180 of another example application of filler material to a plurality of wood elements. A plurality of wood elements 182 are arranged on a conveyor 184, and are travelling in a direction 186 based on movement of the conveyor 184. In this example, the depicted wood elements 182 are wood strips, but in other examples the wood elements may alternatively be wood sheets, wood veneers, wood chips, wood strands, wood flakes, wood scraps, sawdust, other appropriate lumber or timber particles, elements, components or products, or other appropriate plant-based particles, elements, components or products, or combinations of the foregoing. In some examples, conveyor 184 may correspond to conveyor 126 of FIG. 2, and in other examples conveyor 184 may be a different conveyor than conveyor 126 of FIG. 2.

An example applicator 188 is positioned, in this example, above the conveyor 184, and may dispense filler material 190 from the applicator 188 onto the wood elements 182 as the wood elements 182 pass under the applicator 188. In the example of FIG. 3B, the applicator 188 is a roller element, which may rotate about an axis and roll the filler material onto the wood elements 182. In this example, the applicator 188 may come into physical contact with the wood elements 182. In some examples, the filler material 190 includes an adhesive. In some implementations, the filler material 190 does not include an adhesive. In some implementations, the filler material 190 includes a plastic, and in some implementations the filler material 190 does not include a plastic. In some implementations, the filler material 190 includes a metal, and in other implementations the filler material 190 does not include a metal. As described above herein, combinations of such materials are also possible for the filler material 190. As can be seen in FIG. 3B, in general, those wood elements 192 that have not yet passed under the applicator 188 have not yet had filler material 190 applied to the wood elements 192, while, in general, those wood elements 194 that have passed under the applicator 188 have had filler material 190 applied to the wood elements 194. Referring again to FIG. 1, the application of filler material shown in FIG. 3B may occur in filler material application area 104, for example. The view 180 depicts a single applicator 188, but in other examples two or more applicators (e.g., two or more smaller rollers) may alternatively be used to apply filler material 190 to the plurality of wood elements 182. The applicator 188 may be supplied filler material 190 by a filler material supply line 196, for example. In examples where the filler material 190 includes an adhesive, the applicator 188 may be considered an adhesive applicator, for example.

Figure 3C:
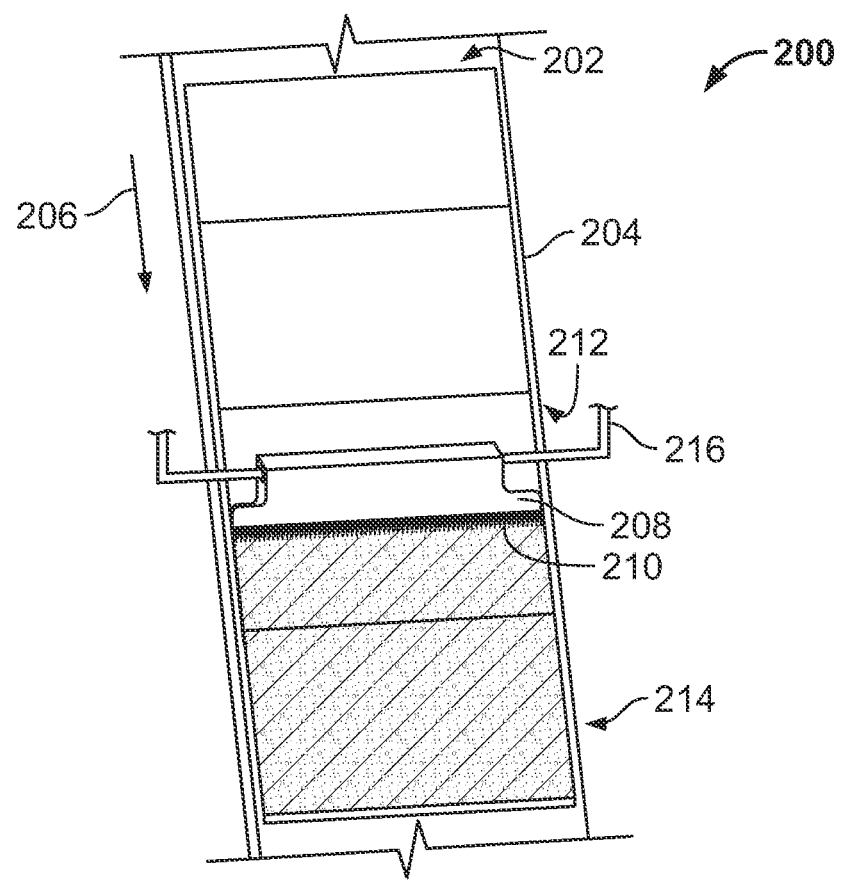
FIG. 3C is a view of yet another example application of filler material to a plurality of wood elements.

FIG. 3C is a view 200 of yet another example application of filler material to a plurality of wood elements. A plurality of wood elements 202 are arranged on a conveyor 204, and are travelling in a direction 206 based on movement of the conveyor 204. In this example, the depicted wood elements 202 are wood veneers, but in other examples the wood elements may alternatively be wood sheets, wood strips, wood strands, wood chips, wood flakes, wood scraps, sawdust, other appropriate lumber or timber particles, elements, components or products, or other appropriate plant-based particles, elements, components or products, or combinations of the foregoing. In some examples, conveyor 204 may correspond to conveyor 126 of FIG. 2, and in other examples conveyor 204 may be a different conveyor than conveyor 126 of FIG. 2.

An example applicator 208 is positioned, in this example, above the conveyor 204, and may dispense filler material 210 from the applicator 208 onto the wood elements 202 as the wood elements 202 pass under the applicator 208. In the example of FIG. 3C, the applicator 208 is one or more brush elements, which may brush the filler material 210 onto the wood elements 202. In this example, the applicator 208 may come into physical contact with the wood elements 202. In some examples, the filler material 210 includes an adhesive. In some implementations, the filler material 210 does not include an adhesive. In some implementations, the filler material 210 includes a plastic, and in some implementations the filler material 210 does not include a plastic. In some implementations, the filler material 210 includes a metal, and in other implementations the filler material 210 does not include a metal. As described above herein, combinations of such materials are also possible for the filler material 210. As can be seen in FIG. 3C, in general, those wood elements 212 that have not yet passed under the applicator 208 have not yet had filler material 210 applied to the wood elements 212, while, in general, those wood elements 214 that have passed under the applicator 208 have had filler material 210 applied to the wood elements 214. Referring again to FIG. 1, the application of filler material shown in FIG. 3C may occur in filler material application area 104, for example. The view 200 depicts a single applicator 208, but in other examples two or more applicators (e.g., two or more smaller brushes) may alternatively be used to apply filler material 210 to the plurality of wood elements 202. The applicator 208 may be supplied filler material 210 by a filler material supply line 216, for example. In examples where the filler material 210 includes an adhesive, the applicator 208 may be considered an adhesive applicator, for example.

Various examples of adhesives may be used as filler material 160, 190, 210, according to various implementations. Examples of adhesives that can be used as filler material can include, without limitation, urea-formaldehyde resins, phenol formaldehyde resins, melamine-formaldehyde resins, polyurethane resins, and polymeric methylene diphenyl diisocyanate resins. In some examples, an urethane adhesive or an acrylic urethane adhesive can be used. In some examples, a water-based adhesive can be used.

Following application of the filler material 160, 190, 210 in the examples of FIGS. 3A, 3B, and 3C, in some examples the plurality of wood elements 164, 194, 214 may be arranged in a proximity to one another. In some examples, wood elements may be arranged or stacked in a vertical dimension in a proximity to one another. For example, two or more of the wood strips 194 may be stacked vertically. As another example, two or more of the wood veneers 214 may be stacked vertically. In some examples, wood elements may be arranged or stacked in a horizontal or lateral dimension in a proximity to one another. Additional arrangements are possible, such as arrangements where some of the wood elements are arranged or stacked in a vertical dimension in a proximity to one another and some of the wood elements are arranged or stacked in a horizontal or lateral dimension in a proximity to one another.

In some examples, the arrangement of wood elements in proximity to one another may generally be structured or systematic (e.g., stacking two, three, four, five, or more wood elements in a vertical dimension, or vertically). In some examples the arrangement of wood elements in proximity to one another may generally be less structured, such as by randomly or variably arranging a plurality or wood elements (e.g., wood chips, wood flakes, wood scraps, sawdust, or the like) in proximity to one another. For example, the wood chips 164 may generally be randomly or variably arranged in a proximity to one another.

Arrangement of the plurality of wood elements in a proximity to one another may be performed using one or more automated processes (e.g., by one or more machines programmed to arrange the wood elements), using one or more manual processes (e.g., by one or more workers manually performing the wood element arrangement), or by a combination of one or more automated processes and one or more manual processes. In some examples, the plurality of wood elements may be arranged in a proximity to one another by being laid, or laid-up, in a "mat."

Figure 4:
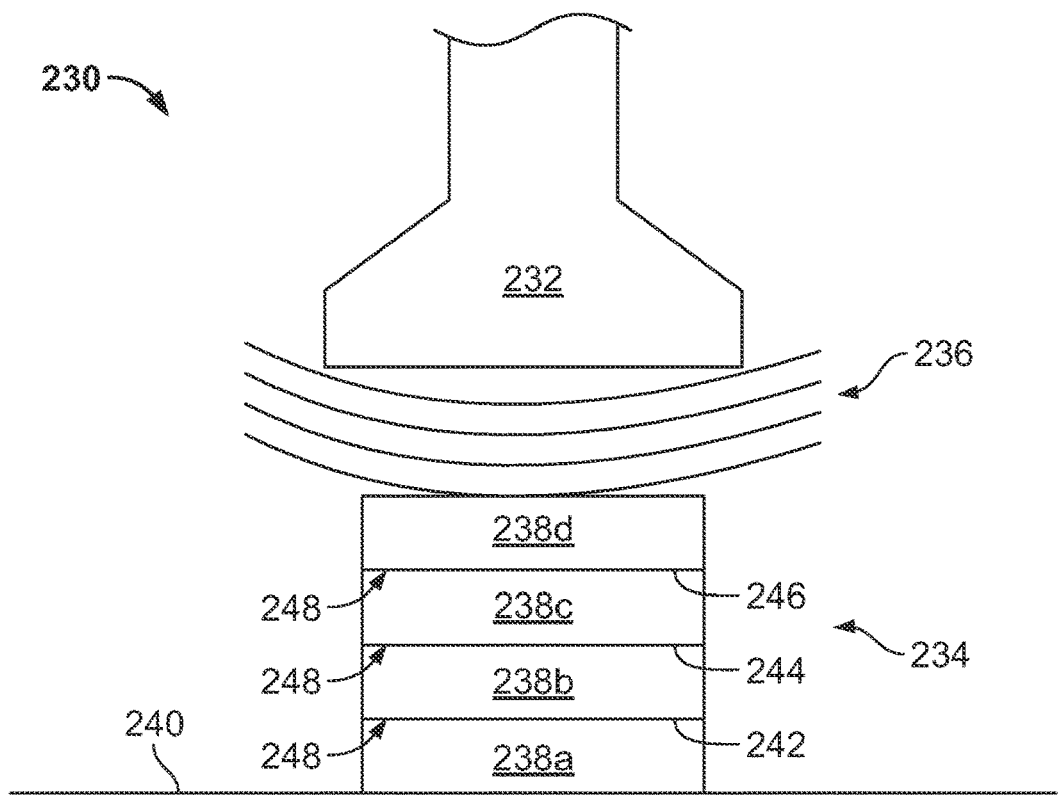
FIG. 4 is a conceptual diagram of an example ultrasound transducer delivering ultrasound energy to a plurality of example wood elements for manufacturing a composite wood product using ultrasound energy.

FIG. 4 is a conceptual diagram 230 of an example ultrasound transducer 232 delivering ultrasound energy to a plurality of example wood elements 234 for manufacturing a composite wood product using ultrasound energy. The delivery of ultrasound energy to the plurality of example wood elements 234 shown in FIG. 4 may occur in ultrasound energy delivery area 106 of FIG. 1, for example. Referring again to FIG. 4, the example ultrasound transducer 232 has a generic shape, and may represent any of the ultrasound transducer shapes or topologies discussed herein. In general, ultrasound transducer 232 may generate ultrasound energy, which can be used to bond the plurality of wood elements 234 into a composite wood product. For example, the ultrasound transducer 232 may produce ultrasound waves 236, which may convey the ultrasound energy to the plurality of wood elements 234. As used herein, the term "ultrasound transducer" will be understood to denote a device that may generate ultrasound energy, and may dispense the ultrasound energy from the ultrasound transducer in the form of ultrasound or ultrasonic waves. As used herein, the term "ultrasound transducer" does not necessarily denote that the device includes a receiver capable of receiving ultrasound waves (e.g., ultrasound waves reflected back to the device), and does not necessarily denote that the device is able to measure ultrasound waves. In some implementations of the devices, systems and methods discussed herein, ultrasound transducers can include a receiver that may receive, and in some implementations measure, ultrasound waves, but in the particular examples discussed herein, such receiver or receiver features are generally not included with the ultrasound transducers described with respect to the depicted examples herein.

In this example of FIG. 4, the plurality of wood elements 234 includes four wood elements 238a, 238b, 238c, and 238d arranged in a proximity to one another. In this example, the wood elements are generally stacked on top of one another, with a first wood element 238a generally disposed on a surface 240, a second wood element 238b generally arranged on top of the first wood element 238a, a third wood element 238c generally arranged on top of the second wood element 238b, and a fourth wood element 238d generally arranged on top of the third wood element 238c.

In some examples, one or more of the wood elements 238a, 238b, 238c, 238d may correspond to one or more of wood elements 194 or 192 of FIG. 3B. For example, one or more of the elements may include an applied filler material on a surface or portion of a surface, or on multiple surfaces. For example, filler material may be disposed on a top surface 242 of first wood element 238a; filler material may be disposed on a top surface 244 of second wood element 238b; and filler material may be disposed on a top surface 246 of third wood element 238c. Alternatively, for example, filler material may be disposed on bottom surfaces of wood elements 238b, 238c and 238d. In some examples, one or more of the wood elements 238a, 238b, 238c, 238d may correspond to wood elements 194 of FIG. 3B (e.g., elements 238a, 238b, 238c, each of which may have filler material disposed on their top surfaces 242, 244, 246, respectively), and one or more of the wood elements 238a, 238b, 238c, 238d may not correspond to the wood elements 194 of FIG. 3B (e.g., element 238d, which may not have filler material disposed on a surface of the element 238d prior to arrangement of the elements 238a, 238b, 238c, 238d in a proximity to one another). In some examples, filler material may not be disposed on any of the surfaces of the wood elements 238a, 238b, 238c, 238d. This example will assume that filler material 248 is disposed on surfaces 242, 244, and 246.

The plurality of wood elements 238a, 238b, 238c, 238d in this example may correspond to a plurality of wood strands. In other examples, the plurality of wood elements 238a, 238b, 238c, 238d may correspond to a plurality of wood sheets, a plurality of wood veneers, a plurality of wood strips, a plurality of wood chips, a plurality of wood flakes, a plurality of wood scraps, sawdust, an any combination of the foregoing, or other appropriate lumber or timber particles, elements, components or products, or other appropriate plant-based particles, elements, components or products.

In some examples, the ultrasound energy, conveyed by the ultrasound waves 236, has a frequency within a frequency range of 10 kHz-20 MHz. In some examples, the ultrasound energy, conveyed by the ultrasound waves 236, has a frequency within a frequency range of 15 kHz-1 MHz. In some examples, the ultrasound energy, conveyed by the ultrasound waves 236, has a frequency within a frequency range of 20 kHz-100 kHz. In general, the ultrasound transducer 232 may deliver low-frequency ultrasound energy to the plurality of wood elements 234.

In some examples, the ultrasound waves 236 may be delivered as continuous waves, and in some examples the ultrasound waves 236 may be delivered as pulsed waves. In some examples, the transducer 232 can deliver periodic ultrasound waves, and the waves may include one or more of a variety of waveforms. For example, in various implementations, the waveforms may include one or more of sinusoidal waveforms, rectangular waveforms, square waveforms, trapezoidal waveforms, triangular waveforms, sawtooth waveforms, or other appropriate waveform shapes, or appropriate combinations of the foregoing. The transducer 232 may produce ultrasound waves 236 that can include one or more of ultrasound longitudinal waves, ultrasound radial waves, and ultrasound shear waves, for example, where the ultrasound waves 236 may deliver the ultrasound energy to the plurality of wood elements 238a, 238b, 238c, 238d, to the filler material 248, or to both the plurality of wood elements 238a, 238b, 238c, 238d and to the filler material 248. For clarity, the ultrasound waves 236 depicted in FIG. 4 are shown emanating from the ultrasound transducer 232 and above the plurality of wood elements 234, but the ultrasound waves 236 may also impact, be absorbed by, or pass through one or more (e.g., two, three, or all) of the wood elements 238d, 238c, 238b, and 238a.

The delivered ultrasound energy may provide, in some examples, a mechanical stimulation to one or more of the plurality of wood elements 238a, 238b, 238c, 238d. For example, as the ultrasound waves 236 travel through a wood element or are absorbed by the wood element, the ultrasound waves 236 may cause molecules within the wood element to vibrate. The vibration at the molecular level within the wood element (e.g., element 238a, 238b, 238c, 238d) may create friction between the vibrating molecules, which can generate heat within the wood element. Additionally, in some examples, as the ultrasound waves 236 travel through or are absorbed by the wood element, the ultrasound waves 236 may cause small or micro pressure differentials to be created within the wood element. Such pressure differentials can result in cavitation within the wood element, where micro-level gas or vapor bubbles may be created within the wood element as gas or vapor from higher-pressure areas within the wood element are forced or pushed, due to the pressure differentials, toward lower-pressure areas within the wood element. In one or more of these manners, the ultrasound energy may provide a mechanical stimulation in the bonding of wood or other plant products, for example. This mechanical stimulation may be provided, for example, even though the ultrasound transducer 232 may not be in physical contact with the wood elements 238a, 238b, 238c, 238d or with the filler material 248. In some examples, the ultrasound transducer 232, or a portion of the transducer, may be in physical contact with one or more of the wood elements 238a, 238b, 238c, 238d, with the filler material 248, or with both the filler material 248 and one or more of the wood elements 238a, 238b, 238c, 238d, and the aforementioned mechanical stimulation may be provided.

The ultrasound energy may further provide a mechanical stimulation to one or more of the plurality of wood elements 238a, 238b, 238c, 238d at a macro level. For example, the mechanical stimulation provided by the ultrasound waves 236 may cause one or more of the wood elements to move or vibrate, for example, and such movement or vibration may create friction between wood elements. For example, a surface of one of the wood elements may encounter resistance when moving, rubbing or vibrating in contact with one or more surfaces of another of the wood elements. In one or more of these manners, the ultrasound energy may provide a mechanical stimulation in the bonding of wood or other plant products, for example. This mechanical stimulation may be provided, for example, even though the ultrasound transducer 232 may not be in physical contact with the wood elements 238a, 238b, 238c, 238d or with the filler material 248. In some examples, the ultrasound transducer 232, or a portion of the transducer, may be in physical contact with one or more of the wood elements 238a, 238b, 238c, 238d, with the filler material 248, or with both the filler material 248 and one or more of the wood elements 238a, 238b, 238c, 238d, and the aforementioned mechanical stimulation may be provided.

In some examples, the ultrasound waves 236 may provide a mechanical stimulation to the filler material 248. For example, as the ultrasound waves 236 travel through the filler material 248 or are absorbed by the filler material 248, the ultrasound waves 236 may cause molecules within the filler material 248 to vibrate. The vibration at the molecular level within the filler material 248 may create friction between the vibrating molecules, which can generate heat within the filler material 248. Additionally, in some examples, as the ultrasound waves 236 travel through or are absorbed by the filler material 248, the ultrasound waves may cause small or micro pressure differentials to be created within the filler material 248. Such pressure differentials can result in cavitation within the filler material 248, where micro-level gas or vapor bubbles may be created within the filler material 248 as gas or vapor from higher-pressure areas within the filler material 248 are forced or pushed, due to the pressure differentials, to lower-pressure areas within the filler material 248. In one or more of these manners, the ultrasound energy may provide a mechanical stimulation in the bonding of wood or other plant products, for example. This mechanical stimulation may be provided, for example, even though the ultrasound transducer 232 may not be in physical contact with the wood elements 238a, 238b, 238c, 238d or with the filler material 248. In some examples, the ultrasound transducer 232, or a portion of the transducer, may be in physical contact with one or more of the wood elements 238a, 238b, 238c, 238d, with the filler material 248, or with both the filler material 248 and one or more of the wood elements 238a, 238b, 238c, 238d, and the aforementioned mechanical stimulation may be provided.

The ultrasound energy may further provide, in some examples, a mechanical stimulation to the filler material 248 at a macro level. For example, the mechanical stimulation provided by the ultrasound waves 236 may agitate the filler material 248, and may cause the filler material 248 to move, vibrate, diffuse, spread, flow, or penetrate, to list just a few examples. In one or more of these manners, the ultrasound energy may provide a mechanical stimulation in the bonding of wood or other plant products, for example. This mechanical stimulation may be provided, for example, even though the ultrasound transducer 232 may not be in physical contact with the wood elements 238a, 238b, 238c, 238d or with the filler material 248. In some examples, the ultrasound transducer 232, or a portion of the transducer, may be in physical contact with one or more of the wood elements 238a, 238b, 238c, 238d, with the filler material 238, or with both the filler material 238 and one or more of the wood elements 238a, 238b, 238c, 238d, and the aforementioned mechanical stimulation may be provided.

In some examples, the ultrasound energy may stimulate diffusion of the filler material 248, and may cause the filler material 248 to penetrate into one or more of the wood elements 238a, 238b, 238c, 238d, or deeper into one or more of the wood elements, for example. In some implementations, the ultrasound energy may stimulate diffusion of the filler material 248, and may cause the filler material to more broadly spread across, cover, or contact one or more of the wood elements, for example. In one or more of these manners, the ultrasound energy may provide a diffusional stimulation in the bonding of wood or other plant products. This diffusional stimulation may be provided, for example, even though the ultrasound transducer 232 may not be in physical contact with the wood elements 238a, 238b, 238c, 238d or with the filler material 248. In some examples, the ultrasound transducer 232, or a portion of the transducer, may be in physical contact with one or more of the wood elements 238a, 238b, 238c, 238d, with the filler material 248, or with both the filler material 248 and one or more of the wood elements 238a, 238b, 238c, 238d, and the aforementioned diffusional stimulation may be provided.

The ultrasound energy may also, in some examples, provide a thermal stimulation to one or more of the plurality of wood elements 238a, 238b, 238c, 238d, to the filler material 248, or to the plurality of wood elements and to the filler material, according to some implementations. This thermal stimulation may be in addition to any heat generated due to the mechanical stimulation or stimulations described above, for example. In some implementations, a temperature of the one or more of the wood elements 238a, 238b, 238c, 238d may increase as the wood element absorbs the ultrasound energy, or a portion of the ultrasound energy. Similarly, a temperature of the filler material 248 may increase as the filler material 248 absorbs the ultrasound energy, or a portion of the ultrasound energy. The increase in temperature of the filler material, of the wood elements, or of both the filler material and one or more of the wood elements may stimulate better diffusion of the filler material 248 in some examples, and may stimulate deeper penetration of the filler material 248 into one or more of the wood elements 238a, 238b, 238c, 238d, as by stimulating better flow of the filler material 248 (e.g., in implementations where the filler material is a liquid or capable of flowing). In one or more of these manners, the ultrasound energy may provide a thermal stimulation in the bonding of wood or other plant products. This thermal stimulation may be provided, for example, even though the ultrasound transducer 232 may not be in physical contact with the wood elements 238a, 238b, 238c, 238d or with the filler material 248. In some examples, the ultrasound transducer 232, or a portion of the transducer, may be in physical contact with one or more of the wood elements 238a, 238b, 238c, 238d, with the filler material 248, or with both the filler material 248 and one or more of the wood elements 238a, 238b, 238c, 238d, and the aforementioned thermal stimulation may be provided.

In some examples, friction generated between the wood elements (e.g., between any of wood elements 238a, 238b, 238c, 238d) or between the filler material 248 and one or more wood elements due to the application of the ultrasound energy can cause the filler material 248 to be pushed or driven into crevices, pores, gaps, spaces, voids, or cavities in one or more of the wood elements 238a, 238b, 238c, 238d. In some implementations, the friction may stimulate atomization of the filler material 248 (e.g., cause the filler material 248 to be separated into smaller or finer particles), which can in some examples stimulate the filler material 248 to be pushed or driven into crevices, pores, gaps, spaces, voids or cavities in one or more of the wood elements. In some examples, the friction may further generate heat, which may also stimulate a deeper penetration by the filler material 248 into one or more of the wood elements, for example by heating the filler material 248 and stimulating better flow of the filler material 248 (e.g., in implementations where the filler material is a liquid or capable of flowing). In one or more of these manners, the ultrasound energy may generate friction between the one or more of the wood elements 238a, 238b, 238c, 238d or between the filler material 248 and the wood elements, which may provide a stimulation in the bonding of wood or other plant products. This stimulation may be provided, for example, even though the ultrasound transducer 232 may not be in physical contact with the wood elements 238a, 238b, 238c, 238d or with the filler material 248. In some examples, the ultrasound transducer 232, or a portion of the transducer, may be in physical contact with one or more of the wood elements 238a, 238b, 238c, 238d, with the filler material 248, or with both the filler material 248 and one or more of the wood elements 238a, 238b, 238c, 238d, and the aforementioned stimulation may be provided.

FIG. 4 depicts ultrasound transducer 232 delivering the ultrasound waves 236 from a location generally above the plurality of wood elements 238a, 238b, 238c, 238d, but in other examples the ultrasound transducer 232 may deliver the ultrasound waves 236 from a location that is generally lateral of (e.g., generally left or right of), ahead of (e.g., in front of as the wood elements approach), or behind the plurality of wood elements, or from a location that is generally below the plurality of wood elements 238a, 238b, 238c, 238d. In some examples, there may be two or more (e.g., two, three, four, five, six, or more) ultrasound transducers 232 that may concurrently or at different times deliver ultrasound waves to a plurality of wood elements. For example, some implementations may include two or more ultrasound transducers 232 that may concurrently deliver ultrasound waves to a plurality of wood elements from locations generally above the plurality of wood elements. As another example, some implementations may include two or more ultrasound transducers 232 that may concurrently deliver ultrasound waves to a plurality of wood elements from locations generally lateral of, ahead of, behind, or under the plurality of wood elements. As yet another example, some implementations may include one or more (e.g., one, two, three, or more) ultrasound transducers 232 that may concurrently deliver ultrasound waves to a plurality of wood elements from one or more locations generally above the plurality of wood elements, and also may include one or more (e.g., one, two, three, or more) ultrasound transducers 232 that may concurrently deliver ultrasound waves to a plurality of wood elements from one or more locations generally lateral of, ahead of, behind, or under the plurality of wood elements. Other combinations are also possible, as will be apparent to one of skill in the art.

Figure 5:
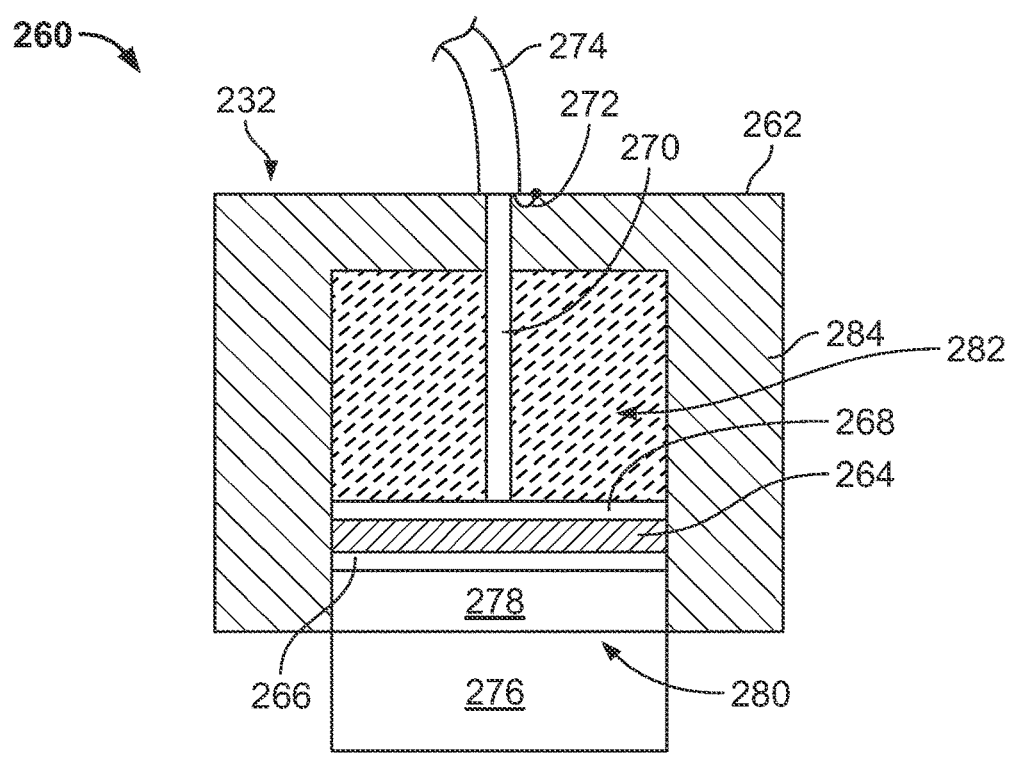
FIG. 5 is a conceptual diagram of the example ultrasound transducer of FIG. 4.

FIG. 5 is a conceptual diagram 260 of the example ultrasound transducer 232 of FIG. 4. The example ultrasound transducer 232 includes an example housing 262. Disposed within the housing 262 are one or more example ultrasound energy generation elements 264, which may be disposed, for example, between an example ground electrode 266 and an example positive electrode 268. In some examples, the one or more ultrasound energy generation elements 264 are one or more piezoelectric transducers. Piezoelectric transducers, such as one or more piezoelectric crystals or piezoelectric elements, for example, can utilize a piezoelectric property of the material to convert electric energy into mechanical energy. In some examples, the piezoelectric crystal or element may include a piezoelectric ceramic material. In some examples, the one or more ultrasound energy generation elements 264 are one or more magnetostrictive transducers. Magnetostrictive transducers, such as one or more coils of wire placed around one or more magnetostrictive materials, for example, can produce a mechanical energy based on a magnetostrictive property of the magnetostrictive materials and a magnetic field that can be provided by the wire and the magnetostrictive materials. Nickel, iron, and cobalt are a few examples of magnetostrictive materials.

The positive electrode 268 may be energized by an electrical conductor 270 that may carry a live electrical signal with respect to an electrical ground 272, and the ground electrode 266 may be electrically coupled to the electrical ground 272. In some examples, the housing 262 may also be electrically coupled to the electrical ground 272. In some examples, each of the electrical conductor 270 and the electrical ground 272 may be provided to the transducer 232 by a power cable 274.

The live electrical signal provided to the positive electrode 268 can cause an electrical current to flow between the positive electrode 268 and the ground electrode 266. As the electrical current flows between the positive electrode 268 and the ground electrode 266, the one or more ultrasound energy generation elements 264 may be excited by the electrical current, as described generally above, and may generate ultrasound waves.

The transducer 232 includes an example horn 276, sometimes also referred to as a sonotrode, which can direct the ultrasound waves toward a target for the ultrasound waves, such as a plurality of wood elements. In some examples, one or more example matching layers 278 may be included between the ground electrode 266 and an opening 280 defined in the housing 262. The one or more matching layers 278 may include materials that are conducive to achieving a better energy transfer of the ultrasound energy to the horn 276 and the target. Example materials that can be used for the one or more matching layers 278, for embodiments that include one or more matching layers 278, can include epoxy, polyurethane, polystyrene, and the like. One or more example backing layers 282, located on an opposite side of the positive electrode 268 from the one or more ultrasound energy generation elements 264, may prevent ultrasound waves from propagating in a direction away from the opening 280 in the housing 262. Additionally, an example acoustic insulation layer 284, which may be generally disposed between an internal surface of the housing 262 and the one or more backing layers 282, may provide acoustic insulation to prevent or limit the escape of ultrasound waves from the transducer 232 other than by the opening 280 via the horn 276.

In general, the ultrasound transducer 232 and horn 276 may have many different shapes and topologies, depending on the implementation. For example, some ultrasound transducers may include two or more (e.g., two, three, four, or more) openings 280 in a housing of the transducer, so that ultrasound waves generated by the transducer may impact one or more targets from more than one position or direction. Some ultrasound transducers can have two or more sets of ultrasound energy generation elements (e.g., piezoelectric elements, magnetostrictive elements, or combinations of the foregoing) and two or more sets of positive and ground electrodes, for example.

FIGS. 6A-6H are diagrams of various implementations of ultrasound transducers, and include a variety of horn configurations. FIG. 6A is a conceptual diagram 300 of an example ultrasound transducer 302 that includes an example cymbal-shaped horn 304 that can be used for manufacturing composite wood products using ultrasound energy. As with previously described transducers, the ultrasound transducer 302 may generate ultrasound waves 306, which may be directed towards a target 308 (e.g., a plurality of wood elements) via the horn 304. The cymbal-shaped horn 304 may in some examples be shaped similarly to the common percussion instrument. In some examples, the cymbal-shaped horn 304 may be shaped like a short cylinder, such as depicted in FIG. 6A. The horn 304 may define an opening 310 generally near a center of the horn 304, and the ultrasound waves 306 may emanate from the opening 310. The cymbal-shaped horn 304 may act as an acoustic waveguide, for example.

FIG. 6B is a conceptual diagram 320 of an example ultrasound transducer 322 that includes an example Langevin horn 324 that can be used for manufacturing composite wood products using ultrasound energy. The ultrasound transducer 322 may generate ultrasound waves 326, which may be directed towards a target 328 (e.g., a plurality of wood elements) via the horn 324. The Langevin horn 324 may define an opening 330, from which the ultrasound waves 326 may emanate. The Langevin horn 324 may act as an acoustic waveguide, for example.

FIG. 6C is a conceptual diagram 340 of an example ultrasound transducer 342 that includes an example ring-shaped horn 344 that can be used for manufacturing composite wood products using ultrasound energy. The ring-shaped horn 344 defines a plurality of openings 346 in the horn. The ultrasound transducer 342 may generate ultrasound waves 348, which may emanate from the plurality of openings 346 defined by the ring-shaped horn 344, and may be directed towards a target 350 (e.g., a plurality of wood elements) via the horn 344. The ring-shaped horn 344 may act as an acoustic waveguide, for example. In some examples, the plurality of openings 346 may be defined on an underside of the ring-shaped horn 344, for example for implementations where the ring-shaped horn 344 is generally located above the target. In some examples, the plurality of openings 346 may be defined on a top side of the ring-shaped horn 344, for example for implementations where the ring-shaped horn 344 is generally located under the target. In some examples, the plurality of openings 346 may be defined on an inward-facing surface of the ring-shaped horn 344, for example for implementations where the target, or a portion of the target, is located interior of a space defined by the ring-shaped horn 344. In some examples, openings 346 may be defined on a combination of the aforementioned ring-location possibilities.

FIG. 6D is a conceptual diagram 360 of an example ultrasound transducer 362 that includes an example pyramid-shaped horn 364 that can be used for manufacturing composite wood products using ultrasound energy. The ultrasound transducer 362 may generate ultrasound waves 366, which may be directed towards a target 368 (e.g., a plurality of wood elements) via the horn 364. In the depicted example of FIG. 6D, the pyramid-shaped horn 364 includes four sides, and the base of the pyramid has a square or rectangular shape. In various examples, the pyramid-shaped horn may have any appropriate number of sides (e.g., three, four, five, six, or more). The horn 364 may define an opening 370 generally near a center of the horn 364, and the ultrasound waves 366 may emanate from the opening 370. The pyramid-shaped horn 364 may act as an acoustic waveguide, for example.

FIG. 6E is a conceptual diagram 380 of an example ultrasound transducer 382 that includes an example sphere-shaped horn 384 that can be used for manufacturing composite wood products using ultrasound energy. The ultrasound transducer 382 may generate ultrasound waves 386, which may radiate from the sphere-shaped horn 384 and be directed towards a target 388 (e.g., a plurality of wood elements) via the horn 384. The sphere-shaped horn 384 may have any appropriate diameter. The sphere-shaped horn 384 may act as an acoustic waveguide, for example.

FIG. 6F is a conceptual diagram 400 of an example ultrasound transducer 402 that includes an example dome-shaped horn 404 that can be used for manufacturing composite wood products using ultrasound energy. The ultrasound transducer 402 may generate ultrasound waves 406, which may be directed towards a target 408 (e.g., a plurality of wood elements) via the horn 404. The horn 404 may define an opening 410 generally near a center of the horn 404, and the ultrasound waves 406 may emanate from the opening 410. The dome-shaped horn 404 may act as an acoustic waveguide, for example. Although not depicted in FIG. 6 for brevity, in some examples the dome-shaped horn 404 may be inverted with respect to its depicted orientation to the ultrasound transducer 402 in FIG. 6F. For example, in some implementations the horn may be shaped like a saucer or a cup.

FIG. 6G is a conceptual diagram 420 of an example ultrasound transducer 422 that includes an example wedge-shaped horn 424 that can be used for manufacturing composite wood products using ultrasound energy. The ultrasound transducer 422 may generate ultrasound waves 426, which may be directed towards a target 428 (e.g., a plurality of wood elements) via the horn 424. In the depicted example of FIG. 6G, the wedge-shaped horn 424 includes four sides, and the base of the wedge has a rectangular shape. In various examples, the wedge-shaped horn may have any appropriate number of sides (e.g., three, four, five, six, or more). The horn 424 may define a slot-shaped opening 430, and the ultrasound waves 426 may emanate from the opening 430. The wedge-shaped horn 424 may act as an acoustic waveguide, for example.

FIG. 6H is a conceptual diagram 440 of an example ultrasound transducer 442 that includes an example horn 444, generally shaped as a tube or a cylinder in FIG. 6H, that can be used for manufacturing composite wood products using ultrasound energy, where the horn 444 includes an example chamber 446. In various examples, the chamber 446 may define a space within the horn 444 where various elements or materials, after being introduced to the chamber 446, may be sonicated within the horn 444, for example. The chamber 446 may have any appropriate number of input channels, which may be used to feed elements or materials into the chamber 446, for example. Chamber 446 includes two input channels: an example first input channel 448 (labeled "Input A" in FIG. 6H) and an example second input channel 450 (labeled "Input B" in FIG. 6H); in other examples the chamber 446 may include one, three, four, or more input channels. Examples of elements or materials that may be introduced via an input channel to the chamber 446 can include one or more types of wood elements, one or more types of filler material (e.g., any of the types of filler material discussed herein), or combinations of the foregoing, to list just a few examples.

In some examples, a plurality of wood elements 452 (e.g., sawdust, wood flakes, wood chips, wood scraps, or the like) may be input to the chamber 446 via, for example, the first input channel 448, and a filler material 454 may be input to the chamber 446 via the second input channel 450. The plurality of wood elements 452 and the filler material 454 may be impacted by ultrasound waves 456 within the chamber 446, where the ultrasound waves 456 are generated by the ultrasound transducer 442. In some examples, the filler material 454 may adhere to or coat the plurality of wood elements 452 within the chamber 446, and the ultrasound waves 456 within the chamber 446 may provide one or more of mechanically stimulating and thermally stimulating the plurality of wood elements 452 and the filler material 454 within the chamber 446, and may also stimulate diffusion of the filler material 454 onto and into the wood elements 452, for example, as described above with reference to beneficial impacts that ultrasound may have.

The wood elements 452 and filler material 454 may be extruded from the horn 444 and may be directed towards a target 458 (e.g., a plurality of wood elements). Ultrasound waves 460, generated by the ultrasound transducer 442, may also be directed toward the target 458 via the horn 444. The horn 444 may act as an acoustic waveguide, for example.

While FIG. 6H depicts the horn 444 as having a tubular or cylindrical shape, any of the horn shapes discussed herein may also include a chamber similar to chamber 446, through which various elements or materials may pass and may be sonicated as they pass through the chamber. In some examples, a horn and chamber may be sized to accommodate larger wood elements, such as one or more of wood strips, wood strands, wood veneers, and wood sheets, for example.

In some examples, any of the ultrasound transducers discussed herein may similarly include a chamber through which elements or materials may pass and be sonicated, in some examples without using a horn. In some examples, a horn can also be used with a transducer that includes a chamber for sonicating elements or materials within the transducer chamber.

Figure 7:
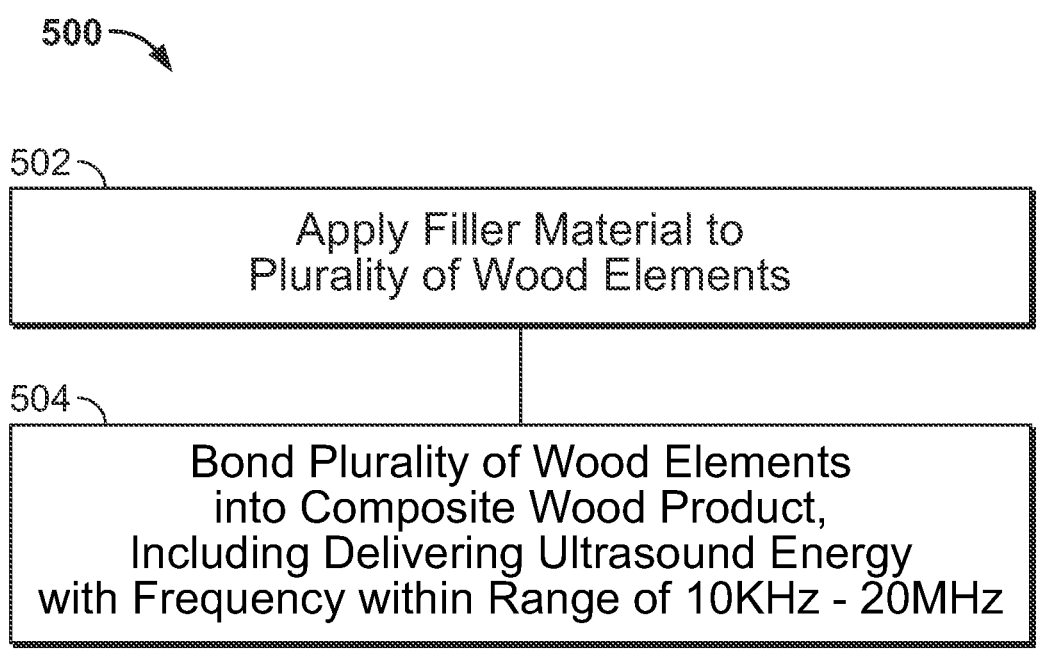
FIG. 7 is a flowchart of an example method that can be used to manufacture a composite wood product.

FIG. 7 is a flowchart 500 of an example method that can be used to manufacture a composite wood product. At a first step 502, a filler material is applied to a plurality of wood elements. The filler material may be applied by one or more applicators, such as any of the applicators 158, 188, 208 shown in FIGS. 3A, 3B, and 3C, for example, or any of the other examples of applicators described herein. In some implementations, the filler material may include an adhesive. In some implementations, the filler material may not include an adhesive. In some implementations, the filler material may include a plastic, while in other implementations the filler material may not include a plastic. In some implementations, the filler material may include a metal, while in other implementations the filler material may not include a metal. Combinations of the foregoing are also possible (e.g., filler material includes an adhesive and a plastic; filler material includes an adhesive and a metal; or filler material includes an adhesive, plastic, and metal). In some implementations, the filler material may be a liquid. In some implementations, the filler material may be a solid. In some implementations, the filler material may be a gas. Combinations of the foregoing examples of states of the filler material or filler materials can also be used, according to some implementations. For example, in some implementations, the filler material may be a combination or a mixture of a liquid and a solid. In some implementations, the filler material may be a combination or a mixture of a liquid and a gas. In some implementations, the filler material may be a combination or a mixture of a solid and a gas. In some implementations, the filler material may be a combination or a mixture of a liquid, a solid, and a gas.

At step 504, the plurality of wood elements are bonded into a composite wood product, including delivering ultrasound energy with a frequency within a range of 10 kHz-20 MHz to the plurality of wood elements. The ultrasound energy may be delivered to the plurality of wood elements by one or more ultrasound transducers, such as the ultrasound transducer 232 of FIG. 4, for example, or any of the other examples of ultrasound transducers described herein. In some examples, the ultrasound energy delivered to the plurality of wood elements may have a frequency within a range of 15 kHz-1 MHz. In some examples, the ultrasound energy delivered to the plurality of wood elements may have a frequency within a range of 20 kHz-100 kHz. In some examples, prior to the bonding of the plurality of wood elements, the plurality of wood elements may be arranged in a proximity to one another.

In some examples, the filler material is applied to the plurality of wood elements prior to the delivery of the ultrasound energy to the plurality of wood elements. In some examples, the filler material is applied to the plurality of wood elements concurrently with the delivery of the ultrasound energy to the plurality of wood elements. In some examples, the ultrasound energy is delivered to the plurality of wood elements prior to the application of the filler material to the plurality of wood elements.

Figure 8:
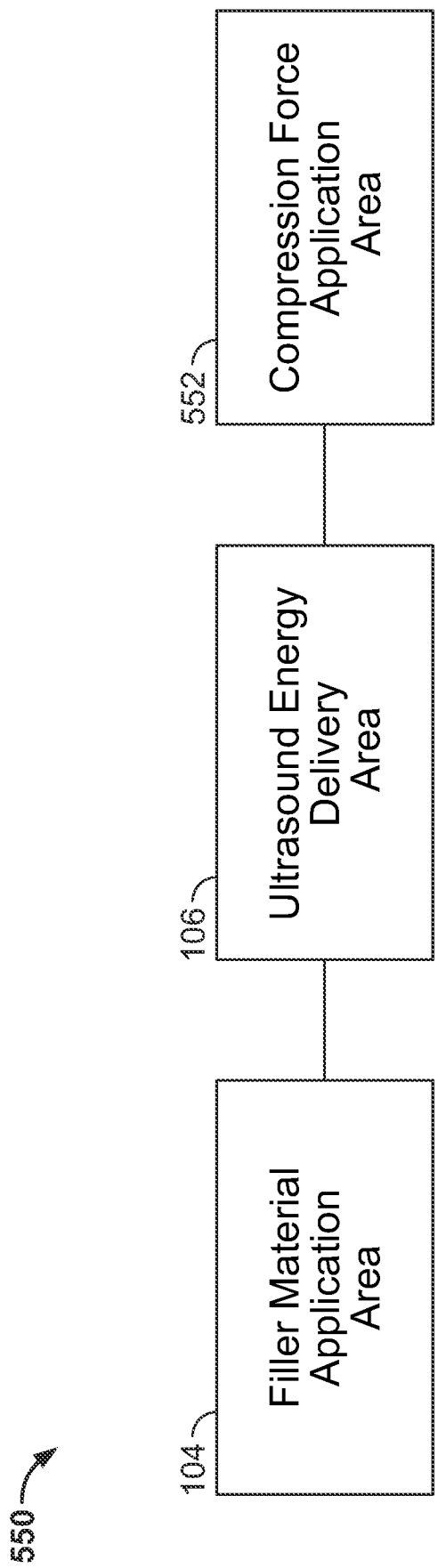
FIG. 8 is a block diagram of an example environment for manufacturing composite wood products using ultrasound energy.

FIG. 8 is a block diagram of an example environment 550 for manufacturing composite wood products using ultrasound energy. In various implementations, examples of the composite wood products can include, without limitation, girders, beams, joists, I-joists, rafters, headers, studs, trusses, columns, rim boards, plywood, particle board, fibreboard, oriented strand board, flakeboard, waferboard, chipboard, laminated timber, laminated veneer lumber, cross-laminated timber, parallel strand lumber, laminated strand lumber, and finger joints. The environment 550 includes the filler material application area 104 and the ultrasound energy delivery area 106, each described above with reference to FIG. 1 and other figures, and includes a compression force application area 552. Although not shown in FIG. 8 for brevity, it will be understood that in some implementations the wood element preparation area 102 of FIG. 1 may also be included in environment 550.

Figure 9:
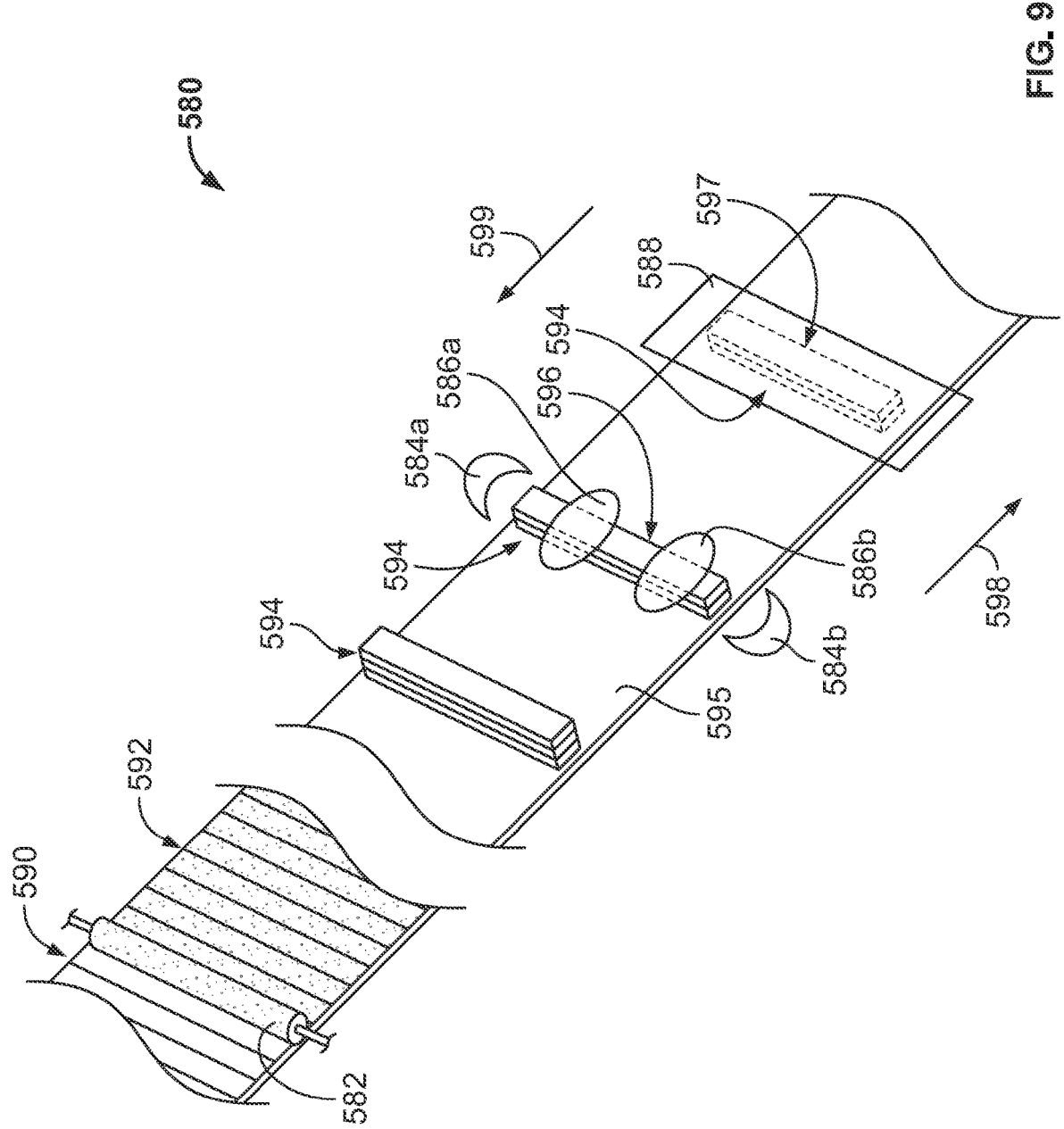
FIG. 9 is a conceptual diagram of an example environment for manufacturing composite wood products using ultrasound energy.

The compression force application area 552 can be used to apply a compressive force to the plurality of wood elements. In some examples, a press can be used to apply a physical compression force to the plurality of wood elements. FIG. 9 is a conceptual diagram of an example environment 580 for manufacturing composite wood products using ultrasound energy. The environment 580 includes an example filler material applicator 582, example ultrasound transducers 584a, 584b, 586a, 586b and an example press 588. Filler material applicator 582 can apply a filler material to a plurality of wood elements 590, in a manner similar to that described above with reference to applicator 188 of FIG. 3B. In the depicted example of FIG. 9, the applicator 582 is a roller element, but any of the other types of applicators (e.g., one or more spray nozzles, brushes, rollers, or other types of applicators) described herein may alternatively be used.

A plurality of wood elements 594 may be arranged in proximity to one another. For example, a plurality of wood elements 594 may be stacked vertically, as described herein above, or may be arranged in any appropriate manner. In some examples, the plurality of wood elements 594 includes one or more elements 592 that have had filler material applied thereto by applicator 582. In some examples, the plurality of wood elements 594 includes one or more wood elements 592 that have had filler material applied thereto, and one or more wood elements that have not had filler material applied thereto. And in some examples, the plurality of wood elements 594 do not include filler material.

One or more ultrasound transducers may deliver ultrasound energy to the plurality of wood elements 594. In the example of FIG. 9, ultrasound transducers 584a and 584b are disposed laterally of a conveyor 595, on which the plurality of wood elements 594 may be transported, and laterally of the plurality of wood elements when the plurality of wood elements are positioned in a target position 596 to receive ultrasound energy. A first ultrasound transducer 584a is located to the left of the conveyor 595, and a second ultrasound transducer 584b is located to the right of the conveyor 595. Additionally, in this example, ultrasound transducers 586a and 586b are disposed above the conveyor 595, and above the plurality of wood elements 594 when the plurality of wood elements are positioned in the target position 596 to receive ultrasound energy. In this example, the conveyor 595 may move the plurality of wood elements 594 into the target position 596 with respect to the ultrasound transducers, and the ultrasound transducers 584a and 584b may deliver ultrasound energy to the plurality of wood elements 594 from positions laterally left and laterally right of the wood elements, respectively, in rightward and leftward directions, respectively. Similarly, the ultrasound transducers 586a and 586b may deliver ultrasound energy to the plurality of wood elements 594 from above, in a downward direction.

In other examples, additional ultrasound transducers (e.g., five, six, seven, eight, or more), or fewer ultrasound transducers (e.g., one, two, or three) may be used. In some examples, ultrasound energy may be provided from only one direction (e.g., only in a downward direction, from one or more ultrasound transducers generally above the plurality of wood elements, or in any other direction), and in these examples, more or fewer ultrasound transducers may be used than are shown in FIG. 9 (e.g., transducers 584a and 584b may not be used). In some examples, ultrasound energy may be provided from two directions (e.g., in a downward direction, and in a first lateral direction, or in upward and downward directions, or in left and right directions, or any other combination), and in these examples, more or fewer ultrasound transducers may be used than are shown in FIG. 9. In the example of FIG. 9, ultrasound energy is provided generally from three directions: in a downward direction from above (e.g., from ultrasound transducers 586a and 586b), in a first lateral direction (e.g., from ultrasound transducer 584a), and in a second lateral direction (from ultrasound transducer 584b). In some examples, ultrasound energy may be delivered to the plurality of wood elements from more than three directions (e.g., four, five, six, or more directions). For example, additional ultrasound transducers (not shown in FIG. 9 for brevity) may be provided to deliver ultrasound energy to the wood elements in a rearward direction (e.g., from a position ahead of, or in front of, the wood elements), in a forward direction (e.g., from a position trailing, or behind, the wood elements), or in an upward direction (e.g., from a position below, or beneath, the wood elements). Of course, any of these alternative ultrasound transducer locations or configurations may also be utilized in a system that delivers ultrasound energy to the plurality of wood elements from a single direction, from two directions, from three directions, or from more than three directions.

In some examples, one or more of the depicted ultrasound transducers 584a, 584b, 586a, 586b may be moved or repositioned to deliver ultrasound energy to the wood elements from one or more of these other directions or positions, according to some implementations. While the ultrasound transducers discussed above with reference to FIG. 9 are depicted in the environment 580 that includes the press 588, it will be understood that any of the ultrasound transducers, or configurations, described with reference to FIG. 9 or elsewhere herein may be used in implementations that do not include a press, or in implementations that do not include a compression force application area.

In some examples, the conveyor 595 may stop for a period of time while the ultrasound transducers deliver the ultrasound energy to the plurality of wood elements 594. In some examples, the conveyor 595 may continue to move while the ultrasound transducers deliver the ultrasound energy to the plurality of wood elements 594. In some examples, a speed of the conveyor 595 may be adjusted (e.g., slowed down) for a period of time while the ultrasound transducers deliver the ultrasound energy to the plurality of wood elements 594. In some examples, one or more of the ultrasound transducers may be generally stationary with respect to the movement of the conveyor 595. In some examples, one or more of the ultrasound transducers can be configured to move, for example to move with respect to the conveyor 595, to move with respect to the target position 596, or to move with respect to the plurality of wood elements 594.

The press 588 may deliver one or more compressive forces to the plurality of wood elements 594. In some examples, the press 588 may deliver a downward compressive force to the plurality of wood elements 594. In some examples, the press 588 may deliver one or more lateral compressive forces (e.g., a compressive force from the left, a compressive force from the right, or compressive forces from both the left and the right). In some examples, the press 588 may deliver a compressive force from the front of the plurality of wood elements 594, from the rear of the plurality of wood elements 594, or from both the front and the rear of the plurality of wood elements 594. Combinations of such applied compressive forces are also possible. For example, according to some implementations the press 588 may deliver a downward compressive force to the plurality of wood elements 588, and one or more additional compressive forces (e.g. a compressive force from the left, from the right, from both the left and the right, from the front, from the back, from both the front and the back, from each of the left, right, front, and back, or others). In some examples, the press 588 may be generally stationary with respect to the movement of the conveyor 595. In some examples, the press 588 can be configured to move with respect to the conveyor 595, to move with respect to a target position 597 to receive a compression force for the wood elements, or to move with respect to the plurality of wood elements 594.

In some examples, ultrasound energy may be delivered to the plurality of wood elements, and thereafter a compressive force may be applied to the plurality of wood elements. For example, according to some implementations the conveyor 595 may generally move in a first direction 598, and the one or more ultrasound transducers (transducers 584a, 584b, 586a, 586b in the example of FIG. 9) may deliver ultrasound energy to the plurality of wood elements prior to the one or more presses (e.g., press 588 in the example of FIG. 9) delivering one or more compressive forces to the plurality of wood elements. In some examples, one or more compressive forces may be applied to the plurality of wood elements, and thereafter ultrasound energy may be delivered to the plurality of wood elements. For example, according to some implementations the conveyor 595 may generally move in a second direction 599, and the one or more presses (e.g., press 588 in the example of FIG. 9) may apply one or more compressive forces to the plurality of wood elements prior to the one or more ultrasound transducers (e.g., transducers 584a, 584b, 586a, 586b in the example of FIG. 9) delivering ultrasound energy to the plurality of wood elements. Filler material may be applied to the plurality of wood elements prior to applying the compressive force and delivering the ultrasound energy in each of the preceding two examples, according to some implementations.

Figure 10A:
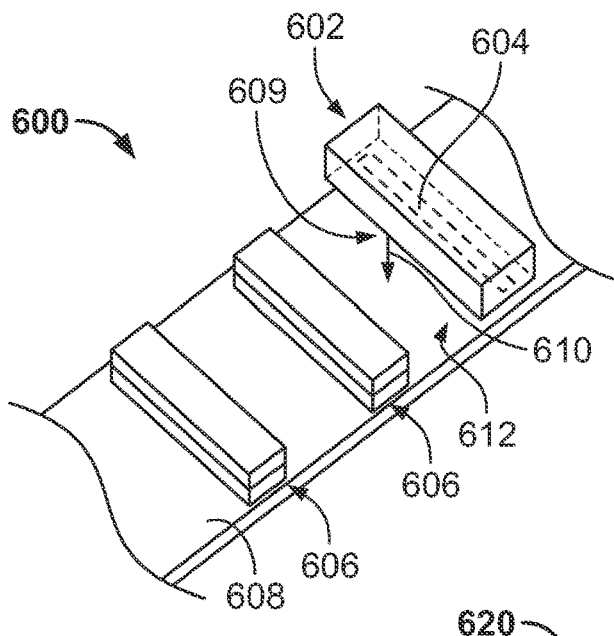
FIG. 10A is a conceptual diagram of an example press and an example ultrasound transducer that is integral with the press, and that can be used for manufacturing composite wood products using ultrasound energy.

In some examples, one or more ultrasound transducers can be integral with the press, and can deliver ultrasound energy to the plurality of wood elements concurrently with (or prior to, after, or a combination of the foregoing, depending on the implementation) the press delivering one or more compressive forces to the plurality of wood elements. FIG. 10A is a conceptual diagram 600 of an example press 602 and an example ultrasound transducer 604 that is integral with the press 602, and that can be used for manufacturing composite wood products using ultrasound energy. The ultrasound transducer 604 and the press 602 may respectively, in some implementations, concurrently deliver ultrasound energy and a compressive force to a plurality of wood elements 606. The example of FIG. 10A shows wood elements 606 (two wood veneers stacked vertically in this example, but any of the wood elements discussed herein could alternatively be used) on a conveyor 608, which may move the plurality of wood elements 606 into a target position 609 beneath the press 602 and ultrasound transducer 604.

The press 602 may apply a downward compressive force 610 to the plurality of wood elements 606 when the wood elements 606 are in the target position 609, and the ultrasound transducer 604 may concurrently deliver ultrasound energy to the plurality of wood elements. The press 602 includes a surface 612 that can apply the force 610 to the plurality of wood elements 606. In some examples, the ultrasound transducer 604 can be arranged flush with the surface 612 of the press 602 that can apply the compressive force 610 to the plurality of wood elements 606. In some examples, the ultrasound transducer 604 can be arranged to be recessed with respect to the surface 612 of the press 602 that can apply the compressive force 610 to the plurality of wood elements 606. In this example, the press 602 and the ultrasound transducer 604 can provide the compressive force and the ultrasound energy, respectively, in a first direction (e.g., downward in this example with respect to the target position 609). In some examples, the press 602 and the ultrasound transducer 604 may respectively deliver the compressive force and the ultrasound energy at different times. For example, the ultrasound transducer 604 may first deliver ultrasound energy to the plurality of wood elements, and the press 602 may thereafter apply a compressive force to the plurality of wood elements. Alternatively, the press 602 may first apply a compressive force to the plurality of wood elements, and the ultrasound transducer 604 may thereafter deliver ultrasound energy to the plurality of wood elements. In some examples, the press 602 and the ultrasound transducer 604 may respectively deliver the compressive force and the ultrasound energy concurrently, and also at different times.

Figure 10B:
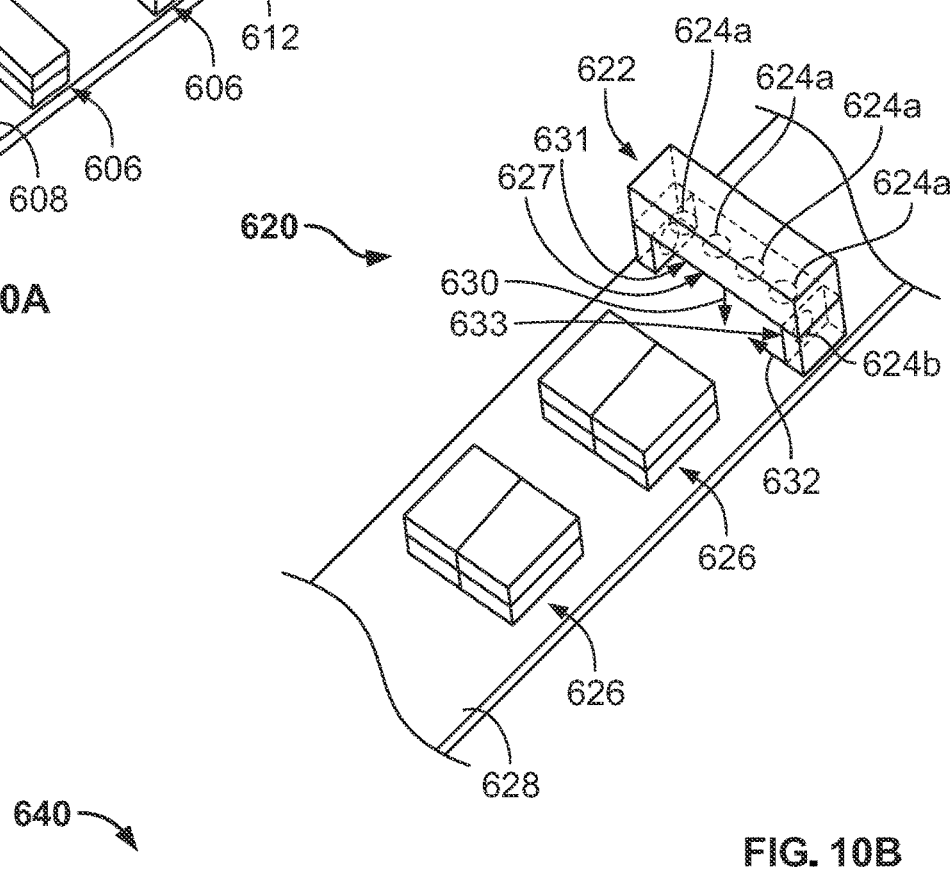
FIG. 10B is a conceptual diagram of another example press and example ultrasound transducers that are integral with the press, and that can be used for manufacturing composite wood products using ultrasound energy.

FIG. 10B is a conceptual diagram 620 of an example press 622 and one or more example ultrasound transducers 624a, 624b that are integral with the press 622, and that can be used for manufacturing composite wood products using ultrasound energy. The ultrasound transducers 624a, 624b and the press 622 may respectively and concurrently, in some implementations, deliver ultrasound energy and one or more compressive forces to a plurality of wood elements 626. The example of FIG. 10B shows four ultrasound transducers 624a that are integral with the press 622 and that are arranged to deliver ultrasound energy in a first direction (e.g., in a downward direction from a position above the plurality of wood elements in this example) toward the plurality of wood elements 626 when the plurality of wood elements 626 is in a target position 627. The example of FIG. 10B shows one ultrasound transducer 624b that is integral with the press 622 and is arranged to deliver ultrasound energy from a second direction (e.g., in a lateral direction, leftward from a position right of the plurality of wood elements in this example) toward the plurality of wood elements 626 when the plurality of wood elements 626 is in the target position 627. The example of FIG. 10B shows wood elements 626 (four wood sheets, arranged 2×2 (two-high by two-wide), but any of the wood elements discussed herein could alternatively be used) on a conveyor 628, which may move the plurality of wood elements 626 into the target position 627.

The press 622, in this example, may apply a downward compressive force 630 to the plurality of wood elements 626, for example when the plurality of wood elements 626 are in the target position 627. The press 622 includes a first surface 631 that can apply the downward compressive force 630 to the plurality of wood elements 626. The press 622 may also apply, in this example, a lateral compressive force 632 to the plurality of wood elements 626, for example when the plurality of wood elements 626 are moved in the target position 6. In this example, the lateral compressive force 632 may be a leftward compressive force applied by the press 622 from the right of the plurality of wood elements 626 when the plurality of wood elements are located in the target position 627. The press 602 includes a second surface 633 that can apply the lateral force 632 to the plurality of wood elements 626. In some examples, the lateral compressive force may be a rightward compressive force applied by the press 622 (using a surface of the press opposite the second surface 633 in FIG. 10B, for example) from the left of the plurality of wood elements 626 when the plurality of wood elements are located in the target position 627. In some examples, two lateral compressive forces may be applied by the press 622. For example, both a leftward lateral compressive force and a rightward lateral force may be applied by the press 622, according to some implementations.

In some examples, the press 622 can apply one or more downward forces (e.g., force 630) and one or more lateral forces (e.g., force 632, or other lateral forces described above) concurrently. In some examples, the press 622 can apply one or more downward forces and one or more lateral forces at different times. For example, the press 622 may first apply the downward force 630, and then may apply the lateral force 632 (or other lateral forces). As another example, the press 622 may first apply the lateral force 632 (or other lateral forces), and then may apply the downward force 630.

In some examples, the ultrasound transducers 624a can be arranged flush with the first surface 631 of the press 622 that can apply the downward compressive force 630 to the plurality of wood elements 626. In some examples, the ultrasound transducers 624a can be arranged to be recessed with respect to the first surface 631 of the press 622. Similarly, in some examples the ultrasound transducer 624b can be arranged flush with the second surface 633 of the press 622 that can apply the lateral compressive force 632 to the plurality of wood elements 626, and in some examples the ultrasound transducer 624b can be arranged to be recessed with respect to the second surface 633. In this example, the press 622 and the ultrasound transducers 624a, 624b can provide the one or more compressive forces 630, 632 and the ultrasound energy, respectively, in a first direction (e.g., downward in this example with respect to the target position 627) and in a second direction (e.g., laterally in this example with respect to the target position 627). In some examples, the press 622 and the ultrasound transducers 624a, 624b may respectively deliver the one or more compressive forces and the ultrasound energy at different times, for example in manners similar to those discussed above with reference to FIG. 10A.

Figure 10C:
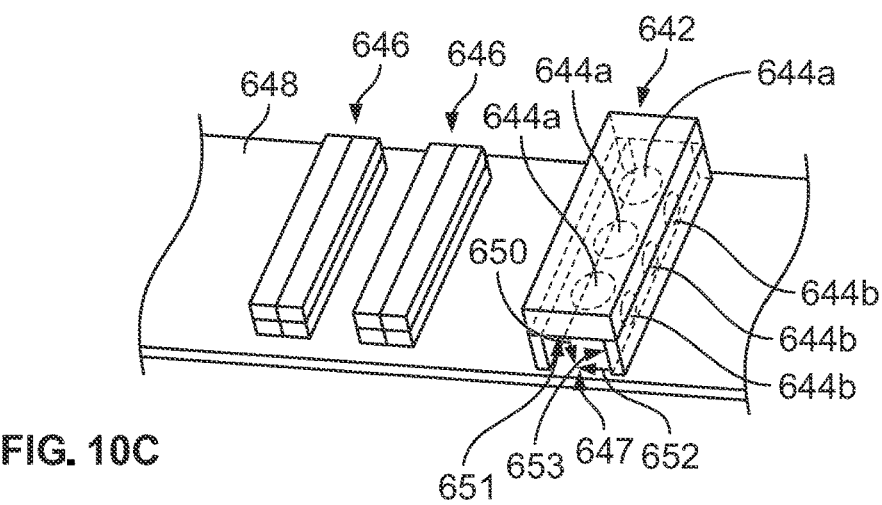
FIG. 10C is a conceptual diagram of yet another example press and example ultrasound transducers that are integral with the press, and that can be used for manufacturing composite wood products using ultrasound energy.

FIG. 10C is a conceptual diagram 640 of an example press 642 and one or more example ultrasound transducers 644a, 644b that are integral with the press 642, and that can be used for manufacturing composite wood products using ultrasound energy. The ultrasound transducers 644a, 644b and the press 642 may respectively and concurrently, in some implementations, deliver ultrasound energy and one or more compressive forces to a plurality of wood elements 646. The example of FIG. 10C shows three ultrasound transducers 644a that are integral with the press 642 and that are arranged to deliver ultrasound energy in a first direction (e.g., in a downward direction from a position above the plurality of wood elements in this example) toward the plurality of wood elements 646 when the plurality of wood elements 646 is in a target position 647. The example of FIG. 10C shows three ultrasound transducers 644b that are integral with the press 642 and are arranged to deliver ultrasound energy from a second direction (e.g., in a rearward direction from a position forward of the plurality of wood elements 646 when the wood elements are in the target position 647) toward the plurality of wood elements 646. The example of FIG. 10C shows wood elements 646 (four wood strips, arranged 2×2 (two-high by two-wide), but any of the wood elements discussed herein could alternatively be used) on a conveyor 648, which may move the plurality of wood elements 646 into the target position 647.

The press 642, in this example, may apply a downward compressive force 650 to the plurality of wood elements 646, for example when the plurality of wood elements 646 are in the target position 647. The press 642 includes a first surface 651 that can apply the downward force 650 to the plurality of wood elements 646. The press 642 may also apply, in this example, a rearward compressive force 652 to the plurality of wood elements 646, for example when the plurality of wood elements 646 are in the target position 647. In this example, the rearward compressive force 652 may be applied by the press 622 from a position forward of the plurality of wood elements 646 when the plurality of wood elements are located in the target position 647. The press 642 includes a second surface 653 that can apply the rearward compressive force 652 to the plurality of wood elements 646. In some examples, the press may apply a forward compressive force (e.g., using a surface of the press opposite the second surface 653 in FIG. 10C) from a position behind the plurality of wood elements 646 when the plurality of wood elements is located in the target position 647. In some examples, the press 622 may apply both a rearward force and a forward force to the plurality of wood elements.

In some examples, the press 642 can apply one or more downward forces (e.g., force 650) and one or more other forces (e.g., force 652, or other forces described above) concurrently. In some examples, the press 642 can apply one or more downward forces and one or more other force at different times. For example, the press 642 may first apply the downward force 650, and then may apply the rearward force 652 (or a forward force, or other forces). As another example, the press 642 may first apply the rearward force 652 (or the forward force, or other forces), and then may apply the downward force 650.

In some examples, the ultrasound transducers 644a can be arranged flush with the first surface 651 of the press 642 that can apply the downward compressive force 650 to the plurality of wood elements 646. In some examples, the ultrasound transducers 644a can be arranged to be recessed with respect to the first surface 651 of the press 642. Similarly, in some examples the ultrasound transducers 644b can be arranged flush with the second surface 653 of the press 642 that can apply the rearward compressive force 652 to the plurality of wood elements 646, and in some examples the ultrasound transducers 644b can be arranged to be recessed with respect to the second surface 653. In this example, the press 642 and the ultrasound transducers 644a, 644*b* can provide the one or more compressive forces 650, 652 and the ultrasound energy, respectively, in a first direction (e.g., downward in this example with respect to the target position 647) and in a second direction (e.g., rearward in this example with respect to the target position 647). In some examples, the press 642 and the ultrasound transducers 644*a*, 644*b* may respectively deliver the one or more compressive forces and the ultrasound energy at different times, for example in manners similar to those discussed above with reference to FIG. 10A.

The examples of FIGS. 10B and 10C show that ultrasound energy can be delivered to a plurality of wood elements from two or more directions, according to some implementations. For example, the examples of FIGS. 10B and 10C show that ultrasound energy can be delivered to a plurality of wood elements in a downward direction (e.g., from a position generally above the plurality of wood elements) and in another direction different from the downward direction (e.g., in a lateral direction, such as from a position left-of or right-of the wood elements; in a rearward direction, such as from a location forward of the wood elements; and in a forward direction, such as from a location rearward of the wood elements).

Figure 11A:
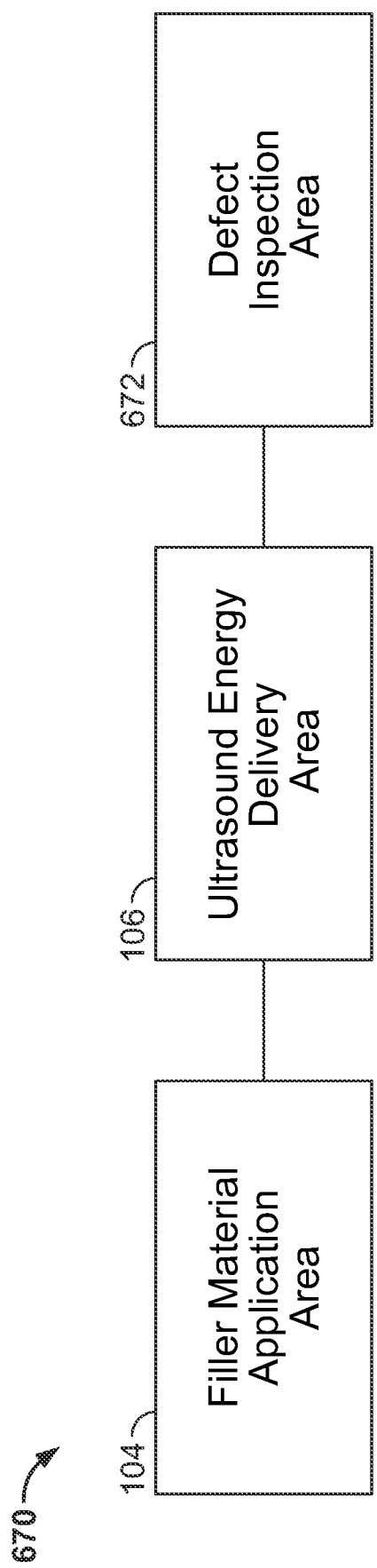
FIG. 11A is a block diagram of an example environment for manufacturing composite wood products using ultrasound energy.

FIG. 11A is a block diagram of an example environment 670 for manufacturing composite wood products using ultrasound energy. The environment 670 includes the filler material application area 104 and the ultrasound energy delivery area 106, each described above with reference to FIG. 1 and other figures, including the components that can be included in areas 104 and 106, and also includes a defect inspection area 672. In some examples, after the plurality of wood elements has been bonded into a composite wood product, the composite wood product may be inspected for defects, which may occur in the defect inspection area 672. In various implementations, the inspecting for defects can include delivering ultrasound energy to the composite wood product. This additional delivery of ultrasound energy may be delivered, in some examples, by the same ultrasound transducer or transducers that delivered the ultrasound energy to the plurality of wood elements in the bonding of the wood elements. In some examples, this additional delivery of ultrasound energy may be delivered by one or more ultrasound transducers different from those that delivered the ultrasound energy to the plurality of wood elements in the bonding of the wood elements.

The defect inspection area 672 may include a defect inspection component that may deliver ultrasound energy (e.g., via one or more ultrasound transducers) to the composite wood product, and may inspect the product for a defect. In some examples, the defect inspection component may include one or more cameras. In some examples, the ultrasound energy may be delivered by one or more ultrasound transducers that are separate from the defect inspection component. Although not shown in FIG. 11A for brevity, it will be understood that in some implementations one or more of the compression force application area 552 of FIG. 8 and the wood element preparation area 102 of FIG. 1 may also be included in environment 670.

Figure 11B:
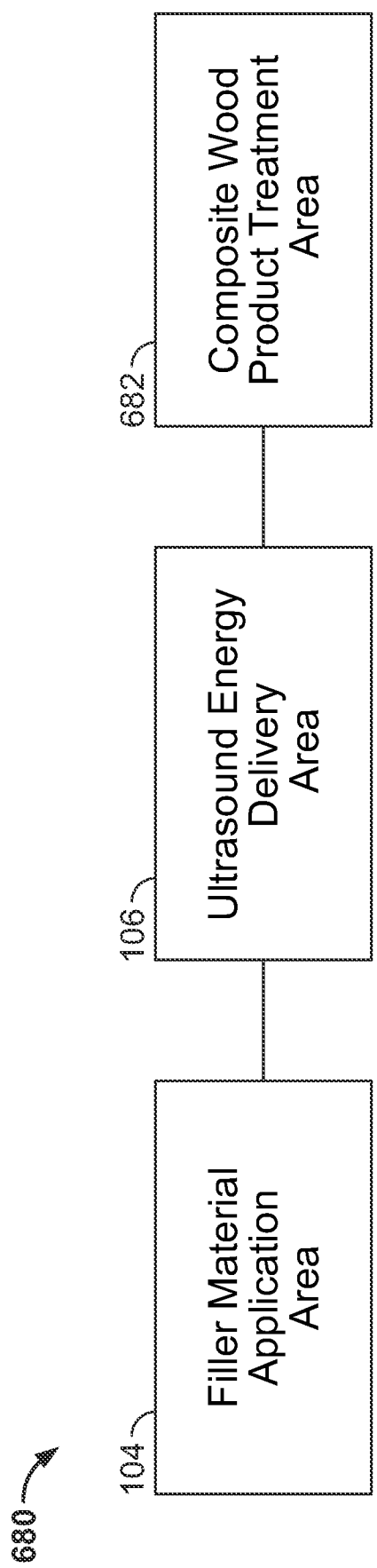
FIG. 11B is a block diagram of an example environment for manufacturing composite wood products using ultrasound energy.

FIG. 11B is a block diagram of an example environment 680 for manufacturing composite wood products using ultrasound energy. The environment 680 includes the filler material application area 104 and the ultrasound energy delivery area 106, each described above with reference to FIG. 1 and other figures, including the components that can be included in areas 104 and 106, and also includes a composite wood product treatment area 682. In some examples, after the plurality of wood elements has been bonded into a composite wood product, a treatment may be applied to the composite wood product, which may occur in the composite wood product treatment area 682.

In various implementations, the treatment application to the composite wood product can include delivering ultrasound energy to the composite wood product. This additional delivery of ultrasound energy may be delivered, in some examples, by the same ultrasound transducer or transducers that delivered the ultrasound energy to the plurality of wood elements in the bonding of the wood elements. In some examples, this additional delivery of ultrasound energy may be delivered by one or more ultrasound transducers different from those that delivered the ultrasound energy to the plurality of wood elements in the bonding of the wood elements.

Examples of treatments that can be applied to the composite wood products can include one or more sealants, flame-retardant treatments, insect- or vermin-repellant treatments, stains, paints, or other post-treatments, and as described such treatment can also include delivery of ultrasound energy to the composite wood product. In some examples, an edging treatment may be applied to the composite wood product, and as described such treatment can also include delivery of ultrasound energy to the composite wood product. In some examples, the ultrasound energy may provide one or more benefits with reference to the treatment similar to those described above with reference to the filler material. For example, the ultrasound energy may stimulate diffusion across or penetration of the treatment into, or deeper into, the composite wood product, or may stimulate better flow of the treatment for treatments that are liquid or capable of flowing.

The composite wood product treatment area 682 may include a treatment delivery component, which may apply the treatment to the composite wood product. In some examples, the treatment application component may include one or more of rollers, brushes, spray applicators, or the like. In some examples, the treatment application component can deliver ultrasound energy (e.g., via one or more ultrasound transducers) to the composite wood product. In some examples, the ultrasound energy may be delivered by one or more ultrasound transducers that are separate from the treatment application component. Although not shown in FIG. 11B for brevity, it will be understood that in some implementations one or more of the compression force application area 552 of FIG. 8, the wood element preparation area 102 of FIG. 1, and the defect inspection area 672 of FIG. 11A may also be included in environment 680.

Figure 11C:
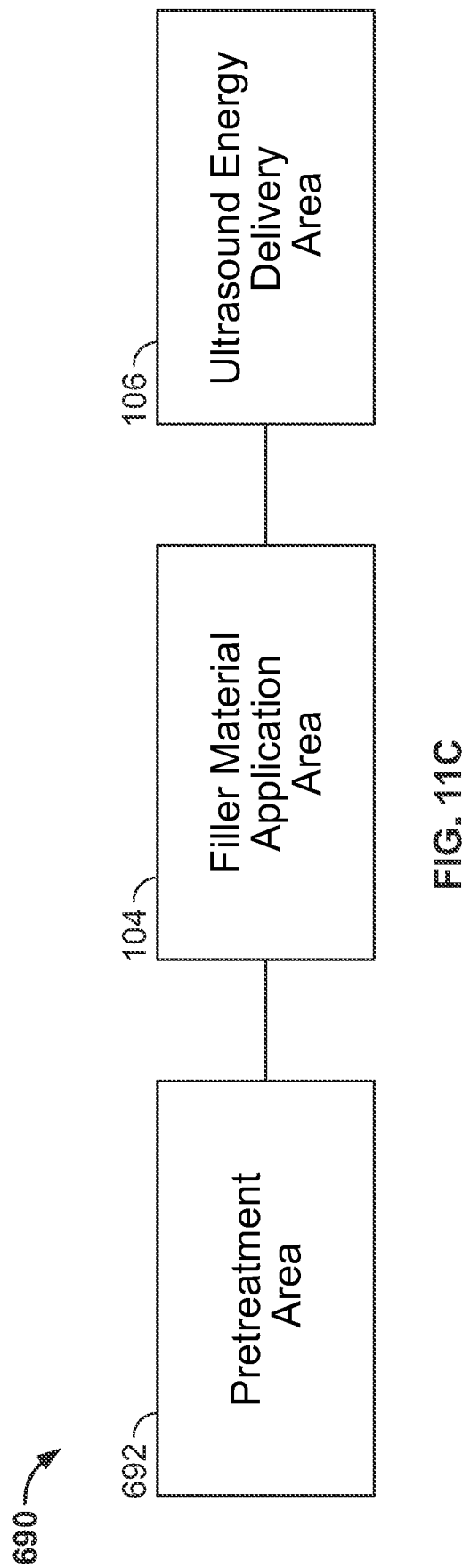
FIG. 11C is a block diagram of an example environment for manufacturing composite wood products using ultrasound energy.

FIG. 11C is a block diagram of an example environment 690 for manufacturing composite wood products using ultrasound energy. The environment 690 includes the filler material application area 104 and the ultrasound energy delivery area 106, each described above with reference to FIG. 1 and other figures, including the components that can be included in areas 104 and 106, and also includes a pretreatment area 692. In some examples, before applying filler material to the plurality of wood elements, a pretreatment that includes delivery of ultrasound energy to the plurality of wood elements may be applied to the plurality of wood elements, which may occur in the pretreatment area 692. In some examples, such pretreatment with ultrasound energy may clean the wood elements. For example, the cleaning may help to remove dirt or other impurities from the wood elements. The pretreatment area 692 may include a pretreatment delivery component. The pretreatment of wood elements may include delivering ultrasound energy at a lower ultrasound energy level than the ultrasound energy level used in bonding the plurality of wood elements, according to some implementations. For example, one or more ultrasound transducers may deliver ultrasound energy to the plurality of wood elements as a pretreatment of the plurality of wood elements. This pretreatment delivery of ultrasound energy may be delivered, in some examples, by the same ultrasound transducer or transducers that will deliver the ultrasound energy to the plurality of wood elements in the bonding of the wood elements. In some examples, this pretreatment delivery of ultrasound energy may be delivered by one or more ultrasound transducers different from those that will deliver the ultrasound energy to the plurality of wood elements in the bonding of the wood elements. Although not shown in FIG. 11C for brevity, it will be understood that in some implementations one or more of the compression force application area 552 of FIG. 8, the wood element preparation area 102 of FIG. 1, the defect inspection area 672 of FIG. 11A, and the composite wood product treatment area 682 of FIG. 11B may also be included in environment 690.

In some examples, an ultrasound transducer that includes a roller element can be used to deliver ultrasound energy to a plurality of wood elements. The roller element may have various shapes and sizes, depending on the implementation. For example, in some implementations, the roller element may include a cylindrical body. In some implementations, the roller element may include a spherical body. In some examples, the body of the roller element may include an outer surface configured to physically contact the plurality of wood elements during delivery of the ultrasound energy. In some examples, the body of the roller element may include an outer surface configured to physically contact and roll across the plurality of wood elements during delivery of the ultrasound energy. In some examples, the outer surface of the body of the roller element may be substantially smooth. In some examples, the outer surface of the body of the roller element may include a plurality of protrusions. In some examples, the outer surface of the body of the roller element may include a plurality of recessed features. In some examples, the outer surface of the body of the roller element may include one or more protrusions and one or more recessed features.

Figure 12A:
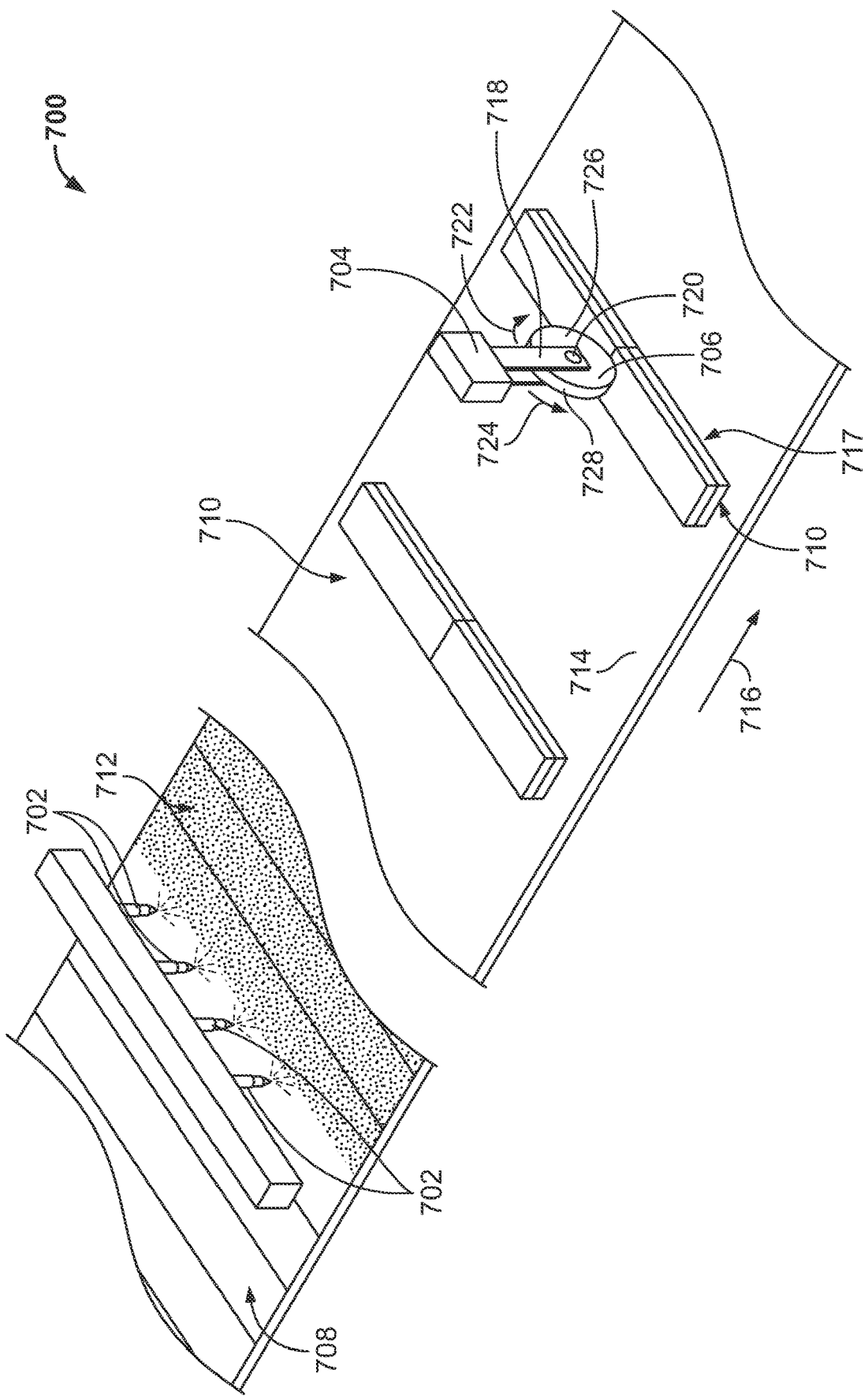
FIG. 12A is a conceptual diagram of an example environment for manufacturing composite wood products using ultrasound energy, where the example environment includes an example ultrasound transducer that includes an example roller element.

FIG. 12A is a conceptual diagram of an example environment 700 for manufacturing composite wood products using ultrasound energy, where the example environment 700 includes an example ultrasound transducer 704 that includes an example roller element 706. The environment 700 includes example filler material applicators 702, an example ultrasound transducer 704, and an example roller element 706. Filler material applicators 702 can apply a filler material to a plurality of wood elements 708, in a manner similar to that described above with reference to applicators 158 of FIG. 3A. In the depicted example of FIG. 12A, the applicators 702 are spray nozzles, but any of the other types of applicators (e.g., one or more brushes, rollers, or other types of applicators) described herein may alternatively be used.

A plurality of wood elements 710 may be arranged in proximity to one another. For example, a plurality of wood elements 710 may be stacked vertically and arranged laterally, or may be arranged in any appropriate manner. In the depicted example of FIG. 12A, the wood elements, which may be wood veneers in this example, are arranged 2×2. In some examples, the plurality of wood elements 710 includes one or more elements 712 that have had filler material applied thereto by the applicators 702. In some examples, the plurality of wood elements 710 includes one or more elements 712 that have had filler material applied thereto, and one or more wood elements that have not have filler material applied thereto. And in some examples, the plurality of wood elements 710 does not include filler material. The plurality of wood elements 710 may be arranged on a conveyor 714, and may travel in a direction 716 on the conveyor 714. The conveyor 714 may move the plurality of wood elements 710 into a target position 717 with respect to the ultrasound transducer 704, with respect to the roller element 706, or with respect to both the ultrasound transducer 704 and the roller element 706.

Ultrasound energy may be generated by the ultrasound transducer 704, and may be delivered to the plurality of wood elements 710 via the roller element 706, according to some examples. The ultrasound energy may be guided from the ultrasound transducer 704 to the roller element 706 by an example ultrasound horn 718, which may be coupled to the ultrasound transducer 704 and may be configured to guide the ultrasound energy from the transducer 704 to the roller element 706. The roller element 706 may rotate about an axis, such as an axel 720, which may couple the roller element 706 to the horn 718. In some examples, the roller element 706 may rotate about the axel 720 in a first direction 722. For example, the first direction 722 may be a clockwise direction. In some examples, the first direction 722 may be a clockwise direction with respect to the axel 720. In some examples, the roller element 706 may rotate about the axel 720 in a second direction 724. For example, the second direction 724 may be a counter-clockwise direction. In some examples, the second direction 724 may be a counter-clockwise direction with respect to the axel 720. In some examples, the roller element 706 may rotate about the axel 720 in both the first direction 722 and the second direction 724. In some examples, the second direction 724 may be opposite the first direction 722.

In some examples, the roller element 706 may include a cylindrical body 726, and an outer surface 728 of the cylindrical body 726 may be configured to physically contact one or more wood elements of the plurality of wood elements 710 while ultrasound energy is being delivered to the plurality of wood elements. For example, the roller element 706 may rotate about its axis in the first direction 722, or in the second direction 724, and the outer surface 728 of the cylindrical body 726 of the roller element 706 may physically contact one or more wood elements of the plurality of wood elements 710 as the cylindrical body 726 of the roller element 706 rotates. In the depicted example of FIG. 12A, it can be seen that the outer surface 728 will contact two wood elements (e.g., the two elements on the top of the 2×2 stack) of the plurality of wood elements 710 as the roller element 706 rolls across the top of the plurality of wood elements 710.

FIG. 12B is a conceptual diagram of another example ultrasound transducer 730 that includes another example roller element 732. The ultrasound transducer 730 may be similar to ultrasound transducer 704 described herein above with reference to FIG. 12A. The ultrasound transducer 730 may generate ultrasound energy, which may be guided from the ultrasound transducer 730 to the roller element 732 by an example ultrasound horn 734, which may be coupled to the ultrasound transducer 730 and may be configured to guide the ultrasound energy from the transducer 730 to the roller element 732. The roller element 732, in this example, includes a spherical body 736. That is, the roller element 732 may generally have the shape of a sphere. An outer surface 738 of the spherical body 736 may physically contact one or more wood elements 737 of a plurality of wood elements.

Like the roller element 706 of FIG. 12A, the roller element 732 may roll over wood elements, but in some implementations the spherical body 736 of roller element 732 may roll in any number of directions 739a, 739b, 739c, 739d, 739e, 739f, 739g, 739h, 739i, 739j and others, analogous to a ball used in early computer mice rolling across a mouse pad, for example. For example, the roller element 732 may roll in any direction in a two-dimensional plane, according to some implementations. One or more example support members 740 may provide mechanical support to the spherical body 736 of the roller element 732, according to some implementations. In some examples, the support members 740 may be rollers. In some examples, the support members 740 may be pads, cushions, stops, or other appropriate components for at least partially maintaining the roller element 732 with respect to the horn 734. In some examples, there may be more or fewer support members 740 than are shown in FIG. 12B. In some examples, the ultrasound transducer 730, horn 734 and roller element 732 may be substituted for the ultrasound transducer 704, horn 718 and roller element 706 of FIG. 12A.

In some examples, ultrasound energy may be delivered to the plurality of wood elements via the roller elements 706 or 732. In various implementations, the ultrasound energy may have a frequency within a range of 10 kHz-20 MHz. In some examples, the ultrasound energy may have a frequency within a range of 15 kHz-1 MHz, or within a range of 20 kHz-100 kHz. In some examples, the ultrasound energy may radiate from the outer surface 728 or 738 to the plurality of wood elements 710. The ultrasound energy may pass from the roller element 706 or 732 to the plurality of wood elements 710 by way of one or more of longitudinal ultrasound waves, radiating ultrasound waves, or shear ultrasound waves, according to various implementations. In some examples, at least a portion of the outer surface 728 or 738 may remain in physical contact with at least one wood element of the plurality of wood elements 710 as the ultrasound energy is being delivered. In some examples, the ultrasound energy may continue to be delivered when the outer surface 728 or 738 is not in physical contact with any elements of the plurality of wood elements 710, such as one or more of before, after, or both before and after the outer surface 728 or 738 contacts the wood elements.

In some examples, the system that includes the ultrasound transducer 704 or 730 and the roller element 706 or 732, respectively, may stimulate bonding of the wood elements by providing ultrasound energy to the plurality of wood elements 710. As described herein above with reference to other systems for manufacturing composite wood products using ultrasound energy, the provided ultrasound energy may provide various mechanical stimulations (e.g., vibratory stimulation at molecular and macro levels) to the plurality of wood elements 710 and to the filler material, may provide thermal stimulation to the plurality of wood elements 710 and to the filler material, may provide a diffusional stimulation to the filler material, and friction generated between wood elements by the ultrasound energy delivery may further stimulate the bonding. Sonication pressure (e.g., pressure from the ultrasound waves) because of the provided ultrasound energy may also stimulate bonding of the plurality of wood elements. Advantageously, the ultrasound transducer 704 or 730 and roller element 706 or 732, respectively, may continuously stimulate the plurality of wood elements 710 and filler material, which may beneficially aid in the bonding.

The roller element 706 or 732 may include any appropriate materials. In some examples, the roller element 706 or 732 includes titanium. In some examples, the roller element 706 or 732 includes aluminum. In some examples, the roller element 706 or 732 may provide a compressive force to the plurality of wood elements 710 as the outer surface 728 or 738 rolls over the wood elements. In some examples, the roller element 706 or 732 may not provide a compressive force to the plurality of wood elements as the outer surface 728 or 738 rolls over the wood elements.

Figure 12C:
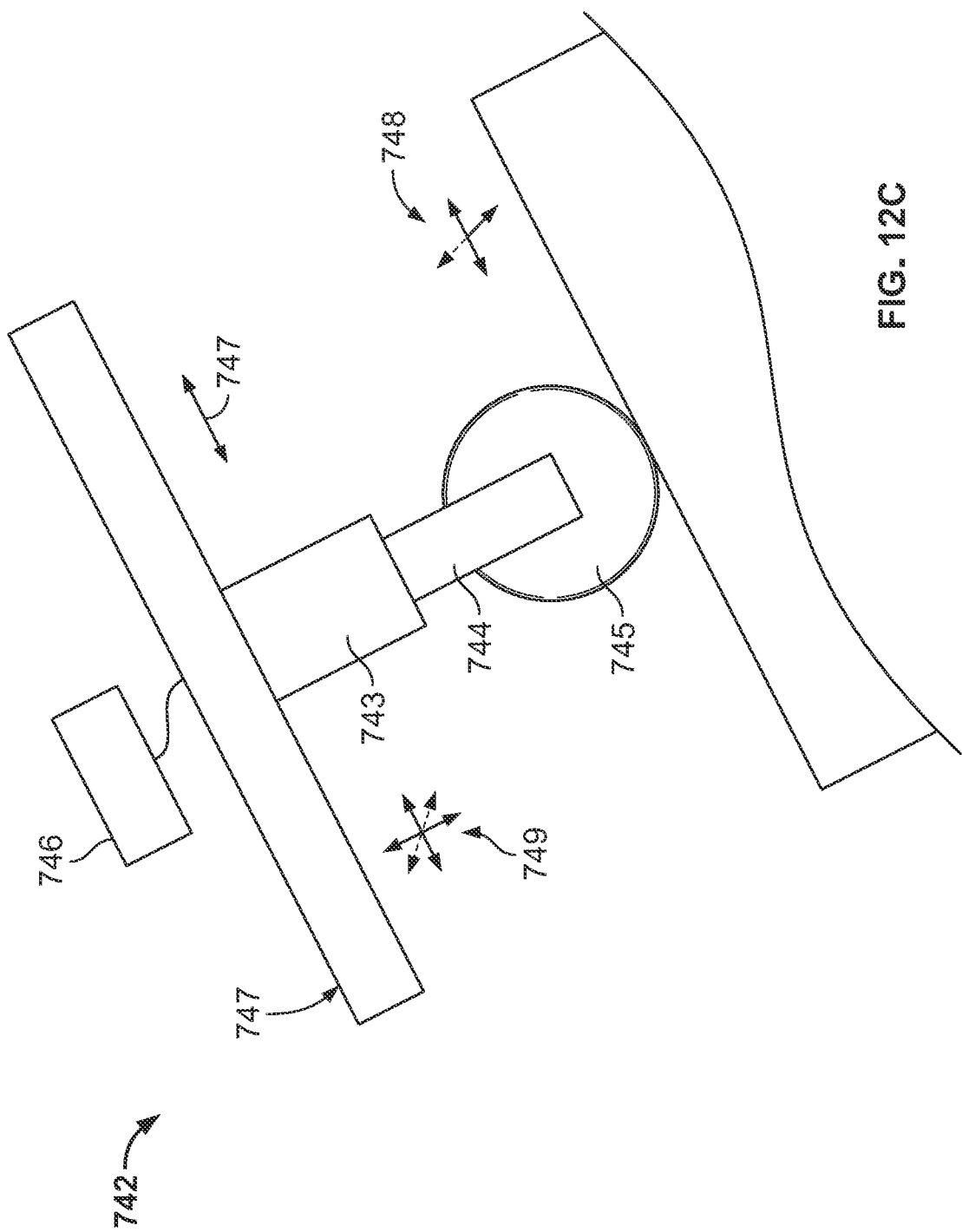
FIG. 12C is a conceptual diagram of an example environment for manufacturing composite wood products using ultrasound energy.

In some implementations, the ultrasound transducer 704 or 730 may move concurrently with the roller element 706 or 732 as the roller element 706 or 732 rolls over the plurality of wood elements 710. FIG. 12C is a conceptual diagram of an environment 742 for manufacturing composite wood products using ultrasound energy. An example ultrasound transducer 743 includes an example horn 744 and example roller element 745, and these may represent the transducers 704 or 730, horns 718 or 734, and roller elements 706 or 732, respectively, of FIGS. 12A and 12B, according to some implementations. An example motion controller 746 may control movement of the transducer 743 in some implementations. In some examples, the motion controller 746 may control movement of the transducer 743, and by extension the horn 744 and the roller element 745. The motion controller 746 may include one or more motors (e.g., servo motors, stepper motors, linear motors, direct drive motors, AC motors, or DC motors, to list just a few examples), and may include a motion control module that may provide one or more signals to the one or more motors, to control movement of the ultrasound transducer 743. In the example of FIG. 12C, the motion controller 746 is depicted separate from the ultrasound transducer 743, but in some implementations the motion controller 746 may be integral with the ultrasound transducer 743.

Depending on the application, the motion controller 746 may control the ultrasound transducer 743 to move in a variety of directions or patterns. In some examples, the motion controller 746 may command the ultrasound transducer 743 (and by extension the horn 744 and roller element 745, in some examples) to move linearly 748 (e.g., forward, backward, or each of forward and backward). In some examples, the ultrasound transducer 743 may be configured to move in a single-axis motion system. In some examples, the motion controller 746 may command the ultrasound transducer 743 (and by extension the horn 744 and roller element 745, in some examples) to move in a two-dimensional pattern (e.g., move within a two-dimensional plane), such as a pattern to cover a surface of one or more wood elements of a plurality of wood elements. In some examples, the motion controller 746 may command the ultrasound transducer 743 to move in a three-dimensional pattern (e.g., move within a three-dimensional space). FIG. 12C depicts a pattern 749 intended to show that the ultrasound transducer in some examples (and by extension the horn 744 and roller element 745, in some examples) may move in any direction in a three-dimensional space, where for simplicity and brevity arrows out of the page and into the page are not shown in the pattern 749. In some examples, the ultrasound transducer 743 (and by extension the horn 744 and roller element 745, in some examples) may be configured to move in a multi-axis motion system, such as a two-axis motion system or a three-axis motion system.

In some examples, the motion controller 746 may include one or more of a processing component, a communications module, a memory, a power module, and one or more sensors. While these are not shown in FIG. 12C for simplicity, in some examples the motion controller 746 may include one of more of processing component 872, communications module 874, memory 876, power module 878, and one or more sensors 880 of FIG. 15B, to be described in more detail below with reference to FIG. 15B, and may use these in providing the motion control functionality described above.

In some implementations, the ultrasound transducer 743 may be configured to move along one or more tracks. In some implementations, the ultrasound transducer 743 may be configured to move along one or more rails or sliders. In some examples, the ultrasound transducer 743 may be configured to move across a two-dimensional grid. In some examples, the ultrasound transducer 743 may be configured to move across a two-dimensional grid for a given height (or width, or depth) setting, and may be configured to move across the two-dimensional grid at a variety of height (or width, or depth) settings (e.g., to move within a three-dimensional space). Referring again to FIG. 12C, the ultrasound transducer 743 may be configured to move along or across a motion guide 747. In some examples, the motion guide 747 may be one or more rails, sliders, or tracks. In some examples, the motion guide 747 may be a two-dimensional grid. In some examples, the motion guide 747 may be a moveable two-dimensional grid, moveable in a third dimension different from the two dimensions of the grid.

In some examples, the ultrasound transducer may remain generally stationary as the roller element rolls over the plurality of wood elements. In some examples, the horn may be configured to extend or retract as the roller element rolls over the plurality of wood elements, according to some implementations.

In some examples, both the horn and the roller element may be considered to be part of the ultrasound transducer, and as such a portion of the ultrasound transducer may be in physical contact with the wood elements or the filler material while ultrasound energy is being delivered to the plurality of wood elements, according to some examples. In some examples, the horn or the roller element may not be considered to be part of the ultrasound transducer.

Whether the roller element includes a cylindrical body or a spherical body, the outer surface of the respective body may include various features, according to some examples. In some examples, the external surface of the cylindrical body 728 or spherical body 738 may be substantially smooth, may include a plurality of protrusions, may include a plurality of recessed features, or may include one or more protrusions and one or more recessed features.

FIG. 13A is a side view 750 of an example roller element 752, ultrasound transducer 754 and horn 756, each of which may respectively represent the roller element 706, ultrasound transducer 704 and horn 718 of the FIG. 12A example, or the roller element 732, ultrasound transducer 730 and horn 734 of the FIG. 12B example. As can be seen in FIG. 13A, an outer surface 758 of the body of the roller element 752 is substantially smooth.

In some examples, the external surface of the body of the roller element may include a plurality of protrusions. FIG. 13B is a side view 760 of another example roller element 762, the ultrasound transducer 754, and horn 756, each of which may respectively represent the roller element 706, ultrasound transducer 704 and horn 718 of the FIG. 12A example, or the roller element 732, ultrasound transducer 730 and horn 734 of the FIG. 12B example. As can be seen in FIG. 13B, an outer surface 764 of the body of the roller element 762 includes a plurality of protrusions 766, where the protrusions 766 protrude from the outer surface 764.

In some examples, the external surface of the body of the roller element may include a plurality of recessed features, or features that are recessed with respect to a surface of the roller element. FIG. 13C is a side view 780 of another example roller element 782, the ultrasound transducer 754, and horn 756, each of which may respectively represent the roller element 706, ultrasound transducer 704 and horn 718 of the FIG. 12A example, or the roller element 732, ultrasound transducer 730 and horn 734 of the FIG. 12B example. As can be seen in FIG. 13C, an outer surface 784 of the body of the roller element 782 includes a plurality of recessed features 786, where the recessed features 786 are recessed from the outer surface 784.

Figure 14A:
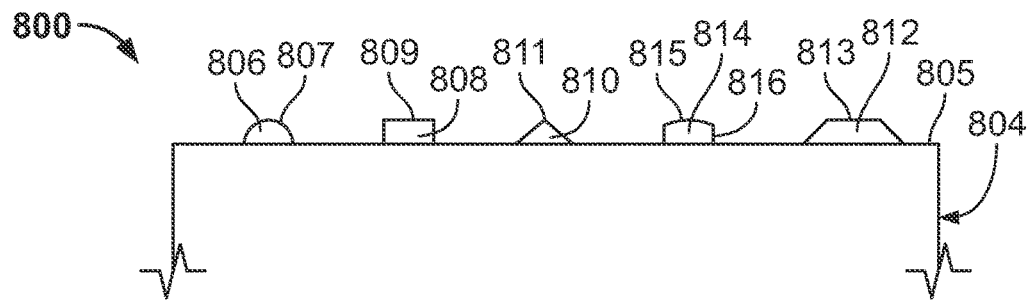
FIG. 14A is a front view and FIG. 14B is a top view of an example portion of an example roller element that includes a plurality of example protrusions.
Figure 14B:
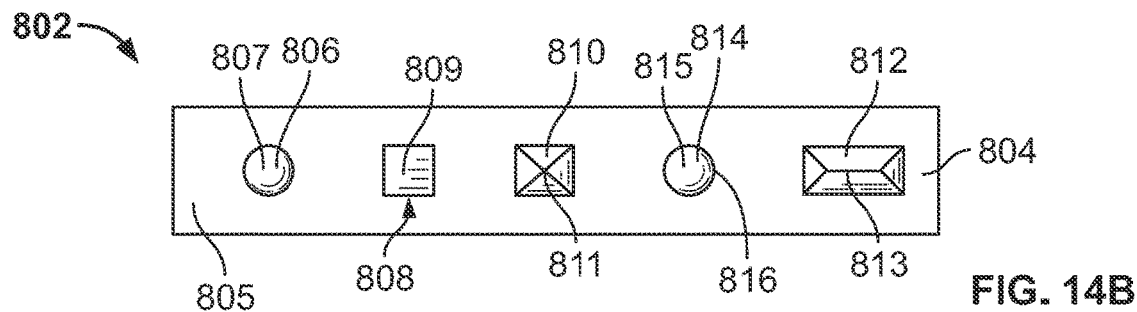

In various implementations, the protrusions 766 or recessed features 786 may have various shapes. FIG. 14A is a front view 800 and FIG. 14B is a top view 802 of an example portion of an example roller element 804 that includes a plurality of example protrusions 806, 808, 810, 812, 814. A body of the roller element 804 includes an outer surface 805 from which the protrusions 806, 808, 810, 812, 814 extend, or on which the protrusions 806, 808, 810, 812, 814 are located. A first protrusion 806 includes an outer surface 807 that is rounded. In some examples, the first protrusion 806 may generally have a "dome" shape. As can be seen in the top view 802 of FIG. 14B, a base of the first protrusion 806 has the shape of a circle, but any other appropriate shape (e.g., oval, square, rectangle, triangle, rhombus, diamond, or other appropriate shape) may alternatively be used for the base of the protrusion 806 with a rounded outer surface 807.

A second protrusion 808 includes an outer surface 809 that is substantially flat. As can be seen in the top view 802 of FIG. 14B, a base of the second protrusion 808, as well as the outer surface 809 of the second protrusion 808 has the shape of a square, but any other appropriate shape (e.g., oval, circle, rectangle, triangle, rhombus, diamond, or other appropriate shape) may alternatively be used for the base or for the outer surface 809 of the protrusion 808 with a substantially flat outer surface 809. In some examples, the base and the outer surface 809 of the second protrusion 808 may have different shapes, including combinations of any of the aforementioned shapes.

A third protrusion 810 includes an outer surface that comprises a point 811. In some examples, the point 811 may be an apex of the protrusion 810. In some examples, the third protrusion 810 may generally have a "pyramid" shape. As can be seen in the top view 802 of FIG. 14B, a base of the third protrusion 810 has the shape of a square, but any other appropriate shape (e.g., oval, circle, rectangle, triangle, rhombus, diamond, or other appropriate shape) may alternatively be used for the base of the protrusion 810 with an outer surface that comprises a point.

A fourth protrusion 812 includes an outer surface that comprises a ridge 813. As can be seen in the top view 802 of FIG. 14B, a base of the fourth protrusion 812 has the shape of a rectangle, but any other appropriate shape (e.g., oval, circle, square, triangle, rhombus, diamond, or other appropriate shape) may alternatively be used for the base of the protrusion 812 with an outer surface that comprises a ridge.

A fifth protrusion 814 includes an outer surface having a shape of a cylinder with a rounded top. The outer surface of the fifth protrusion 814 includes a cylindrical-shaped side surface 816 and a rounded top surface 815. As can be seen in the front view 800 of FIG. 14A, the rounded surface 815 is raised and offset from the surface 805 of the roller element 804 by the cylindrical-shaped side surface 816. In some examples, the fifth protrusion 814 may have a raised dome or cylindrical silo shape. As can be seen in the top view 802 of FIG. 14B, a base of the fifth protrusion 814 has the shape of a circle, but any other appropriate shape (e.g., oval, square, rectangle, triangle, rhombus, diamond, or other appropriate shape) may alternatively be used for the base of the fifth protrusion 814.

Figure 14C:
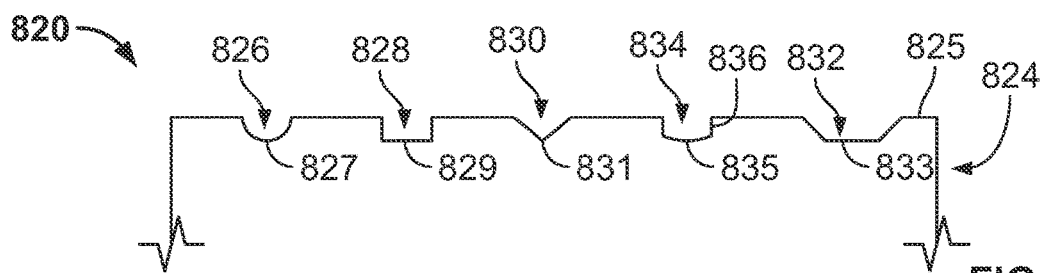
FIG. 14C is a front view and FIG. 14D is a top view of an example portion of an example roller element that includes a plurality of example recessed features.
Figure 14D:
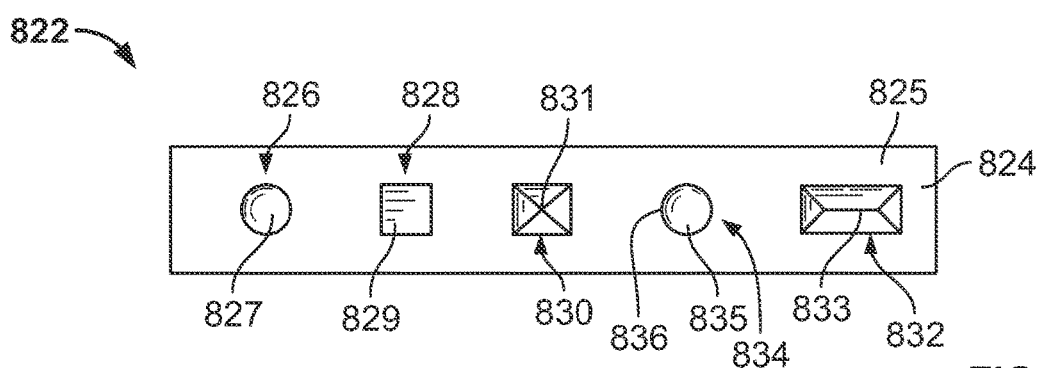

FIG. 14C is a front view 820 and FIG. 14D is a top view 822 of an example portion of an example roller element 824 that includes a plurality of example recessed features 826, 828, 830, 832, 834. A body of the roller element 824 includes an outer surface 825, from which the recessed features 826, 828, 830, 832, 834 are recessed or on which the recessed features 826, 828, 830, 832, 834 are located. A first recessed feature 826 includes a surface 827 that is rounded. The first recessed feature 826 may be a concave feature. The first recessed feature 826 may have the shape of a dimple. As can be seen in the top view 822 of FIG. 14D, a base of the first recessed feature 826 has the shape of a circle, but any other appropriate shape (e.g., oval, square, rectangle, triangle, rhombus, diamond, or other appropriate shape) may alternatively be used for the base of the recessed feature 826.

A second recessed feature 828 includes an outer surface 809 that is substantially flat. As can be seen in the top view 822 of FIG. 14D, a base of the second recessed feature 828, as well as the outer surface 829 of the second recessed feature 828 has the shape of a square, but any other appropriate shape (e.g., oval, circle, rectangle, triangle, rhombus, diamond, or other appropriate shape) may alternatively be used for the base or for the outer surface 829 of the recessed feature 828. In some examples, the base and the outer surface 829 of the second recessed feature 828 may have different shapes, including combinations of any of the aforementioned shapes.

A third recessed feature 830 includes an outer surface that comprises a point 831. In some examples, the point 831 may be a nadir of the recessed feature 830. In some examples, the point 831 may be the inverse apex of the recessed feature 830. As can be seen in the top view 822 of FIG. 14d, a base of the third recessed feature 830 has the shape of a square, but any other appropriate shape (e.g., oval, circle, rectangle, triangle, rhombus, diamond, or other appropriate shape) may alternatively be used for the base of the recessed feature 830 with an outer surface that comprises a point.

A fourth recessed feature 832 includes an outer surface that comprises a ridge 833, or a recessed ridge or inverted ridge. As can be seen in the top view 822 of FIG. 14D, a base of the fourth recessed feature 832 has the shape of a rectangle, but any other appropriate shape (e.g., oval, circle, square, triangle, rhombus, diamond, or other appropriate shape) may alternatively be used for the base of the recessed feature 832 with an outer surface that comprises a ridge.

A fifth recessed feature 834 includes an outer surface 835 having a shape of a cylinder with a rounded bottom. The outer surface of the fifth recessed feature 834 includes a cylindrical-shaped side surface 836 and a rounded bottom surface 835. As can be seen in the front view 820 of FIG. 14C, the rounded surface 835 is recessed and offset from the surface 825 of the roller element 824 by the cylindrical-shaped side surface 836. In some examples, the fifth recessed feature 834 may have a sunken dome or inverted cylindrical silo shape. As can be seen in the top view 822 of FIG. 14D, a base of the fifth recessed feature 834 has the shape of a circle, but any other appropriate shape (e.g., oval, square, rectangle, triangle, rhombus, diamond, or other appropriate shape) may alternatively be used for the base of the recessed feature 834.

Figure 14E:
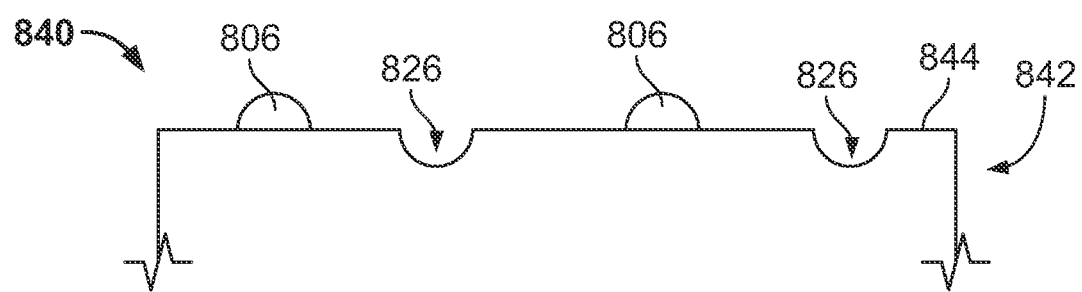
FIG. 14E is a front view of an example portion of an example roller element that includes one or more example protrusions and one or more example recessed features.

In some examples, the external surface of the cylindrical body may include one or more protrusions and one or more recessed features. FIG. 14E is a front view 840 of an example portion of an example roller element 842 that includes one or more example protrusions 806 and one or more example recessed features 826. A body of the roller element 842 includes an outer surface 844 from which the protrusions 806 extend and the recessed features 826 are recessed, or on which the protrusions 806 and recessed features 826 are located.

In some examples, the devices, systems and methods described herein may be used to deliver varying amounts, or different amounts, of ultrasound energy to a plurality of wood elements, or may be used to deliver ultrasound energy to one or more targeted areas or locations of the plurality of wood elements or within the plurality of wood elements, or may be used to deliver combinations of the foregoing. In some examples, a first amount of ultrasound energy may be delivered to a plurality of wood elements, and then a second amount of ultrasound energy may be delivered to the plurality of wood elements. In some implementations, the first amount of ultrasound energy may have an intensity that is higher than an intensity of the second amount of ultrasound energy. In some implementations, the first amount of ultrasound energy may have an intensity that is lower than an intensity of the second amount of ultrasound energy. In some examples, a first amount of ultrasound energy may be delivered to a plurality of wood elements for a first duration of time, and then a second amount of ultrasound energy may be delivered to the plurality of wood elements for a second duration of time, which may be different than the first duration of time (e.g., longer or shorter than the first duration).

In some examples, a first amount of ultrasound energy may be delivered to a first target location of, or within, a plurality of wood elements, and then a second amount of ultrasound energy may be delivered to a second target location of, or within, the plurality of wood elements. In some examples, the ultrasound transducer may remain stationary throughout delivery of both the first amount of ultrasound energy to the first target location and delivery of the second amount of ultrasound energy to the second target location. In some examples, the ultrasound transducer, or one or more portions of the ultrasound transducer, may move or be moved during delivery of the first amount of ultrasound energy to the first target location, during delivery of the second amount of ultrasound energy to the second target location, or during the time between delivery of the first amount and the second amount. As noted, ultrasound energy delivery can include various combinations of different amounts of ultrasound energy, for different durations, and targeted to different locations of, or within, a plurality of wood elements.

Figure 15A:
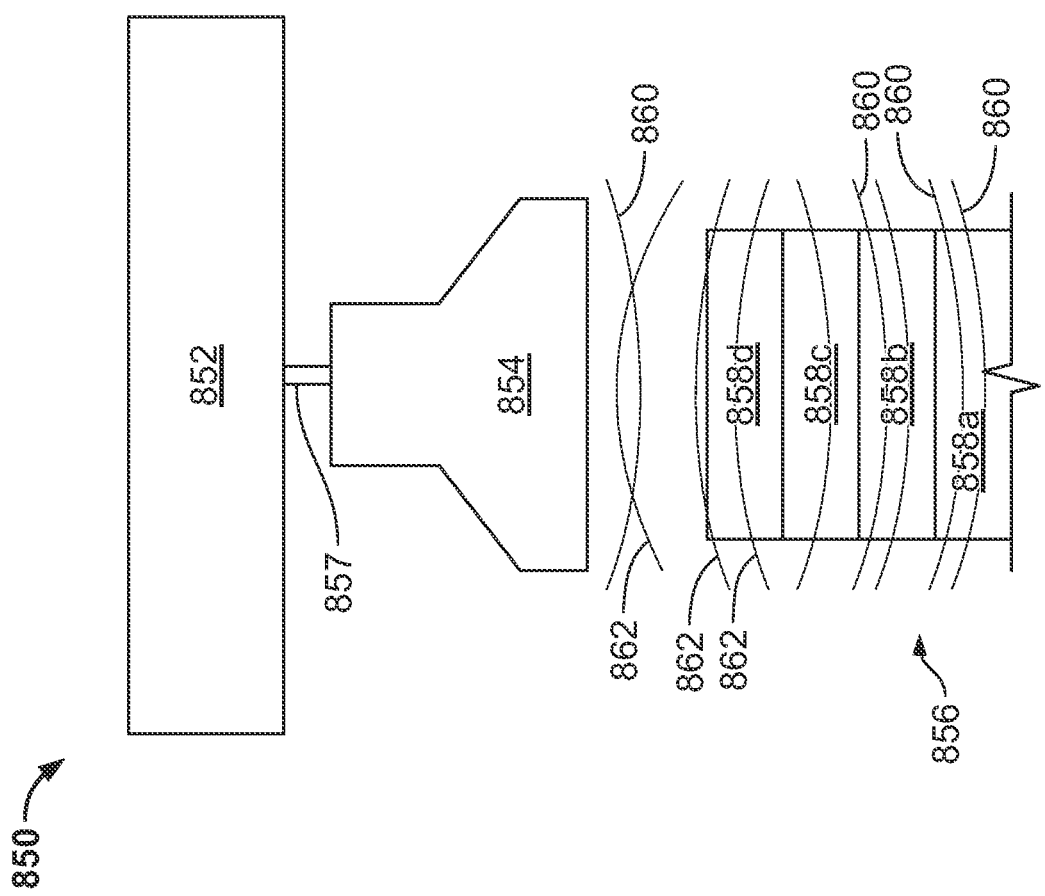
FIG. 15A is a conceptual diagram of an example control module and an example ultrasound transducer delivering ultrasound energy to a plurality of example wood elements for manufacturing a composite wood product using ultrasound energy.

FIG. 15A is a conceptual diagram 850 of an example control module 852 and an example ultrasound transducer 854 delivering ultrasound energy to a plurality of example wood elements 856 for manufacturing a composite wood product using ultrasound energy. The example control module 852 may provide one or more control signals 857 to the example ultrasound transducer 854 to control one or more of an amount of ultrasound energy, an intensity of ultrasound energy, a duration for ultrasound energy, a depth for ultrasound energy delivery, and a location target for ultrasound energy delivery, according to some examples. In general, control module 852 may be used with any of the example ultrasound systems described herein, and may be used to provide one or more of the aforementioned control signals 857 to the ultrasound transducer or transducers in any of the example systems described herein. In some examples, the control module 852 may provide one or more control signals to more than one ultrasound transducer, although for brevity only a single transducer 854 is depicted in FIG. 15A.

The example ultrasound transducer 854 has a generic shape, and may represent any of the ultrasound transducer shapes or topologies discussed herein. For example, transducer 854 may represent any of the transducer and horn combinations discussed herein, and may represent any of the transducer, horn and roller element combinations discussed herein.

FIG. 15B is a block diagram 870 of the example control module 852 of FIG. 15A. The control module 852 includes a processing component 872, a communications module 874, memory (including, for example, a data store in some examples) 876, and a power module 878. The processing component 872 may include one or more microcontrollers, microprocessors, or digital signal processors, in some examples, and may execute instructions stored in memory 876 to perform tasks for the control module 852. The communications module 874 may include a transmitter that can be used to transmit information, over wired connections directly in some examples, or in some examples via wired or wireless communications across one or more networks (e.g., local area networks (LANs), wide area networks (WANs), the Internet, Wi-Fi networks, cellular networks, virtual private networks (VPNs), mobile data networks (e.g., 3G/4G/5G networks, combinations of the foregoing, or others)).

In some examples, the communications module 874 includes a receiver that can be used to receive messages from other devices or systems. The memory 876 may include one or more of types of volatile memory or non-volatile memory including, in various examples, random-access memory (RAM), read-only memory (ROM), flash memory, storage devices (e.g., solid-state hard drive, hard disc drive) and/or other forms of volatile or non-volatile memory.

The power module 878 may provide one or more power supply voltages to power components of the control module 852 or other devices or components (e.g., transducer 854 in some examples). In some examples, the power module 878 can receive alternating current (AC) power, as from a wall outlet, and can convert the AC power into supply voltages usable by the control module 852 or other devices or components. In some examples, the power module 878 includes a battery, which in some examples may be rechargeable.

In some examples, control module 852 includes one or more sensors 880, such as, for example, one or more sensors that can detect when a wood element or a plurality of wood elements is in a target position for delivery of ultrasound energy. In some examples, the one or more sensors 880 may sense ambient environment parameters, such as one or more of temperature, humidity, barometric pressure, air quality, or other environmental parameters. In some examples, the control module 852 may receive input from one or more external sensors, or from one or more external devices in contact with one or more external sensors, and such input may provide the control module 852 with information relating to any of the foregoing sensor parameters. For example, the control module 852 may receive an input from an external sensor that indicates that a wood element or a plurality of wood elements is located in a target position for delivery of ultrasound energy.

A ultrasound delivery control module 882 can be used to manage or control aspects of ultrasound energy delivery to the plurality of wood elements 856. For example, the ultrasound delivery control module 882 may generate the one or more control signals 857 depicted in FIG. 15A. In various examples, the ultrasound delivery control module 882 may use input from the one or more sensors 880, from the communications module 874, and from memory 876, and may use the processing component 872 to manage or control aspects of the ultrasound energy delivery. FIG. 15B shows the ultrasound delivery control module 882 as a standalone module for simplicity, but in some implementations the module 882 may be included within the processing component 872. While the control module 852 is depicted in a separate enclosure from the transducer 854 in FIG. 15A, in some examples the control module 852, or one or more portions of the control module 852, may be located within the transducer 854.

With reference again to FIG. 15A, the control module 852 may direct, for example via one or more control signals 857, the ultrasound transducer 854 to deliver varying amounts of ultrasound energy to the plurality of wood elements 856, which in this example includes wood elements 858a, 858b, 858c, and 858d arranged vertically, in a similar manner to the wood elements of FIG. 4. In some examples, the control module 852 may direct, for example via one or more control signals 857, the ultrasound transducer 854 to deliver ultrasound energy to various locations or portions of the plurality of wood elements 856.

The control module may direct that a first amount of ultrasound energy 860 be delivered to a first location or portion of the plurality of wood elements, such as to wood elements 858a, 858b, and 858c, for example. This may stimulate bonding of wood elements 858a, 858b, and 858c, for example. The control module may then direct that a second amount of ultrasound energy 862, such as a lower amount of ultrasound energy, be delivered to a second location or portion of the plurality of wood elements, such as to wood element 858d, for example, which may stimulate bonding of element 858d to element 858c. Each of elements 858a, 858b, and 858c may be one type of wood element, such as wood strands, for example, and element 858d may be another type of wood element, such as a wood veneer, for example. The wood veneer 858d may be more delicate that the wood strands 858a, 858b, 858c, for example, and may advantageously benefit from the lower amount of delivered ultrasound energy 860 in stimulating its bonding to element 858c, for example. In some examples, the control module 852 may include motion controller 746 of FIG. 12C, and may provide motion control functionality to the ultrasound transducer 854.

In a general aspect, a system for manufacturing a composite wood product includes an applicator configured to apply a filler material to a plurality of wood elements, and an ultrasound transducer configured to deliver ultrasound energy to the plurality of wood elements, where the ultrasound energy has a frequency within a frequency range of 10 kHz-20 MHz.

Implementations can include one or more of the following. The plurality of wood elements may be bonded into a composite wood product. The applicator may include an adhesive applicator, and the filler material may include an adhesive. The filler material may not include an adhesive. The filler material may include a plastic. The filler material may include a metal. The plurality of wood elements may be arranged in a proximity to one another prior to the ultrasound transducer delivering the ultrasound energy to the plurality of wood elements. The applicator may apply the filler material to the plurality of wood elements concurrently with the ultrasound transducer delivering the ultrasound energy to the plurality of wood elements. The ultrasound transducer may deliver the ultrasound energy to the plurality of wood elements prior to the applicator applying the filler material to the plurality of wood elements. The ultrasound transducer may deliver the ultrasound energy to the plurality of wood elements after the applicator applies the filler material to the plurality of wood elements. The system may also include a press configured to apply a compression force to the plurality of wood elements. The press may apply the compression force to the plurality of wood elements prior to the ultrasound transducer delivering the ultrasound energy to the plurality of wood elements. The press may apply the compression force to the plurality of wood elements concurrently with the ultrasound transducer delivering the ultrasound energy to the plurality of wood elements. The press may apply the compression force to the plurality of wood elements after the ultrasound transducer delivers the ultrasound energy to the plurality of wood elements. The ultrasound energy may have a frequency within a frequency range of 15 kHz-1 MHz. The ultrasound energy may have a frequency within a frequency range of 20 kHz-100 kHz. The system may further include a defect inspection component, the ultrasound transducer may be further configured to deliver an additional amount of ultrasound energy to the composite wood product, and the defect inspection component may be configured to inspect the composite wood product for a defect. The defect inspection component may include a camera. The system may further include a defect inspection component and a second ultrasound transducer, the second ultrasound transducer may be configured to deliver ultrasound energy to the composite wood product, and the defect inspection component may be configured to inspect the composite wood product for a defect. The defect inspection component may include a camera. The ultrasound transducer may be further configured to deliver ultrasound energy to the plurality of wood elements prior to the applicator applying the filler material to the plurality of wood elements. The delivering the ultrasound energy to the plurality of wood elements prior to the applicator applying the filler material to the plurality of wood elements may clean the plurality of wood elements. The system may further include a treatment applicator configured to apply a treatment to the composite wood product, and the ultrasound transducer may be further configured to deliver an additional amount of ultrasound energy to the composite wood product. The system may further include a treatment applicator and a second ultrasound transducer, the treatment applicator may be configured to apply a treatment to the composite wood product, and the second ultrasound transducer may be configured to deliver ultrasound energy to the composite wood product. The ultrasound transducer may be selected from the group of a Langevin transducer, a ring transducer, a cymbal transducer, a dome transducer, a horn transducer, a pyramid transducer, a wedge transducer, and a spherical transducer. The ultrasound transducer may generate the ultrasound energy as a rectangular wave. The ultrasound transducer may generate the ultrasound energy as a sinusoidal wave. The ultrasound transducer may generate the ultrasound energy as a wave selected from the group of a trapezoidal wave and a triangular wave. The ultrasound transducer may generate the ultrasound energy as a continuous waveform. The ultrasound transducer may generate the ultrasound energy as a pulsed waveform. The system may further include a conveyor configured to transport the plurality of wood elements. The system may further include a funnel configured to guide the plurality of wood elements onto the conveyor. The system may further include a chamber configured to house the plurality of wood elements.

In a general aspect, a system for manufacturing a composite wood product includes an applicator configured to apply a filler material to a plurality of wood elements and an ultrasound transducer configured to generate ultrasound energy, where the ultrasound energy has a frequency within a frequency range of 10 kHz-20 MHz. The system also includes a roller element that includes a cylindrical body configured to rotate about an axis, where the cylindrical body includes an outer surface. The system further includes an ultrasound horn configured to guide the ultrasound energy to the roller element, where the roller element is configured to deliver the ultrasound energy to the plurality of wood elements, and where the roller element is configured such that at least a portion of the outer surface of the cylindrical body remains in physical contact with at least one wood element of the plurality of wood elements as the ultrasound energy is being delivered.

Implementations can include one or more of the following. The outer surface of the cylindrical body may be substantially smooth. The outer surface of the cylindrical body may include a plurality of recessed features. The outer surface of the cylindrical body may include a plurality of dimples. The outer surface of the cylindrical body may include a plurality of protrusions. At least one protrusion of the plurality of protrusions may include an outer surface that is rounded. At least one protrusion of the plurality of protrusions may include an outer surface that is substantially flat. At least one protrusion of the plurality of protrusions may include an outer surface that includes a point. At least one protrusion of the plurality of protrusions may include an outer surface that includes a ridge. The plurality of wood elements may be bonded into a composite wood product. The applicator may include an adhesive applicator, and the filler material may include an adhesive. The filler material may not include an adhesive. The filler material may include a plastic. The filler material may include a metal. The plurality of wood elements may be arranged in a proximity to one another prior to the roller element delivering the ultrasound energy to the plurality of wood elements. The applicator may apply the filler material to the plurality of wood elements concurrently with the roller element delivering the ultrasound energy to the plurality of wood elements. The roller element may deliver the ultrasound energy to the plurality of wood elements prior to the applicator applying the filler material to the plurality of wood elements. The roller element may deliver the ultrasound energy to the plurality of wood elements after the applicator applies the filler material to the plurality of wood elements. The system may further include a press configured to apply a compression force to the plurality of wood elements. The press may apply the compression force to the plurality of wood elements prior to the roller element delivering the ultrasound energy to the plurality of wood elements. The press may apply the compression force to the plurality of wood elements concurrently with the roller element delivering the ultrasound energy to the plurality of wood elements. The press may apply the compression force to the plurality of wood elements after the roller element delivers the ultrasound energy to the plurality of wood elements. The ultrasound energy may have a frequency within a frequency range of 15 kHz-1 MHz. The ultrasound energy may have a frequency within a frequency range of 20 kHz-100 kHz. The system may further include a defect inspection component, the roller element may be further configured to deliver ultrasound energy to the composite wood product, and the defect inspection component may be configured to inspect the composite wood product for a defect. The defect inspection component may include a camera. The roller element may be further configured to deliver ultrasound energy to the plurality of wood elements prior to the applicator applying the filler material to the plurality of wood elements. The delivering the ultrasound energy to the plurality of wood elements prior to the applicator applying the filler material to the plurality of wood elements may clean the plurality of wood elements. The system may further include a treatment applicator configured to apply a treatment to the composite wood product, and the roller element may be further configured to deliver ultrasound energy to the composite wood product. The ultrasound transducer may generate the ultrasound energy as a rectangular wave. The ultrasound transducer may generate the ultrasound energy as a sinusoidal wave. The ultrasound transducer may generate the ultrasound energy as a wave selected from the group of a trapezoidal wave and a triangular wave. The ultrasound transducer may generate the ultrasound energy as a continuous waveform. The ultrasound transducer may generate the ultrasound energy as a pulsed waveform. The system may further include a conveyor configured to transport the plurality of wood elements. The system may further include a funnel configured to guide the plurality of wood elements onto the conveyor. The system may further include a chamber configured to house the plurality of wood elements.

In a general aspect, a system for manufacturing a composite wood product includes an applicator configured to apply a filler material to a plurality of wood elements, and an ultrasound transducer configured to generate ultrasound energy, where the ultrasound energy has a frequency within a frequency range of 10 kHz-20 MHz. The system also includes a roller element that includes a spherical body, where the spherical body includes an outer surface. They system further includes an ultrasound horn configured to guide the ultrasound energy to the roller element, where the roller element is configured to deliver the ultrasound energy to the plurality of wood elements, and where the roller element is configured such that at least a portion of the outer surface of the spherical body remains in physical contact with at least one wood element of the plurality of wood elements as the ultrasound energy is being delivered.

Implementations can include one or more of the following. The outer surface of the spherical body may be substantially smooth. The outer surface of the spherical body may include a plurality of recessed features. The outer surface of the spherical body may include a plurality of dimples. The outer surface of the spherical body may include a plurality of protrusions. At least one protrusion of the plurality of protrusions may include an outer surface that is rounded. At least one protrusion of the plurality of protrusions may include an outer surface that is substantially flat. At least one protrusion of the plurality of protrusions may include an outer surface that includes a point. At least one protrusion of the plurality of protrusions may include an outer surface that includes a ridge. The plurality of wood elements may be bonded into a composite wood product. The applicator may include an adhesive applicator, and the filler material may include an adhesive. The filler material may not include an adhesive. The filler material may include a plastic. The filler material may include a metal. The plurality of wood elements may be arranged in a proximity to one another prior to the roller element delivering the ultrasound energy to the plurality of wood elements. The applicator may apply the filler material to the plurality of wood elements concurrently with the roller element delivering the ultrasound energy to the plurality of wood elements. The roller element may deliver the ultrasound energy to the plurality of wood elements prior to the applicator applying the filler material to the plurality of wood elements. The roller element may deliver the ultrasound energy to the plurality of wood elements after the applicator applies the filler material to the plurality of wood elements. The system may further include a press configured to apply a compression force to the plurality of wood elements. The press may apply the compression force to the plurality of wood elements prior to the roller element delivering the ultrasound energy to the plurality of wood elements. The press may apply the compression force to the plurality of wood elements concurrently with the roller element delivering the ultrasound energy to the plurality of wood elements. The press may apply the compression force to the plurality of wood elements after the roller element delivers the ultrasound energy to the plurality of wood elements. The ultrasound energy may have a frequency within a frequency range of 15 kHz-1 MHz. The ultrasound energy may have a frequency within a frequency range of 20 kHz-100 kHz. The system may further include a defect inspection component, the roller element may be further configured to deliver ultrasound energy to the composite wood product, and the defect inspection component may be configured to inspect the composite wood product for a defect. The defect inspection component may include a camera. The roller element may be further configured to deliver ultrasound energy to the plurality of wood elements prior to the applicator applying the filler material to the plurality of wood elements. The delivering the ultrasound energy to the plurality of wood elements prior to the applicator applying the filler material to the plurality of wood elements may clean the plurality of wood elements. The system may further include a treatment applicator configured to apply a treatment to the composite wood product, and the roller element may be further configured to deliver ultrasound energy to the composite wood product. The ultrasound transducer may generate the ultrasound energy as a rectangular wave. The ultrasound transducer may generate the ultrasound energy as a sinusoidal wave. The ultrasound transducer may generate the ultrasound energy as a wave selected from the group of a trapezoidal wave and a triangular wave. The ultrasound transducer may generate the ultrasound energy as a continuous waveform. The ultrasound transducer may generate the ultrasound energy as a pulsed waveform. The system may further include a conveyor configured to transport the plurality of wood elements. The system may further include a funnel configured to guide the plurality of wood elements onto the conveyor. The system may further include a chamber configured to house the plurality of wood elements.

The above description provides examples of some implementations. Other implementations that are not explicitly described above are also possible, such as implementations based on modifications and/or variations of the features described above. For example, the techniques described above may be implemented in different orders, with the inclusion of one or more additional steps, and/or with the exclusion of one or more of the identified steps. Similarly, the devices, systems, and methods may include one or more additional features, may exclude one or more of the identified features, and/or include the identified features or steps combined in a different way than presented above. Features or steps that are described as singular may be implemented as a plurality of such features or steps. Likewise, features or steps that are described as a plurality may be implemented as singular instances of such features or steps. Additionally, the steps and techniques described above as being performed by some devices and/or systems may alternatively, or additionally, be performed by other devices and/or systems that are described above or other devices and/or systems that are not explicitly described. The drawings are intended to be illustrative and may not precisely depict some implementations. Variations in sizing, placement, shapes, angles, curvatures, and/or the positioning of features relative to each other are possible. Accordingly, other implementations are within the scope of the following claims.

What is claimed is:

1. A method of manufacturing a composite wood product, comprising:
applying a filler material to a plurality of wood elements;
applying a compression force to the plurality of wood elements, the compression force applied by a press that includes a first surface that applies the compression force to the plurality of wood elements; and
bonding the plurality of wood elements into a composite wood product, the bonding comprising delivering ultrasound energy to the plurality of wood elements, wherein the ultrasound energy has a frequency within a frequency range of 10 kHz-20 MHz;
wherein the ultrasound energy is delivered by an ultrasound transducer that is integral with the press, and wherein the ultrasound transducer is arranged to be flush with the first surface of the press.

2. The method of claim 1, wherein the filler material comprises an adhesive.

3. The method of claim 1, wherein the filler material does not include an adhesive.

4. The method of claim 1, wherein the filler material comprises a plastic.

5. The method of claim 1, wherein the filler material comprises a metal.

6. The method of claim 1, wherein the plurality of wood elements are arranged, prior to the bonding the plurality of wood elements, in a proximity to one another.

7. The method of claim 1, wherein the ultrasound energy is delivered to the plurality of wood elements after the applying the filler material to the plurality of wood elements.

8. The method of claim 1, wherein the applying the compression force to the plurality of wood elements occurs prior to the delivering the ultrasound energy to the plurality of wood elements.

9. The method of claim 1, wherein the applying the compression force to the plurality of wood elements occurs concurrently with the delivering the ultrasound energy to the plurality of wood elements.

10. The method of claim 1, wherein the applying the compression force to the plurality of wood elements occurs after the delivering the ultrasound energy to the plurality of wood elements.

11. The method of claim 1, wherein the frequency is within a frequency range of 15 kHz-1 MHz.

12. The method of claim 11, wherein the frequency is within a frequency range of 20 kHz-100 kHz.

13. The method of claim 1, further comprising inspecting the composite wood product for a defect, the inspecting comprising delivering ultrasound energy to the composite wood product.

14. The method of claim 1, further comprising, prior to the applying the filler material, pretreating the plurality of wood elements, the pretreating comprising delivering ultrasound energy to the plurality of wood elements.

15. The method of claim 14, wherein the pretreating comprising delivering ultrasound energy to the plurality of wood elements cleans the plurality of wood elements.

16. The method of claim 1, further comprising, after the bonding into the composite wood product, applying a treatment to the composite wood product and delivering ultrasound energy to the composite wood product.

17. The method of claim 1, wherein both the compression force and the ultrasound energy are delivered in a same direction with respect to the plurality of wood elements.

18. The method of claim 17, wherein the same direction is a downward direction.

19. The method of claim 17, wherein the same direction is a lateral direction.

20. A method of manufacturing a composite wood product, comprising:
applying a filler material to a plurality of wood elements;
applying a compression force to the plurality of wood elements, the compression force applied by a press that includes a first surface that applies the compression force to the plurality of wood elements; and
bonding the plurality of wood elements into a composite wood product, the bonding comprising delivering ultrasound energy to the plurality of wood elements, wherein the ultrasound energy has a frequency within a frequency range of 10 kHz-20 MHz;
wherein the ultrasound energy is delivered by an ultrasound transducer that is integral with the press, and wherein the ultrasound transducer is arranged to be recessed from the first surface of the press.

21. The method of claim 20, wherein the filler material comprises an adhesive.

22. The method of claim 20, wherein the filler material does not include an adhesive.

23. The method of claim 20, wherein the filler material comprises a plastic.

24. The method of claim 20, wherein the filler material comprises a metal.

25. The method of claim 20, wherein the plurality of wood elements are arranged, prior to the bonding the plurality of wood elements, in a proximity to one another.

26. The method of claim 20, wherein the ultrasound energy is delivered to the plurality of wood elements after the applying the filler material to the plurality of wood elements.

27. The method of claim 20, wherein the applying the compression force to the plurality of wood elements occurs prior to the delivering the ultrasound energy to the plurality of wood elements.

28. The method of claim 20, wherein the applying the compression force to the plurality of wood elements occurs concurrently with the delivering the ultrasound energy to the plurality of wood elements.

29. The method of claim 20, wherein the applying the compression force to the plurality of wood elements occurs after the delivering the ultrasound energy to the plurality of wood elements.

30. The method of claim 20, wherein the frequency is within a frequency range of 15 kHz-1 MHz.

31. The method of claim 30, wherein the frequency is within a frequency range of 20 kHz-100 kHz.

32. The method of claim 20, further comprising inspecting the composite wood product for a defect, the inspecting comprising delivering ultrasound energy to the composite wood product.

33. The method of claim 20, further comprising, prior to the applying the filler material, pretreating the plurality of wood elements, the pretreating comprising delivering ultrasound energy to the plurality of wood elements.

34. The method of claim 33, wherein the pretreating comprising delivering ultrasound energy to the plurality of wood elements cleans the plurality of wood elements.

35. The method of claim 20, further comprising, after the bonding into the composite wood product, applying a treatment to the composite wood product and delivering ultrasound energy to the composite wood product.

36. The method of claim 20, wherein both the compression force and the ultrasound energy are delivered in a same direction with respect to the plurality of wood elements.

37. The method of claim 36, wherein the same direction is a downward direction.

38. The method of claim 36, wherein the same direction is a lateral direction.

* * * * *